United States Patent
Batlle et al.

(10) Patent No.: US 12,123,036 B2
(45) Date of Patent: Oct. 22, 2024

(54) SOLUBLE ACE2 VARIANTS AND USES THEREFOR

(71) Applicant: Northwestern University, Evanston, IL (US)

(72) Inventors: Daniel Batlle, Evanston, IL (US); Jan Wysocki, Chicago, IL (US)

(73) Assignee: Northwestern University, Evanston, IL (US)

( * ) Notice: Subject to any disclaimer, the term of this patent is extended or adjusted under 35 U.S.C. 154(b) by 205 days.

(21) Appl. No.: 17/187,502

(22) Filed: Feb. 26, 2021

(65) Prior Publication Data

US 2021/0371841 A1 Dec. 2, 2021

Related U.S. Application Data

(60) Provisional application No. 62/981,924, filed on Feb. 26, 2020, provisional application No. 63/130,039, filed on Dec. 23, 2020.

(51) Int. Cl.
| | |
|---|---|
| *C12N 9/48* | (2006.01) |
| *A61K 38/48* | (2006.01) |
| *A61K 47/60* | (2017.01) |
| *A61P 31/14* | (2006.01) |
| *C12N 9/96* | (2006.01) |

(52) U.S. Cl.
CPC .......... *C12N 9/48* (2013.01); *A61K 38/4813* (2013.01); *A61K 47/60* (2017.08); *A61P 31/14* (2018.01); *C12N 9/96* (2013.01); *C12Y 304/17023* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 4,540,930 | A | 9/1985 | Siedband |
| 5,538,721 | A | 7/1996 | Babcock |
| 6,884,771 | B1 | 4/2005 | Acton |
| 7,396,664 | B2 | 7/2008 | Daly |
| 10,314,893 | B2 * | 6/2019 | Daniell ............... A61K 9/19 |
| 10,443,049 | B2 | 10/2019 | Batlle |
| 11,078,471 | B2 | 8/2021 | Batlle |
| 2003/0113726 | A1 | 6/2003 | Tsuchihashi |
| 2011/0020315 | A1 * | 1/2011 | Loibner ............... A61P 31/04 424/94.63 |
| 2018/0230447 | A1 | 8/2018 | Batlle |
| 2019/0358304 | A1 | 11/2019 | Daniell |
| 2020/0181594 | A1 | 6/2020 | Batlle |
| 2021/0386837 | A1 | 12/2021 | Batlle |
| 2022/0033794 | A1 | 2/2022 | Batlle |

FOREIGN PATENT DOCUMENTS

| | | |
|---|---|---|
| WO | 2011039096 A1 | 4/2011 |
| WO | 2013119870 A1 | 8/2013 |
| WO | 2013177398 A2 | 11/2013 |
| WO | 2014108530 A1 | 7/2014 |
| WO | 2018140456 A1 | 8/2018 |
| WO | 2021237239 A1 | 11/2021 |

OTHER PUBLICATIONS

Huentelman et al.,"Cloning and characterization of a secreted form of angiotensin-converting enzyme 2", Regulatory Peptides, 122: 61-67 (Year: 2004).*
Dall'Acqua et al.,"Properties of Human IgG1s Engineered for Enhanced Binding to the Neonatal Fc Receptor (FcRn)", The Journal of Biological Chemistry, vol. 281, No. 33, pp. 23514-23524 Aug. 18, 2006.*
Sun, Y., et al., "Cationic Nanoparticles Directly Bind Angiotensin-Converting Enzyme 2 and Induce Acute Lung Injury in Mice", Part. Fibre. Toxicol., 2015, vol. 12, No. 4, pp. 1-13.
Sung SH, et al. Blockade of vascular endothelial growth factor signaling ameliorates diabetic albuminuria in mice. J Am Soc Nephrol. 2006; 17:3093-104.
Suzuki T, et al. Importance of neonatal FcR in regulating the serum half-life of therapeutic proteins containing the Fc domain of human IgG1: a comparative study of the affinity of monoclonal antibodies and Fc-fusion proteins to human neonatal FcR. Journal of immunology (Baltimore, Md : 1950). 2010;184:1968-76.
Suzuki T, et al. Inflammation and angiotensin II. The International Journal of Biochemistry & Cell Biology. 2003;35:881-900.
Suzuki Y. et al. "Inflammation and angiotensin II." The international journal of biochemistry & cell biology 35.6 (2003): 881-900.
Tatusova, T., et al. "BLAST 2 Sequences, a new tool for comparing protein and nucleotide sequences." FEMS microbiology letters 174.2 (1999): 247-250.
Thomas MC, et al. Genetic Ace2 deficiency accentuates vascular inflammation and atherosclerosis in the ApoE knockout mouse. Circ Res 107, 888-897 (2010).

(Continued)

*Primary Examiner* — Anand U Desai
(74) *Attorney, Agent, or Firm* — Choate, Hall & Stewart LLP; Brenda Herschbach Jarrell

(57) ABSTRACT

The present disclosure provides various insights relating to treatment of viral infection with soluble ACE2 variants, specifically including soluble human ACE2 (hACE2) variants. For example, the present disclosure teaches that decoy activity, which may intercept virus-receptor interactions, and ACE2 enzymatic activity can provide separate contributions to therapeutic efficacy; among other things, the present disclosure provides particular therapeutic regimens (e.g., relating to treatment of particular patient populations and/or to dosing regimens, combination therapies, etc.) for certain soluble ACE2 variants. Still further, the present disclosure provides certain particular ACE2 variants and methods of making and/or using them, including in accordance with particular therapeutic regimens.

30 Claims, 30 Drawing Sheets

Specification includes a Sequence Listing.

(56) References Cited

OTHER PUBLICATIONS

Tikellis C, et al. Identification of angiotensin converting enzyme 2 in the rodent retina. Curr Eye Res 29, 419-427 (2004).
Tipnis SR, et al. A human homolog of angiotensin-converting enzyme. Cloning and functional expression as a captopril-insensitive carboxypeptidase. J Biol Chem 275, 33238-33243 (2000).
Tisoncik JR, et al. Into the eye of the cytokine storm. Microbiol Mol Biol Rev 76, 16-32 (2012).
Tolouian, R., et al. COVID-19 interactions with angiotensin-converting enzyme 2 (ACE2) and the kinin system; looking at a potential treatment. Journal of Renal Injury Prevention, 2020. 9(2): p. e19-e19.
Tom B, et al. ACE-versus chymase- dependent angiotensin II generation in human coronary arteries: a matter of efficiency? Arteriosclerosis, thrombosis, and vascular biology. 2003;23:251-6.
Towler P, et al. ACE2 X-ray structures reveal a large hinge-bending motion important for inhibitor binding and catalysis. J Biol Chem. 2004;279:17996-8007.
Ueno, M., et al. "Accelerated wound healing of alkali-burned corneas in MRL mice is associated with a reduced inflammatory signature." Investigative ophthalmology & visual science 46.11 (2005): 4097-4106.
Urata H, et al. Angiotensin II-forming pathways in normal and failing human hearts. Circ Res. 1990;66:883-90.
Urata H, et al. Cellular localization and regional distribution of an angiotensin II-forming chymase in the heart. The Journal of clinical investigation. 1993;91:1269-81.
Urata H, et al. Identification of a highly specific chymase as the major angiotensin II-forming enzyme in the human heart. J Biol Chem. 1990;265:22348-57.
Vallabh NA, et al. Mitochondrial dysfunction and oxidative stress in corneal disease. Mitochondrion 36, 103-113 (2017).
Van De Wal RM, et al. Determinants of increased angiotensin II levels in severe chronic heart failure patients despite ACE inhibition. International journal of cardiology. 2006;106:367-72.
Van Den Meiracker AH, et al. Partial escape of angiotensin converting enzyme (ACE) inhibition during prolonged ACE inhibitor treatment: does it exist and does it affect the antihypertensive response? Journal of hypertension. 1992;10:803-12.
Varagic, J., et al. "ACE2: angiotensin II/angiotensin-(1-7) balance in cardiac and renal injury." Current hypertension reports 16.3 (2014): 420.
Velez JC. Prolyl carboxypeptidase: a forgotten kidney angiotensinase. Focus on "Identification of prolyl carboxypeptidase as an alternative enzyme for processing of renal angiotensin II using mass spectrometry". American journal of physiology Cell physiology. 2013;304:C939-40.
Verdecchia, P., et al. The pivotal link between ACE2 deficiency and SARS-CoV-2 infection. European journal of internal medicine 76 (2020): 14-20.
Vickers C, et al. Hydrolysis of biological peptides by human angiotensin-converting enzyme-related carboxypeptidase. J Biol Chem. 2002;277:14838-43.
Walls, A.C., et al., Structure, function, and antigenicity of the SARS-CoV-2 spike glycoprotein. Cell 181.2 (2020): 281.
Wan Y, et al. Receptor recognition by the novel coronavirus from Wuhan: an analysis based on decade-long structural studies of SARS coronavirus. Journal of virology 94.7 (2020): e00127-20.
Wan, Y., et al. Molecular Mechanism for Antibody-Dependent Enhancement of Coronavirus Entry. J Virol, 2020. 94(5).
Wang, J., et al. "The ACE2-deficient mouse: A model for a cytokine storm-driven inflammation." The FASEB Journal 34.8 (2020): 10505-10515.
Wang, Q., et al., Structural and Functional Basis of SARS-CoV-2 Entry by Using Human ACE2. Cell 181.4 (2020): 894.
Wei CC, et al. Mast cell chymase limits the cardiac efficacy of Ang I-converting enzyme inhibitor therapy in rodents. The Journal of clinical investigation. 2010;120:1229-39.
Welches WR, et al. Evidence that prolyl endopeptidase participates in the processing of brain angiotensin. Journal of hypertension. 1991;9:631-8.
Wilson SE, et al. The corneal wound healing response: cytokine-mediated interaction of the epithelium, stroma, and inflammatory cells. Prog Retin Eye Res 20, 625-637 (2001).
Winkler, E.S., et al. SARS-CoV-2 infection of human ACE2-transgenic mice causes severe lung inflammation and impaired function. Nature immunology 21.11 (2020): 1327-1335.
Wu H, et al: AKI and collapsing glomerulopathy associated with COVID-19 and APOL 1 high-risk genotype. Journal of the American Society of Nephrology, 31: 1688-1695, 2020.
Wysocki J, et al. "A Novel Soluble ACE2 Variant with Prolonged Duration of Action Neutralizes SARS-CoV-2 Infection in Human Kidney Organoids," J. Am. Soc. Nephr., 32:795-803, 2021.
Wysocki J, et al. ACE and ACE2 activity in diabetic mice. Diabetes. 2006;55:2132-9.
Wysocki J, et al. ACE2 deficiency increases NADPH-mediated oxidative stress in the kidney. Physiological reports 2, e00264 (2014).
Wysocki J, et al. Angiotensin-converting enzyme 2 amplification limited to the circulation does not protect mice from development of diabetic nephropathy. Kidney Int. 2017;91:1336-1346.
Wysocki J, et al. Kidney and Lung ACE2 expression after an ACE inhibitor or an Ang II receptor blocker: implications for COVID-19. bioRxiv, 2020: p. 2020.05.20.106658.
Wysocki J, et al. Novel Variants of Angiotensin Converting Enzyme-2 of Shorter Molecular Size to Target the Kidney Renin Angiotensin System. Biomolecules 9, (2019).
Wysocki J, et al. Plasma and Kidney Angiotensin Peptides: Importance of the Aminopeptidase A/ Angiotensin III Axis. Am J Hypertens. 2015;28:1418-26.
Wysocki J, et al. Regulation of urinary ACE2 in diabetic mice. Am J Physiol Renal Physiol. 2013;305:F600-11.
Wysocki J, et al. Targeting the degradation of angiotensin II with recombinant angiotensin-converting enzyme 2: prevention of angiotensin II-dependent hypertension. Hypertension. 2010;55:90-8.
Wysocki J, et al. Urinary prorenin is increased in patients with type 1 diabetes and nephropathy. ASN. 2016;Kidney Week.
Wysocki J, et al. Urine RAS components in mice and people with type 1 diabetes and chronic kidney disease. Am J Physiol Renal Physiol. 2017:ajprenal 00074 2017.
Xiao, F., et al. "Characterization of angiotensin-converting enzyme 2 ectodomain shedding from mouse proximal tubular cells." PloS One, vol. 9, Issue 1, Jan. 2014 (2014).
Xu Z, et al. Pathological findings of COVID-19 associated with acute respiratory distress syndrome. Lancet Respir Med, (2020).
Yamada K, et al. Converting enzyme determines plasma clearance of angiotensin-(1-7). Hypertension. 1998;32:496-502.
Yan R, et al. Structural basis for the recognition of SARS-CoV-2 by full-length human ACE2. Science, 367: 1444-1448, 2020.
Yang, X., et al. Clinical course and outcomes of critically ill patients with SARS-CoV-2 pneumonia in Wuhan, China: a single-centered, retrospective, observational study. The Lancet. Respiratory Medicine 8.5 (2020): 475.
Okada H. A Look at Transactivation of the EGF Receptor by Angiotensin II. J Am Soc Nephrol. 2012;23:183-5.
Oladunni, F.S., et al. Lethality of SARS-CoV-2 infection in K18 human angiotensin converting enzyme 2 transgenic mice. bioRxiv, 2020.
Onabajo, O. O., et al. "Interferons and viruses induce a novel primate-specific isoform dACE2 and not the SARS-CoV-2 receptor ACE2." BioRxiv (2020).
Oudit GY, et al. Loss of angiotensin-converting enzyme-2 leads to the late development of angiotensin II-dependent glomerulosclerosis. The American journal of pathology. 2006;168:1808-20.
Pach, S., et al., ACE2-Variants Indicate Potential SARS-CoV-2-Susceptibility in Animals: An Extensive Molecular Dynamics Study. bioRxiv, 2020.
Palazzo V, et al. The genetic and clinical spectrum of a large cohort of patients with distal renal tubular acidosis. Kidney international. 2017.

(56) References Cited

OTHER PUBLICATIONS

Pan, X.-w., et al., Identification of a potential mechanism of acute kidney injury during the COVID-19 outbreak: a study based on single-cell transcriptome analysis. Intensive care medicine, 46.6 (2020): 1114-1116.
Park CH et al. Albumin absorption and catabolism by isolated perfused proximal convoluted tubules of the rabbit. The Journal of clinical investigation. 1984;73:767-77.
Park JK, et al. MicroRNAs-103/107 coordinately regulate macropinocytosis and autophagy. The Journal of cell biology 215, 667-685 (2016).
Park S, et al. Major role for ACE-independent intrarenal ANG II formation in type II diabetes. Am J Physiol Renal Physiol. 2010;298:F37-48.
Park SH, et al. Type I interferons and the cytokine TNF cooperatively reprogram the macrophage epigenome to promote inflammatory activation. Nat Immunol 18, 1104-1116 (2017).
Pei, G., et al., Renal involvement and early prognosis in patients with COVID-19 pneumonia. Journal of the American Society of Nephrology, 2020. 31(6): p. 1157-1165.
Peng H, et al. microRNA-31/factor-inhibiting hypoxia-inducible factor 1 nexus regulates keratinocyte differentiation. Proceedings of the National Academy of Sciences of the United States of America 109, 14030-14034 (2012).
Peti-Peterdi J, et al. Activation of the renal renin-angiotensin system in diabetes—new concepts. Nephrology Dialysis Transplantation. 2008;23:3047-3049.
Price DA, et al. The paradox of the low-renin state in diabetic nephropathy. J Am Soc Nephrol. 1999;10:2382-91.
Quaggin SE et al. Toward a mouse model of diabetic nephropathy: is endothelial nitric oxide synthase the missing link? Journal of the American Society of Nephrology : JASN. 2007;18:364-6.
Raij L. The pathophysiologic basis for blocking the renin-angiotensin system in hypertensive patients with renal disease. Am J Hypertens. 2005;18:95s-99s.
Rennke HG, et al. Role of molecular charge in glomerular permeability. Tracer studies with cationized ferritins. The Journal of cell biology. 1975;67:638-46.
Richardson, S., et al., Presenting characteristics, comorbidities, and outcomes among 5700 patients hospitalized with COVID-19 in the New York City area. JAMA 323.20 (2020).
Roig E, et al. Clinical implications of increased plasma angiotensin II despite ACE inhibitor therapy in patients with congestive heart failure. European heart journal. 2000;21:53-7.
Ronco, C. et al. Kidney involvement in COVID-19 and rationale for extracorporeal therapies. Nature Reviews Nephrology, 2020: p. 1-3.
Ronco, C., et al. Management of acute kidney injury in patients with COVID-19. The Lancet Respiratory Medicine 8.7 (2020): 738-742.
Rosenberg ME, et al. The paradox of the renin-angiotensin system in chronic renal disease. Kidney Int. 1994;45:403-10.
Ross MJ et al. ACE2 as therapy for glomerular disease: the devil is in the detail. Kidney International. 2017;91:1269-1271.
Russo LM, et al. The normal kidney filters nephrotic levels of albumin retrieved by proximal tubule cells: retrieval is disrupted in nephrotic states. Kidney Int. 2007;71:504-13.
Saika, S., et al. "Loss of tumor necrosis factor α potentiates transforming growth factor β-mediated pathogenic tissue response during wound healing." The American journal of pathology 168.6 (2006): 1848-1860.
Saito A, et al. Molecular mechanisms of receptor-mediated endocytosis in the renal proximal tubular epithelium. Journal of biomedicine & biotechnology. 2010;2010:403272.
Salem ES, et al. Insulin treatment attenuates renal ADAM17 and ACE2 shedding in diabetic Akita mice. Am J Physiol Renal Physiol. 2014;306:F629-39.
Sand KMK, et al. Dissection of the Neonatal Fc Receptor (FcRn)-Albumin Interface Using Mutagenesis and Anti-FcRn Albumin-blocking Antibodies. The Journal of biological chemistry. 2014;289:17228-17239.
Sandoval RM, et al. Multiple factors influence glomerular albumin permeability in rats. J Am Soc Nephrol. 2012;23:447-57.
Santos RA, et al. Angiotensin-converting enzyme 2, angiotensin-(1-7) and Mas: new players of the renin-angiotensin system. The Journal of endocrinology. 2013;216:R1-r17.
Sarav M, et al. Renal FcRn reclaims albumin but facilitates elimination of IgG. J Am Soc Nephrol. 2009;20:1941-52.
Schaller, T., et al. Postmortem examination of patients with COVID-19. JAMA. Jun. 23, 2020; 323(24): 2518-2520.
Schellenberger V, et al. A recombinant polypeptide extends the in vivo half-life of peptides and proteins in a tunable manner. Nat Biotechnol. 2009;27:1186-90.
Schelling JR, et al. Cytoskeleton-dependent endocytosis is required for apical type 1 angiotensin II receptor-mediated phospholipase C activation in cultured rat proximal tubule cells. J Clin Invest. 1992;90:2472-80.
Schulte S. Half-life extension through albumin fusion technologies. Thrombosis research. 2009;124 Suppl 2:S6-8.
Serfozo P, et al. Ang II (Angiotensin II) Conversion to Angiotensin-(1-7) in the Circulation is POP (Prolyloligopeptidase)-Dependent and ACE2 (Angiotensin-Converting Enzyme 2)-Independent. Hypertension 75, 173-182 (2020).
Shariat-Madar Z, et al. Identification and characterization of prolylcarboxypeptidase as an endothelial cell prekallikrein activator. J Biol Chem. 2002;277:17962-9.
Sharman DC, et al. Gradual reactivation of vascular angiotensin I to angiotensin II conversion during chronic ACE inhibitor therapy in patients with diabetes mellitus. Diabetologia. 2007;50:2061-6.
Shiigai T et al. Late escape from the antiproteinuric effect of ace inhibitors in nondiabetic renal disease. American journal of kidney diseases : the official journal of the National Kidney Foundation. 2001;37:477-83.
Simoes e Silva AC et al. ACE inhibition, ACE2 and angiotensin-(1?7) axis in kidney and cardiac inflammation and fibrosis. Pharmacological Research. 2016;107:154-162.
Simoes e Silva AC, et al. ACE2, angiotensin-(1-7) and Mas receptor axis in inflammation and fibrosis. British journal of pharmacology. 2013;169:477-92.
Simonnet, A., et al. High prevalence of obesity in severe acute respiratory syndrome coronavirus-2 (SARS-CoV-2) requiring invasive mechanical ventilation. Obesity, 2020.
Soler MJ, et al. ACE2 inhibition worsens glomerular injury in association with increased ACE expression in streptozotocin-induced diabetic mice. Kidney Int. 2007;72:614-23.
Sotozono, C., et al. "Cytokine expression in the alkali-burned cornea." Current eye research 16.7 (1997): 670-676.
Spiekermann et al., Receptor-mediated immunoglobulin G transport across mucosal barriers in adult life: functional expression of FcRn in the mammalian lung. J. Exp. Med. Aug. 5, 2002;196(3)-10.
Stepp MA, et al. Wounding the cornea to learn how it heals. Experimental eye research 121, 178-193 (2014).
Strohl WR. Fusion Proteins for Half-Life Extension of Biologics as a Strategy to Make Biobetters. BioDrugs : clinical immunotherapeutics, biopharmaceuticals and gene therapy. 2015;29:215-39.
Su, H., et al., Renal histopathological analysis of 26 postmortem findings of patients with COVID-19 in China. Kidney international, 2020.
Sun L, et al. p66Shc mediates high-glucose and angiotensin II-induced oxidative stress renal tubular injury via mitochondrial-dependent apoptotic pathway. Am J Physiol Renal Physiol. 2010;299:F1014-25.
Japan Patent Office. Notice of Reasons for Rejection for application 2019-540076. Mailed on Dec. 21, 2021. With translation. 12 pages.
Jevsevar S, et al. PEGylation of therapeutic proteins. Biotechnology journal. 2010;5:113-28.
Jiang F, et al. Angiotensin-converting enzyme 2 and angiotensin 1-7: novel therapeutic targets. Nature reviews Cardiology. 2014;11:413-26.
Jin HY, et al. Deletion of angiotensin-converting enzyme 2 exacerbates renal inflammation and injury in apolipoprotein E-deficient mice through modulation of the nephrin and TNF-alpha-TNFRSF1A signaling. J Transl Med 13, 255 (2015).

(56) References Cited

OTHER PUBLICATIONS

Kamiyama M, et al. Urinary angiotensinogen as a novel early biomarker of intrarenal renin-angiotensin system activation in experimental type 1 diabetes. Journal of pharmacological sciences. 2012;119:314-23.
Kanwar YS et al. Anionic sites in the glomerular basement membrane. In vivo and in vitro localization to the laminae rarae by cationic probes. The Journal of cell biology. 1979;81:137-53.
Kanwar YS et al. Presence of heparan sulfate in the glomerular basement membrane. Proceedings of the National Academy of Sciences of the United States of America. 1979;76:1303-7.
Kaplan N, et al. FIH-1 engages novel binding partners to positively influence epithelial proliferation via p63. FASEB J 34, 525-539 (2020).
Kazama K, et al. Angiotensin II impairs neurovascular coupling in neocortex through NADPH oxidase-derived radicals. Circ Res 95, 1019-1026 (2004).
Kobori H, et al. Urinary excretion of angiotensinogen reflects intrarenal angiotensinogen production. Kidney international. 2002;61:579-585.
Kok RJ, et al. Specific delivery of captopril to the kidney with the prodrug captopril-lysozyme. The Journal of pharmacology and experimental therapeutics. 1999;288:281-5.
Komine N, et al. Effect of combining an ACE inhibitor and an angiotensin II receptor blocker on plasma and kidney tissue angiotensin II levels. American journal of kidney diseases : the official journal of the National Kidney Foundation. 2002;39:159-64.
Kontermann RE. Strategies for extended serum half-life of protein therapeutics. Current opinion in biotechnology. 2011;22:868-76.
Kruse, R.L., Therapeutic strategies in an outbreak scenario to treat the novel coronavirus originating in Wuhan, China. F1000Res, 2020. 9: p. 72.
Ksiazek TG, et al. A novel coronavirus associated with severe acute respiratory syndrome. N Engl J Med 2003;348:1953-66.
Kuba K, et al. A crucial role of angiotensin converting enzyme 2 (ACE2) in SARS coronavirus-induced lung injury. Nat Med 11, 875-879 (2005).
Kusnadi A, et al. The Cytokine TNF Promotes Transcription Factor SREBP Activity and Binding to Inflammatory Genes to Activate Macrophages and Limit Tissue Repair. Immunity 51, 241-257 e249 (2019).
Lai CC, et al. Severe acute respiratory syndrome coronavirus 2 (SARS-CoV-2) and coronavirus disease—2019 (COVID-19): The epidemic and the challenges. Int J Antimicrob Agents 55, 105924 (2020).
Lan J, et al. Structure of the SARS-CoV-2 spike receptor-binding domain bound to the ACE2 receptor. Nature, 581: 215-220, 2020.
Lei C. Potent neutralization of 2019 novel coronavirus by recombinant ACE2-Ig bioRxiv 2020.
Levy OE, et al. Novel exenatide analogs with peptidic albumin binding domains: potent anti-diabetic agents with extended duration of action. PloS one. 2014;9:e87704.
Lewis EJ, et al. Renoprotective effect of the angiotensin-receptor antagonist irbesartan in patients with nephropathy due to type 2 diabetes. The New England journal of medicine. 2001;345:851-60.
Lewis EJ, et al. The effect of angiotensin-converting enzyme inhibition on diabetic nephropathy. The Collaborative Study Group. The New England journal of medicine. 1993;329:1456-62.
Li M, et al. Involvement of chymase-mediated angiotensin II generation in blood pressure regulation. The Journal of clinical investigation. 2004;114:112-20.
Li, F., Receptor recognition mechanisms of coronaviruses: a decade of structural studies. Journal of virology, 2015. 89 (4): p. 1954-1964.
Li, W., et al. Efficient replication of severe acute respiratory syndrome coronavirus in mouse cells is limited by murine angiotensin-converting enzyme 2. J Virol, 2004. 78(20): p. 11429-33.
Li, W., et al., Angiotensin-converting enzyme 2 is a functional receptor for the SARS coronavirus. Nature, 2003. 426 (6965): p. 450-454.
Li, Z., et al. Caution on Kidney Dysfunctions of COVID-19 Patients. medRxiv, 2020: p. 2020.02.08.20021212.
Lin CI, et al. Instillation of particulate matter 2.5 induced acute lung injury and attenuated the injury recovery in ACE2 knockout mice. Int J Biol Sci 14, 253-265 (2018).
Liu P, et al. A Fluorometric Method of Measuring Carboxypeptidase Activities for Angiotensin II and Apelin 13. Scientific Reports. 2017.
Lo C-S, et al. Heterogeneous Nuclear Ribonucleoprotein F Suppresses Angiotensinogen Gene Expression and Attenuates Hypertension and Kidney Injury in Diabetic Mice. Diabetes. 2012;61:2597-2608.
Lorenz JN. Chymase: the other ACE? Am J Physiol Renal Physiol. 2010;298:F35-6.
MacDougall IC, et al. Pharmacokinetics of novel erythropoiesis stimulating protein compared with epoetin alfa in dialysis patients. J Am Soc Nephrol. 1999;10:2392-5.
Maier C, et al. Prolylcarboxypeptidase deficiency is associated with increased blood pressure, glomerular lesions, and cardiac dysfunction independent of altered circulating and cardiac angiotensin II. Journal of molecular medicine (Berlin, Germany). 2017.
Matsuyama S, et al. Enhanced isolation of SARS-CoV-2 by TMPRSS2-expressing cells. Proceedings of the National Academy of Sciences, 117: 7001-7003, 2020.
McCray, P.B., et al. Lethal infection of K18-hACE2 mice infected with severe acute respiratory syndrome coronavirus. Journal of virology, 2007. 81(2): p. 813-821.
Menachery VD, et al. A SARS-like cluster of circulating bat coronaviruses shows potential for human emergence. Nat Med 2015;21:1508-13.
Mezzano SA, et al. Angiotensin II and Renal Fibrosis. Hypertension. 2001;38:635-638.
Mills KT, et al. Increased urinary excretion of angiotensinogen is associated with risk of chronic kidney disease. Nephrology Dialysis Transplantation. 2012;27:3176-3181.
Moestrup SK et al. Megalin- and cubilin-mediated endocytosis of protein-bound vitamins, lipids, and hormones in polarized epithelia. Annual review of nutrition. 2001;21:407-28.
Mohamed, M.M., et al. Acute kidney injury associated with coronavirus disease 2019 in Urban New Orleans. Kidney360 (2020): 10-34067.
Monteil, V., et al., Inhibition of SARS-CoV-2 Infections in Engineered Human Tissues Using Clinical-Grade Soluble Human ACE2. Cell, 2020. 181(4): p. 905-913 e7.
Mori J, et al. Angiotensin 1-7 mediates renoprotection against diabetic nephropathy by reducing oxidative stress, inflammation, and lipotoxicity. Am J Physiol Renal Physiol. 2014;306:F812-21.
Nadarajah R, et al. Podocyte-specific overexpression of human angiotensin-converting enzyme 2 attenuates diabetic nephropathy in mice. Kidney Int. 2012;82:292-303.
Nagasu H, et al. Activation of endothelial NAD(P)H oxidase accelerates early glomerular injury in diabetic mice. Lab Invest. 2016;96:25-36.
Nakagawa T, et al. Diabetic endothelial nitric oxide synthase knockout mice develop advanced diabetic nephropathy. Journal of the American Society of Nephrology : JASN. 2007;18:539-50.
Nakamura T, et al. LRIG1 inhibits STAT3-dependent inflammation to maintain corneal homeostasis. J Clin Invest 124, 385-397 (2014).
Nguyen MT, et al. Short-term nonpressor angiotensin II infusion stimulates sodium transporters in proximal tubule and distal nephron. Physiological reports. 2015;3.
Nilvebrant J et al. The albumin-binding domain as a scaffold for protein engineering. Computational and structural biotechnology journal. 2013;6:e201303009.
Nita M, et al. The Role of the Reactive Oxygen Species and Oxidative Stress in the Pathomechanism of the Age-Related Ocular Diseases and Other Pathologies of the Anterior and Posterior Eye Segments in Adults. Oxid Med Cell Longev 2016, 3164734 (2016).
Yang, X.H., et al. Mice transgenic for human angiotensin-converting enzyme 2 provide a model for SARS coronavirus infection. Comp Med, 2007. 57(5): p. 450-9.

(56) References Cited

OTHER PUBLICATIONS

Ye M, et al. Glomerular localization and expression of Angiotensin-converting enzyme 2 and Angiotensin-converting enzyme: implications for albuminuria in diabetes. J Am Soc Nephrol. 2006;17:3067-75.

Ye M, et al. Increased ACE 2 and decreased ACE protein in renal tubules from diabetic mice: a renoprotective combination? Hypertension. 2004;43:1120-5.

Ye M, et al. Murine recombinant angiotensin-converting enzyme 2: effect on angiotensin II-dependent hypertension and distinctive angiotensin-converting enzyme 2 inhibitor characteristics on rodent and human angiotensin-converting enzyme 2. Hypertension. 2012;60:730-40.

Ye M, et al. Urinary Angiotensinogen (AOG) is Increased in Type I Diabetes with Microalbuminuria. 2016.

Ying T, et al. Engineered soluble monomeric IgG1 CH3 domain: generation, mechanisms of function, and implications for design of biological therapeutics. J Biol Chem. 2013;288:25154-64.

Zatz R, et al. Prevention of diabetic glomerulopathy by pharmacological amelioration of glomerular capillary hypertension. The Journal of clinical investigation. 1986;77:1925-30.

Zhang MZ, et al. Role of blood pressure and the renin-angiotensin system in development of diabetic nephropathy (DN) in eNOS-/-db/db mice. Am J Physiol Renal Physiol. 2012;302:F433-8.

Zhang, H., et al. Angiotensin-converting enzyme 2 (ACE2) as a SARS-CoV-2 receptor: molecular mechanisms and potential therapeutic target. Intensive care medicine, 2020: p. 1-5.

Zhao HJ, et al. Endothelial nitric oxide synthase deficiency produces accelerated nephropathy in diabetic mice. J Am Soc Nephrol. 2006;17:2664-9.

Zhao, S., et al. "Extending the serum half-life of G-CSF via fusion with the domain III of human serum albumin." BioMed research international 2013 (2013).

Zheng, Y.-Y., et al. COVID-19 and the cardiovascular system. Nature Reviews Cardiology, 2020. 17(5): p. 259-260.

Zhou P, et al. A pneumonia outbreak associated with a new coronavirus of probable bat origin. Nature 579, 270-273 (2020).

Zhou P, et al. Kidney-targeted drug delivery systems. Acta Pharmaceutica Sinica B. 2014;4:37-42.

Zhou, M., et al. Coronavirus disease 2019 (COVID-19): a clinical update. Frontiers of medicine, 2020: p. 1-10.

Zhuang, M.W., et al. Increasing Host Cellular Receptor-Angiotensin-Converting Enzyme 2 (ACE2) Expression by Coronavirus may Facilitate 2019-nCoV (or SARS-CoV-2) Infection. Journal of medical virology 92.11 (2020): 2693-2701.

Ziegler, C.G., et al. SARS-CoV-2 receptor ACE2 is an interferon-stimulated gene in human airway epithelial cells and is detected in specific cell subsets across tissues. Cell 181.5 (2020): 1016-1035.

Zou K, et al. Specific tumor-derived CCL2 mediated by pyruvate kinase M2 in colorectal cancer cells contributes to macrophage recruitment in tumor microenvironment. Tumour Biol 39, 1010428317695962 (2017).

Zoufaly, A., et al., Human recombinant soluble ACE2 in severe COVID-19. The Lancet Respiratory Medicine, 8.11 (2020): 1154-1158.

Afkarian M, et al. Urinary excretion of RAS, BMP, and WNT pathway components in diabetic kidney disease. Physiological reports. 2014;2:e12010.

Akilesh S, et al. Podocytes use FcRn to clear IgG from the glomerular basement membrane. Proceedings of the National Academy of Sciences of the United States of America. 2008;105:967-72.

Altschul, S. F., et al. "Basic local alignment search tool." Journal of molecular biology 215.3 (1990): 403-410.

Andersen JT, et al. Structure-based mutagenesis reveals the albumin-binding site of the neonatal Fc receptor. Nature communications. 2012;3:610.

Andersen, J. T., et al. "Extending half-life by indirect targeting of the neonatal Fc receptor (FcRn) using a minimal albumin binding domain." Journal of biological chemistry 286.7 (2011): 5234-5241.

Anderson S, et al. Renal renin-angiotensin system in diabetes: functional, immunohistochemical, and molecular biological correlations. Am J Physiol. 1993;265:F477-86.

Anderson S, et al. Therapeutic advantage of converting enzyme inhibitors in arresting progressive renal disease associated with systemic hypertension in the rat. Journal of Clinical Investigation. 1986;77:1993-2000.

Anonymous. Human ACE2. Nov. 30, 2016. Retrieved from the Internet. URL:https://www.uniprot.org/uniprot/Q9BYF1.txt?version=153.

Athyros VG, et al. Angiotensin II reactivation and aldosterone escape phenomena in renin-angiotensin-aldosterone system blockade: is oral renin inhibition the solution? Expert opinion on pharmacotherapy. 2007;8:529-35.

Bae EH, et al. Murine recombinant angiotensin-converting enzyme 2 attenuates kidney injury in experimental Alport syndrome. Kidney Int. 2017.

Baggish AL et al. Radiopharmaceutical agents for myocardial perfusion imaging. Circulation. 2008;118:1668-74.

Batlle D, et al. Angiotensin-converting enzyme 2: enhancing the degradation of angiotensin II as a potential therapy for diabetic nephropathy. Kidney Int. 2012;81:520-8.

Batlle D, et al. New aspects of the renin-angiotensin system: angiontensin-converting enzyme 2—a potential target for treatment of hypertension and diabetic nephropathy, Curr. Opin Nephrol. Hypertens. May 2008; 17 (3):250-7.

Batlle D, et al. Soluble angiotensin-converting enzyme 2: a potential approach for coronavirus infection therapy? Clin Sci (Lond) 134, 543-545 (2020).

Batlle, D., et al. (2020). Acute kidney injury in COVID-19: emerging evidence of a distinct pathophysiology. Journal of the American Society of Nephrology, 31(7), 1380-1383.

Becker BN, et al. The Type 1 Angiotensin II Receptor Tail Affects Receptor Targeting, Internalization, and Membrane Fusion Properties. Molecular Pharmacology. 2004;65:362.

Benigni A, et al. Angiotensin II revisited: new roles in inflammation, immunology and aging. EMBO Molecular Medicine. 2010;2:247-57.

Berry C. Clinical implications of increased plasma angiotensin II concentrations despite ACE inhibitor therapy in patients with congestive heart failure: the issue of non-compliance with therapy. European heart journal. 2000;21:1484-5.

Biollaz J, et al. Enalapril maleate and a lysine analogue (MK-521) in normal volunteers; relationship between plasma drug levels and the renin angiotensin system. British journal of clinical pharmacology. 1982;14:363-8.

Birn, H., et al. "Renal albumin absorption in physiology and pathology." Kidney international 69.3 (2006): 440-449.

Bitonti et al., Pulmonary delivery of an erythropoietin Fc fusion protein in non-human primates through an immunoglobulin transport pathway. Proc. Natl. Acad. Sci. USA Jun. 29, 2004; 101(26):9763-8.

Border WA et al. Interactions of Transforming Growth Factor-β and Angiotensin II in Renal Fibrosis. Hypertension. 1998;31:181-188.

Bracken, C. J., et al. "Bi-paratopic and multivalent VH domains block ACE2 binding and neutralize SARS-CoV-2." Nature chemical biology 17.1 (2021): 113-121.

Brasen JC, et al. Local pH domains regulate NHE3-mediated Na(+) reabsorption in the renal proximal tubule. Am J Physiol Renal Physiol. 2014;307:F1249-62.

Brenner BM, et al. Effects of losartan on renal and cardiovascular outcomes in patients with type 2 diabetes and nephropathy. The New England journal of medicine. 2001;345:861-9.

Brosius FC, 3rd, et al. Mouse models of diabetic nephropathy. J Am Soc Nephrol. 2009;20:2503-12.

Burnier M. Angiotensin II type 1 receptor blockers. Circulation 103, 904-912 (2001).

Caliceti P et al. Pharmacokinetic and biodistribution properties of poly(ethylene glycol)-protein conjugates. Advanced drug delivery reviews. 2003;55:1261-77.

Campbell DJ. The site of angiotensin production. Journal of hypertension. 1985;3:199-207.

(56) References Cited

OTHER PUBLICATIONS

Carney EF. Diabetic nephropathy: Renoprotective effects of angiotensin 1-7. Nature reviews Nephrology. 2014;10:240.
Chan, K. K., et al. "Engineering human ACE2 to optimize binding to the spike protein of SARS coronavirus 2." Science 369.6508 (2020): 1261-1265.
Chaudhury C, et al. Albumin binding to FcRn: distinct from the FcRn-IgG interaction. Biochemistry. 2006;45:4983-90.
Chen C, et al. LNMAT1 promotes lymphatic metastasis of bladder cancer via CCL2 dependent macrophage recruitment. Nat Commun 9, 3826 (2018).
Chen J, et al. EGFR Signaling Promotes TGFβ-Dependent Renal Fibrosis. J Am Soc Nephrol. 2012;23:215-24.
Cheng HF, et al. Angiotensin II upregulates type-1 angiotensin II receptors in renal proximal tubule. Journal of Clinical Investigation. 1995;95:2012-2019.
Cheng, Y., et al., Kidney disease is associated with in-hospital death of patients with COVID-19. Kidney international, 2020.
Cheng, Y., et al., Kidney impairment is associated with in-hospital death of COVID-19 patients. medRxiv, 2020: p. 2020.02.18.20023242.
Christensen EI et al. Megalin and cubilin: multifunctional endocytic receptors. Nature reviews Molecular cell biology. 2002;3:256-66.
Christlieb AR, et al. Plasma renin activity and hypertension in diabetes mellitus. Diabetes. 1976;25:969-74.
Comper WD et al. Charge selectivity in kidney ultrafiltration. Kidney Int. 1995;47:1242-51.
Cosgrove D, et al. Collagen COL4A3 knockout: a mouse model for autosomal Alport syndrome. Genes & development. 1996;10:2981-92.
Crowley SD, et al. Angiotensin II causes hypertension and cardiac hypertrophy through its receptors in the kidney. Proceedings of the National Academy of Sciences of the United States of America. 2006;103:17985-90.
Culver S, et al. Intrarenal Angiotensin-Converting Enzyme: the Old and the New. Current hypertension reports. 2017;19:80.
Davidson, A.M., et al. The interaction of SARS-CoV-2 and other coronavirus with Angiotensin Converting Enzyme 2 (ACE2) as their main receptor: therapeutic implications. Hypertension, 2020.
Diao, B., et al., Human kidney is a target for novel severe acute respiratory syndrome coronavirus 2 (SARS-CoV-2) infection. MedRxiv, 2020.
Dickson LE, et al. The proximal tubule and albuminuria: really! J Am Soc Nephrol. 2014;25:443-53.
Dolman ME, et al. Drug targeting to the kidney: Advances in the active targeting of therapeutics to proximal tubular cells. Advanced drug delivery reviews. 2010;62:1344-57.
Donoghue M, et al. A novel angiotensin-converting enzyme-related carboxypeptidase (ACE2) converts angiotensin I to angiotensin 1-9. Circ Res 87, E1-9 (2000).
Du L, et al. The spike protein of SARS-CoV—a target for vaccine and therapeutic development. Nat Rev Microbiol 2009;7:226-36.
Durvasula RV et al. Activation of a local renin angiotensin system in podocytes by glucose. Am J Physiol Renal Physiol. 2008;294:F830-9.
Durvasula RV, et al. Activation of a local tissue angiotensin system in podocytes by mechanical strain. Kidney Int. 2004;65:30-9.
Elbadawi, M. et al. Organoids of human airways to study infectivity and cytopathy of SARS-CoV-2. Lancet Respir Med, 2020: e55-e56.
European Patent Office. Examination Report for application 18745455.8. Mailed on Jun. 6, 2021. 16 pages.
European Patent Office. Extended European Search Report for application 18745455.8. Mailed on Oct. 12, 2020. 10 pages.
Ferrario CM, et al. Effect of angiotensin-converting enzyme inhibition and angiotensin II receptor blockers on cardiac angiotensin-converting enzyme 2. Circulation. 2005;111:2605-10.
Fisher ND, et al. Renal response to captopril reflects state of local renin system in healthy humans. Kidney Int. 1999;56:635-41.
Fleming, A.B. et al. Current studies of convalescent plasma therapy for COVID-19 may underestimate risk of antibody-dependent enhancement. J Clin Virol, 2020. 127: p. 104388.
Fogo AB. Renal fibrosis and the renin-angiotensin system. Advances in nephrology from the Necker Hospital. 2001;31:69-87.
Franssen EJ, et al. Low molecular weight proteins as carriers for renal drug targeting. Preparation of drug-protein conjugates and drug-spacer derivatives and their catabolism in renal cortex homogenates and lysosomal lysates. J Med Chem. 1992;35:1246-59.
Franssen EJ, et al. Low molecular weight proteins as carriers for renal drug targeting: naproxen-lysozyme. Pharmaceutical research. 1991;8:1223-30.
Garvin, M.R., et al. A mechanistic model and therapeutic interventions for COVID-19 involving a RAS-mediated bradykinin storm. Elife, 2020. 9: p. e59177.
Gheblawi, M., et al. Angiotensin-converting enzyme 2: SARS-CoV-2 receptor and regulator of the renin-angiotensin system: celebrating the 20th anniversary of the discovery of ACE2. Circulation research, 2020. 126(10): p. 1456-1474.
Giani JF, et al. Renal angiotensin-converting enzyme is essential for the hypertension induced by nitric oxide synthesis inhibition. J Am Soc Nephrol. 2014;25:2752-63.
Glass, W.G., et al. Mechanisms of host defense following severe acute respiratory syndrome-coronavirus (SARS-CoV) pulmonary infection of mice. The Journal of Immunology, 2004. 173(6): p. 4030-4039.
Gonzalez AA, et al. Renal medullary cyclooxygenase-2 and (pro)renin receptor expression during angiotensin II-dependent hypertension. Am J Physiol Renal Physiol. 2014;307:F962-70.
Gonzalez-Villalobos RA, et al. The absence of intrarenal ACE protects against hypertension. The Journal of clinical investigation. 2013;123:2011-23.
Goorno WE, et al. Relation of renal gluconeogenesis to ammonia production in the dog and rat. The American journal of physiology. 1967;213:969-74.
Gralinski LE, et al. Molecular pathology of emerging coronavirus infections. J Pathol 235, 185-195 (2015).
Grima M, et al. Renal tissue angiotensins during converting enzyme inhibition in the spontaneously hypertensive rat. Clinical and experimental hypertension (New York, NY : 1993). 1997;19:671-85.
Grobe JL, et al. Prevention of angiotensin II-induced cardiac remodeling by angiotensin-(1-7). American journal of physiology Heart and circulatory physiology. 2007;292:H736-42.
Grobe N, et al. Identification of prolyl carboxypeptidase as an alternative enzyme for processing of renal angiotensin II using mass spectrometry. American journal of physiology Cell physiology. 2013;304:C945-53.
Guan, W.-j., et al. Clinical characteristics of coronavirus disease 2019 in China. New England journal of medicine, 2020. 382(18): p. 1708-1720.
Guo Y, et al. PEG-like nanoprobes: multimodal, pharmacokinetically and optically tunable nanomaterials. PloS one. 2014;9:e95406.
Guo, W., et al. Diabetes is a risk factor for the progression and prognosis of COVID-19. Diabetes/metabolism research and reviews, 2020: p. e3319.
Gupta N, et al. Comparison of prognostic value of Roper Hall and Dua classification systems in acute ocular burns. Br J Ophthalmol 95, 194-198 (2011).
Gurley SB et al. The renin-angiotensin system and diabetic nephropathy. Seminars in nephrology. 2007;27:144-52.
Gurley SB, et al. Altered blood pressure responses and normal cardiac phenotype in ACE2-null mice. J Clin Invest 116, 2218-2225 (2006).
Gurley SB, et al. AT(1A) Angiotensin Receptors in the Renal Proximal Tubule Regulate Blood Pressure. Cell metabolism. 2011;13:469-75.
Gurwitz, D., Angiotensin receptor blockers as tentative SARS-CoV-2 therapeutics. Drug development research, 2020.
Guy JL, et al. Angiotensin-converting enzyme-2 (ACE2): comparative modeling of the active site, specificity requirements, and chloride dependence. Biochemistry 42, 13185-13192 (2003).
Haas M, et al. Specific drug delivery to the kidney. Cardiovascular drugs and therapy. 2002;16:489-96.

(56) References Cited

OTHER PUBLICATIONS

Haber PK, et al. Angiotensin-converting enzyme 2-independent action of presumed angiotensin-converting enzyme 2 activators: studies in vivo, ex vivo, and in vitro. Hypertension. 2014;63:774-82.

Hanff TC, et al. Is There an Association Between COVID-19 Mortality and the Renin-Angiotensin System—a Call for Epidemiologic Investigations. Clin Infect Dis, (2020).

Harlan SM, et al. Progressive Renal Disease Established by Renin-Coding Adeno-Associated Virus-Driven Hypertension in Diverse Diabetic Models. J Am Soc Nephrol. 2017.

Haschke M, et al. Pharmacokinetics and pharmacodynamics of recombinant human angiotensin-converting enzyme 2 in healthy human subjects. Clinical pharmacokinetics. 2013;52:783-92.

Hassan, A.O., et al. A SARS-CoV-2 infection model in mice demonstrates protection by neutralizing antibodies. Cell, 2020: 744-753.

Haymann JP, et al. Characterization and localization of the neonatal Fc receptor in adult human kidney. J Am Soc Nephrol. 2000;11:632-9.

Hirsch, J.S., et al. Acute Kidney Injury in Patients Hospitalized With COVID-19. Kidney International, (2020): 209.

Hoffmann, M., et al., SARS-CoV-2 Cell Entry Depends on ACE2 and TMPRSS2 and is Blocked by a Clinically Proven Protease Inhibitor. Cell, 2020. 181(2): 271-280.

Hudkins KL, et al. BTBR Ob/Ob mutant mice model progressive diabetic nephropathy. J Am Soc Nephrol. 2010;21:1533-42.

Ichimura T, et al: KIM-1/TIM-1 is a Receptor for SARS-CoV-2 in Lung and Kidney. medRxiv, 2020.

Igic R. Four decdes of ocular renin-angiotensin and kallikrein-kinin systems (1977-2017). Experimental eye research 166, 74-83 (2018).

Imai Y, et al. Angiotensin-converting enzyme 2 protects from severe acute lung failure. Nature 436, 112-116 (2005).

Ingelfinger JR, et al. In situ hybridization evidence for angiotensinogen messenger RNA in the rat proximal tubule. An hypothesis for the intrarenal renin angiotensin system. The Journal of clinical investigation. 1990;85:417-23.

Ingert C, et al. [Renal tissue angiotensins during converting enzyme inhibition of angiotensin I in spontaneously hypertensive rat]. Archives des maladies du coeur et des vaisseaux. 1997;90:1135-41.

International Search Report and Written Opinion for PCT/US2018/014991 dated Apr. 12, 2018.

International Searching Authority. International Search Report and Written Opinion for application PCT/US2021/020066. Mailed on Sep. 14, 2021. 13 pages.

International Searching Authority. International Search Report and Written Opinion for application PCT/US2021/070575. Mailed on Oct. 14, 2021. 9 pages.

Israili ZH. Clinical pharmacokinetics of angiotensin II (AT1) receptor blockers in hypertension. J Hum Hypertens 14 Suppl 1, S73-86 (2000).

Jacobs, S. A., et al. "Fusion to a highly stable consensus albumin binding domain allows for tunable pharmacokinetics." Protein Engineering, Design and Selection 28.10 (2015): 385-393.

Burrell, L. M., ACE2, a new regulator of the renin-angiotensin system, Trends in Endocrinology & Metabolism, 15(4):166-169 (2004).

Chappell, M. C. et al., Update on the Angiotensin converting enzyme 2-Angiotensin (1-7)-MAS receptor axis: fetal programing, sex differences, and intracellular pathways, Frontiers in Endocrinology, 4:201 (2014).

Ferrario, C. M., ACE 2: More of Ang 1-7 or less Ang II?, Current Opinion in Nephrology and Hypertension, 20(1):1-6 (2011).

Guy, J. L. et al., Membrane-associated zinc peptidase families: comparing ACE and ACE2, Biochim Biophys Acta, 1751(1):2-8, (2005).

Hassler, L. et al., A novel soluble ACE2 protein provides lung and kidney protection in mice susceptible to lethal SARS-CoV-2 infection, JASN Basic Research, 33:1293-1307 (2022).

Hassler, L. et al., Intranasal soluble ACE2 improves survival and prevents brain SARS-CoV-2 infection, Life Science Alliance, 6(7):e202301969, 13 pages (2023).

Liu, P. et al., Novel ACE2-Fc chimeric fusion provides long-lasting hypertension control and organ protection in mouse models of systemic renin angiotensin system activation, Kidney international, 94(1):114-125 (2018).

Marquez, A. et al., An update on ACE2 amplification and its therapeutic potential, Acta Physiol (Oxf), 231(1):e13513 (2021).

Mori, Y. et al., KIM-1/TIM-1 is a Receptor for SARS-CoV-2 in Lung and Kidney, medRxiv, Jan. 11, 2022;2020.09.16.20190694. doi: 10.1101/2020.09.16.20190694. Preprint, Abstract only.

Ortega, J. T. et al., Role of changes in SARS0COV-2 spike protein in the interaction with the human ACE2 receptor: An in silico analysis, EXCLI Journal, 19:410-417 (2020).

Poglitsch, M. et al., Recombinant Expression and Characterization of Human and Murine ACE2: Species-Specific Activation of the Alternative Renin-Angiotensin—System, International journal of hypertension, 2012:428950 (2012).

Schrimpf, A. et al., Hinge-type dimertization of proteins by a tetracysteine peptide of high pairing specificity, Biochemistry, 57:3658-3664 (2018).

Shiraz, M. et al., A Novel Angiotensin-Converting Enzyme 2 Truncate Markedly Improves Ischemic AKI [Abstract]. J Am Soc Nephrol 30, 2019:3 pages.

Sodhi, C. P. et al., Attenuation of pulmonary ACE2 activity impairs inactivation of des-Arg9 bradykinin/BKB1R axis and facilitates LPS-induced neutrophil infiltration, American Journal of Physiology—Lung Cellular and Molecular Physiology, 314(1):LI 7-L31 (2018).

Svilenov, H. L. et al., Multimeric ACE2-IgM fusions as broadly active antivirals that potently neutralize SARS-CoV-2 variants, Comm. Biology, 5(1237):7 pages (2022).

Torchia, J. A. et al., Optimized ACE2 decoys neutralize antibody-resistant SARS-CoV-2 variants through functional receptor mimicry and treat infection in vivo, Science Advances, 8(eabq6527):1-17 (2022).

Wrapp, D. et al., Cryo-EM structure of the 2019-nCoV spike in the prefusion conformation, Science, 367(6483):1260-1263 (2020).

Wu, H. et al., Comparative analysis and refinement of human PSC-derived kidney organoid differentiation with single-cell transcriptomics, Cell Stem Cell., 23(6):869-881. e868.e8 (2018).

* cited by examiner

Amino acid sequence of DDC: KCHWECRGCRLVC; source of the sequence: DOI: 10.1021/acs.biochem.8b00475

SEQUENCE LISTING

<160> NUMBER OF SEQ ID NOS: 16

<210> SEQ ID NO 1
<211> LENGTH: 805
<212> TYPE: PRT
<213> ORGANISM: Homo sapiens

<400> SEQUENCE: 1

```
Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205
```

-continued

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
            245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
        290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
        610                 615                 620

-continued

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
            645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Val Thr Ala Pro
            675                 680                 685

Lys Asn Val Ser Asp Ile Ile Pro Arg Thr Glu Val Glu Lys Ala Ile
        690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 2
<211> LENGTH: 805
<212> TYPE: PRT
<213> ORGANISM: Mus musculus

<400> SEQUENCE: 2

Met Ser Ser Ser Ser Trp Leu Leu Leu Ser Leu Val Ala Val Thr Thr
1               5                   10                  15

Ala Gln Ser Leu Thr Glu Glu Asn Ala Lys Thr Phe Leu Asn Asn Phe
            20                  25                  30

Asn Gln Glu Ala Glu Asp Leu Ser Tyr Gln Ser Ser Leu Ala Ser Trp
        35                  40                  45

Asn Tyr Asn Thr Asn Ile Thr Glu Glu Asn Ala Gln Lys Met Ser Glu
    50                  55                  60

Ala Ala Ala Lys Trp Ser Ala Phe Tyr Glu Glu Gln Ser Lys Thr Ala
65                  70                  75                  80

Gln Ser Phe Ser Leu Gln Glu Ile Gln Thr Pro Ile Ile Lys Arg Gln
                85                  90                  95

Leu Gln Ala Leu Gln Gln Ser Gly Ser Ser Ala Leu Ser Ala Asp Lys
            100                 105                 110

Asn Lys Gln Leu Asn Thr Ile Leu Asn Thr Met Ser Thr Ile Tyr Ser
        115                 120                 125

Thr Gly Lys Val Cys Asn Pro Lys Asn Pro Gln Glu Cys Leu Leu Leu
    130                 135                 140

Glu Pro Gly Leu Asp Glu Ile Met Ala Thr Ser Thr Asp Tyr Asn Ser
145                 150                 155                 160

Arg Leu Trp Ala Trp Glu Gly Trp Arg Ala Glu Val Gly Lys Gln Leu
                165                 170                 175

Arg Pro Leu Tyr Glu Glu Tyr Val Val Leu Lys Asn Glu Met Ala Arg
            180                 185                 190

```
Ala Asn Asn Tyr Asn Asp Tyr Gly Asp Tyr Trp Arg Gly Asp Tyr Glu
            195                 200                 205
Ala Glu Gly Ala Asp Gly Tyr Asn Tyr Asn Arg Asn Gln Leu Ile Glu
        210                 215                 220
Asp Val Glu Arg Thr Phe Ala Glu Ile Lys Pro Leu Tyr Glu His Leu
225                 230                 235                 240
His Ala Tyr Val Arg Arg Lys Leu Met Asp Thr Tyr Pro Ser Tyr Ile
                245                 250                 255
Ser Pro Thr Gly Cys Leu Pro Ala His Leu Leu Gly Asp Met Trp Gly
            260                 265                 270
Arg Phe Trp Thr Asn Leu Tyr Pro Leu Thr Val Pro Phe Ala Gln Lys
        275                 280                 285
Pro Asn Ile Asp Val Thr Asp Ala Met Met Asn Gln Gly Trp Asp Ala
        290                 295                 300
Glu Arg Ile Phe Gln Glu Ala Glu Lys Phe Phe Val Ser Val Gly Leu
305                 310                 315                 320
Pro His Met Thr Gln Gly Phe Trp Ala Asn Ser Met Leu Thr Glu Pro
                325                 330                 335
Ala Asp Gly Arg Lys Val Val Cys His Pro Thr Ala Trp Asp Leu Gly
            340                 345                 350
His Gly Asp Phe Arg Ile Lys Met Cys Thr Lys Val Thr Met Asp Asn
                355                 360                 365
Phe Leu Thr Ala His His Glu Met Gly His Ile Gln Tyr Asp Met Ala
370                 375                 380
Tyr Ala Arg Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Pro Ser Asp Phe Gln Glu Asp Ser
            420                 425                 430
Glu Thr Glu Ile Asn Phe Leu Leu Lys Gln Ala Leu Thr Ile Val Gly
        435                 440                 445
Thr Leu Pro Phe Thr Tyr Met Leu Glu Lys Trp Arg Trp Met Val Phe
    450                 455                 460
Arg Gly Glu Ile Pro Lys Glu Gln Trp Met Lys Lys Trp Trp Glu Met
465                 470                 475                 480
Lys Arg Glu Ile Val Gly Val Val Glu Pro Leu Pro His Asp Glu Thr
                485                 490                 495
Tyr Cys Asp Pro Ala Ser Leu Phe His Val Ser Asn Asp Tyr Ser Phe
            500                 505                 510
Ile Arg Tyr Tyr Thr Arg Thr Ile Tyr Gln Phe Gln Phe Gln Glu Ala
        515                 520                 525
Leu Cys Gln Ala Ala Lys Tyr Asn Gly Ser Leu His Lys Cys Asp Ile
    530                 535                 540
Ser Asn Ser Thr Glu Ala Gly Gln Lys Leu Leu Lys Met Leu Ser Leu
545                 550                 555                 560
Gly Asn Ser Glu Pro Trp Thr Lys Ala Leu Glu Asn Val Val Gly Ala
                565                 570                 575
Arg Asn Met Asp Val Lys Pro Leu Leu Asn Tyr Phe Gln Pro Leu Phe
            580                 585                 590
Asp Trp Leu Lys Glu Gln Asn Arg Asn Ser Phe Val Gly Trp Asn Thr
        595                 600                 605
```

-continued

```
Glu Trp Ser Pro Tyr Ala Asp Gln Ser Ile Lys Val Arg Ile Ser Leu
            610                 615                 620

Lys Ser Ala Leu Gly Ala Asn Ala Tyr Glu Trp Thr Asn Asn Glu Met
625                 630                 635                 640

Phe Leu Phe Arg Ser Ser Val Ala Tyr Ala Met Arg Lys Tyr Phe Ser
                645                 650                 655

Ile Ile Lys Asn Gln Thr Val Pro Phe Leu Glu Glu Asp Val Arg Val
                660                 665                 670

Ser Asp Leu Lys Pro Arg Val Ser Phe Tyr Phe Val Thr Ser Pro
                675                 680                 685

Gln Asn Val Ser Asp Val Ile Pro Arg Ser Val Glu Asp Ala Ile
            690                 695                 700

Arg Met Ser Arg Gly Arg Ile Asn Asp Val Phe Gly Leu Asn Asp Asn
705                 710                 715                 720

Ser Leu Glu Phe Leu Gly Ile His Pro Thr Leu Glu Pro Pro Tyr Gln
                725                 730                 735

Pro Pro Val Thr Ile Trp Leu Ile Ile Phe Gly Val Val Met Ala Leu
                740                 745                 750

Val Val Val Gly Ile Ile Ile Leu Ile Val Thr Gly Ile Lys Gly Arg
                755                 760                 765

Lys Lys Lys Asn Glu Thr Lys Arg Glu Glu Asn Pro Tyr Asp Ser Met
770                 775                 780

Asp Ile Gly Lys Gly Glu Ser Asn Ala Gly Phe Gln Asn Ser Asp Asp
785                 790                 795                 800

Ala Gln Thr Ser Phe
                805

<210> SEQ ID NO 3
<211> LENGTH: 619
<212> TYPE: PRT
<213> ORGANISM: Homo sapiens

<400> SEQUENCE: 3

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175
```

```
Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590
```

```
Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys
            610                 615

<210> SEQ ID NO 4
<211> LENGTH: 605
<212> TYPE: PRT
<213> ORGANISM: Homo sapiens

<400> SEQUENCE: 4

Met Ser Ser Ser Trp Leu Leu Ser Leu Val Ala Val Thr Ala
  1               5                  10                  15

Ala Gln Ser Thr Ile Glu Glu Gln Ala Lys Thr Phe Leu Asp Lys Phe
             20                  25                  30

Asn His Glu Ala Glu Asp Leu Phe Tyr Gln Ser Ser Leu Ala Ser Trp
             35                  40                  45

Asn Tyr Asn Thr Asn Ile Thr Glu Glu Asn Val Gln Asn Met Asn Asn
         50                  55                  60

Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
             85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
        130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
            165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
        210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
            245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
        290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350
```

```
Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
        370                 375                 380

Tyr Ala Ala Gln Pro Phe Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
        450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly
        595                 600                 605

<210> SEQ ID NO 5
<211> LENGTH: 46
<212> TYPE: PRT
<213> ORGANISM: Artificial
<220> FEATURE:
<223> OTHER INFORMATION: Variant of Streptococcal G-protein albumin
      binding domain III

<400> SEQUENCE: 5

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 6
<211> LENGTH: 232
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15
```

-continued

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
             100                 105                 110

Leu Pro Ala Pro Ile Glu Lys Thr Ile Ser Lys Ala Lys Gly Gln Pro
             115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 7
<211> LENGTH: 107
<212> TYPE: PRT
<213> ORGANISM: Homo sapien

<400> SEQUENCE: 7

Gly Gln Pro Arg Glu Pro Gln Val Tyr Thr Ser Pro Pro Ser Arg Asp
1               5                   10                  15

Glu Leu Thr Lys Asn Gln Val Ser Leu Arg Cys His Val Lys Gly Phe
                20                  25                  30

Tyr Pro Ser Asp Ile Ala Val Glu Trp Glu Ser Asn Gly Gln Pro Glu
             35                  40                  45

Asn Asn Tyr Lys Thr Thr Lys Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 8
<211> LENGTH: 107
<212> TYPE: PRT
<213> ORGANISM: Artificial
<220> FEATURE:
<223> OTHER INFORMATION: Modified amino acid sequence of the monomeric, -continued disulfide-stabilized mCH3 fragment of human IgG

<400> SEQUENCE: 8

Gly Gln Cys Arg Glu Pro Gln Val Tyr Thr Ser Pro Pro Ser Arg Asp
1               5                   10                  15

Glu Leu Thr Lys Asn Gln Val Ser Leu Arg Cys His Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Lys Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Cys Leu His Asn His Tyr
                85                  90                  95

Thr Gln Lys Ser Leu Ser Leu Ser Pro Gly Lys
            100                 105

<210> SEQ ID NO 9
<211> LENGTH: 205
<212> TYPE: PRT
<213> ORGANISM: Homo sapiens

<400> SEQUENCE: 9

Leu Glu Lys Cys Cys Ala Ala Ala Asp Pro His Glu Cys Tyr Ala Lys
1               5                   10                  15

Val Phe Asp Glu Phe Lys Pro Leu Val Glu Glu Pro Gln Asn Leu Ile
            20                  25                  30

Lys Gln Asn Cys Glu Leu Phe Glu Gln Leu Gly Glu Tyr Lys Phe Gln
        35                  40                  45

Asn Ala Leu Leu Val Arg Tyr Thr Lys Lys Val Pro Gln Val Ser Thr
    50                  55                  60

Pro Thr Leu Val Glu Val Ser Arg Asn Leu Gly Lys Val Gly Ser Lys
65                  70                  75                  80

Cys Cys Lys His Pro Glu Ala Lys Arg Met Pro Cys Ala Glu Asp Cys
                85                  90                  95

Leu Ser Val Phe Leu Asn Gln Leu Cys Val Leu His Glu Lys Thr Pro
            100                 105                 110

Val Ser Asp Arg Val Thr Lys Cys Cys Thr Glu Ser Leu Val Asn Gly
        115                 120                 125

Arg Pro Cys Phe Ser Ala Leu Glu Val Asp Glu Thr Tyr Val Pro Lys
    130                 135                 140

Glu Phe Asn Ala Glu Thr Phe Thr Phe His Ala Asp Ile Cys Thr Leu
145                 150                 155                 160

Ser Glu Lys Glu Arg Gln Ile Lys Lys Gln Thr Ala Leu Val Glu Leu
                165                 170                 175

Val Lys His Lys Pro Lys Ala Thr Lys Glu Gln Leu Lys Ala Val Met
            180                 185                 190

Asp Asp Phe Ala Ala Phe Val Glu Lys Cys Cys Lys Ala
        195                 200                 205

<210> SEQ ID NO 10
<211> LENGTH: 618
<212> TYPE: PRT
<213> ORGANISM: Homo sapiens

<400> SEQUENCE: 10

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415
```

-continued

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile
610                 615

<210> SEQ ID NO 11
<211> LENGTH: 542
<212> TYPE: PRT
<213> ORGANISM: Homo sapiens

<400> SEQUENCE: 11

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
            290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys
            530                 535                 540

<210> SEQ ID NO 12
<211> LENGTH: 522
<212> TYPE: PRT
<213> ORGANISM: Homo sapiens

<400> SEQUENCE: 12

Met Ser Ser Ser Ser Trp Leu Leu Leu Ser Leu Val Ala Val Thr Ala

-continued

```
1               5                   10                  15
Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
            50                  55                  60

Ala Gly Asp Lys Trp Ser Ala Phe Leu Lys Glu Gln Ser Thr Leu Ala
65                      70                  75                  80

Gln Met Tyr Pro Leu Gln Glu Ile Gln Asn Leu Thr Val Lys Leu Gln
                    85                  90                  95

Leu Gln Ala Leu Gln Gln Asn Gly Ser Ser Val Leu Ser Glu Asp Lys
                100                 105                 110

Ser Lys Arg Leu Asn Thr Ile Leu Asn Thr Met Ser Thr Ile Tyr Ser
                115                 120                 125

Thr Gly Lys Val Cys Asn Pro Asp Asn Pro Gln Glu Cys Leu Leu Leu
                130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
                180                 185                 190

Ala Asn His Tyr Glu Asp Tyr Gly Asp Tyr Trp Arg Gly Asp Tyr Glu
                195                 200                 205

Val Asn Gly Val Asp Gly Tyr Asp Tyr Ser Arg Gly Gln Leu Ile Glu
                210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
                260                 265                 270

Arg Phe Trp Thr Asn Leu Tyr Ser Leu Thr Val Pro Phe Gly Gln Lys
                275                 280                 285

Pro Asn Ile Asp Val Thr Asp Ala Met Val Asp Gln Ala Trp Asp Ala
                290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
                355                 360                 365

Phe Leu Thr Ala His His Glu Met Gly His Ile Gln Tyr Asp Met Ala
                370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430
```

```
Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
        450                 455                 460

Lys Gly Glu Ile Pro Lys Asp Gln Trp Met Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln
            515                 520

<210> SEQ ID NO 13
<211> LENGTH: 45
<212> TYPE: PRT
<213> ORGANISM: Artificial Sequence
<220> FEATURE:
<223> OTHER INFORMATION: Synthetic- Consensus Albumin Binding Domain
      (ABDCon)

<400> SEQUENCE: 13

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
                20                  25                  30

Glu Gly Val Asn Ala Leu Lys Asp Glu Ile Leu Lys Ala
            35                  40                  45

<210> SEQ ID NO 14
<211> LENGTH: 18
<212> TYPE: PRT
<213> ORGANISM: Artificial Sequence
<220> FEATURE:
<223> OTHER INFORMATION: Synthetic - Consensus Albumin Binding Domain
      (ABDCon)

<400> SEQUENCE: 14

Gly Gly Ser Ser Arg Ser Ser Ser Ser Gly Gly Gly Gly Ser Gly Gly
1               5                   10                  15

Gly Gly

<210> SEQ ID NO 15
<211> LENGTH: 12
<212> TYPE: PRT
<213> ORGANISM: Homo sapiens

<400> SEQUENCE: 15

Glu Pro Lys Ser Cys Asp Lys Thr His Thr Cys Pro
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic- (Modified Hinge Region)

<400> SEQUENCE: 16

Lys Cys His Trp Glu Cys Arg Gly Cys Arg Leu Val Cys
1               5                   10
```

SOLUBLE ACE2 VARIANTS AND USES THEREFOR

CROSS-REFERENCE TO RELATED PATENT APPLICATIONS

The present application claims the benefit of priority under 35 U.S.C. § 119(e) to U.S. Provisional Application No. 63/130,039, filed on Dec. 23, 2020 and to U.S. Provisional Application No. 62/981,924, filed on Feb. 26, 2020, the contents of which are incorporated herein by reference in their entireties.

SEQUENCE LISTING

A replacement Sequence Listing for the original Sequence Listing filed on Feb. 26, 2021 accompanies this application and is submitted as an ASCII text file named "702581_01916_ST25.txt" which is 46 KB in size and was created on Jul. 13, 2021. The replacement Sequence Listing is electronically submitted via EFS-Web with the application and is incorporated herein by reference in its entirety.

BACKGROUND

The present disclosure relates to angiotensin converting enzyme 2 (ACE2) and variants of ACE2 for treating and/or preventing infection by certain viruses (i.e., viruses, e.g., coronaviruses, that utilize ACE2 as a receptor) in a subject in need thereof. Disclosed variants of ACE2 may include fragments of ACE2 or fusion proteins thereof that have ACE2 biological activity for binding to relevant viruses, and particularly to a coronavirus, more particularly to sudden acute respiratory syndrome coronavirus 2 (SARS-CoV-2). Disclosed variants of ACE2 may be useful for treating conditions that include but are not limited to coronavirus infection.

SUMMARY

The present disclosure provides various insights relating to and strategies for using soluble ACE2 variant polypeptide agents for treatment (e.g., prophylactic and/or therapeutic) of viral infection (i.e., for infection by viruses that use ACE2 as a receptor, specifically including coronaviruses and most particularly SARS-CoV-2). Among other things, the present disclosure provides methods of treatment. Moreover, the present disclosure provides various soluble ACE2 variant receptor polypeptide agents, and various insights relating to particularly useful such agents and/or contexts in which they are or may be most applicable.

For example, the present disclosure provides certain extended-duration-of-action variants and teaches beneficial features thereof. The present disclosure also provides certain small-molecular-size variants (e.g., small enough to be amenable to glomerular filtration) and teaches beneficial features thereof. Of particular interest are variants that are both extended-duration of action and small-molecular size as well as enhancements to increase the binding capacity of SARS-CoV-2 to the ACE2 receptor.

Disclosed herein are variants of ACE2, pharmaceutical compositions comprising the variants of ACE2, and treatment and prevention methods for coronavirus infection in a subject in need thereof, including but not limited to infection by sudden acute respiratory syndrome coronavirus 2 (SARS CoV-2). Disclosed variants of ACE2 may include polypeptide fragments of ACE2 and fusion proteins thereof that comprise a binding site for the SARS-CoV-2 receptor binding domain. The variants of ACE2 preferably are soluble. Disclosed fusion proteins may comprise ACE2 or a fragment thereof fused to an exogenous polypeptide. Preferably, the exogenous polypeptide portion of the fusion polypeptide extends the duration of action of the ACE2 variant in plasma and organs, such as lungs, of a subject who has been administered the fusion polypeptide. In some embodiments, the exogenous polypeptide portion of the fusion polypeptide extends the duration of action of the ACE2 variant by increasing the half-life of the ACE2 variant in plasma and organs, such as lungs, of a subject who has been administered the fusion polypeptide. In disclosed methods, the subject is administered the variant of ACE2 or a pharmaceutical composition comprising the variant of ACE2 in a suitable pharmaceutical carrier.

Subjects suitable for the disclosed methods of treatment may include subjects having or at risk for developing coronavirus infection.

Disclosed pharmaceutical compositions optionally may be formulated for pulmonary delivery, for example, via an aerosol or through administration via a nebulizer.

BRIEF DESCRIPTION OF THE DRAWINGS

FIG. 5. Illustrative scheme of coronavirus (CoV) spike protein (S) binding its surface receptor, the full-length ACE2, and soluble ACE2 competing for binding to coronavirus and intercepting the coronavirus from binding the ACE2 surface receptor.

The binding affinity of the ACE2 variant 618-DDC-ABD is markedly higher ($EC_{50}$=158 ng/ml) as compared to that of the ACE2 1-618-ABD ($EC_{50}$=4359 ng/ml) and also higher than that of native ACE2 740 soluble protein ($EC_{50}$=352 ng/ml).

Figure 22A:
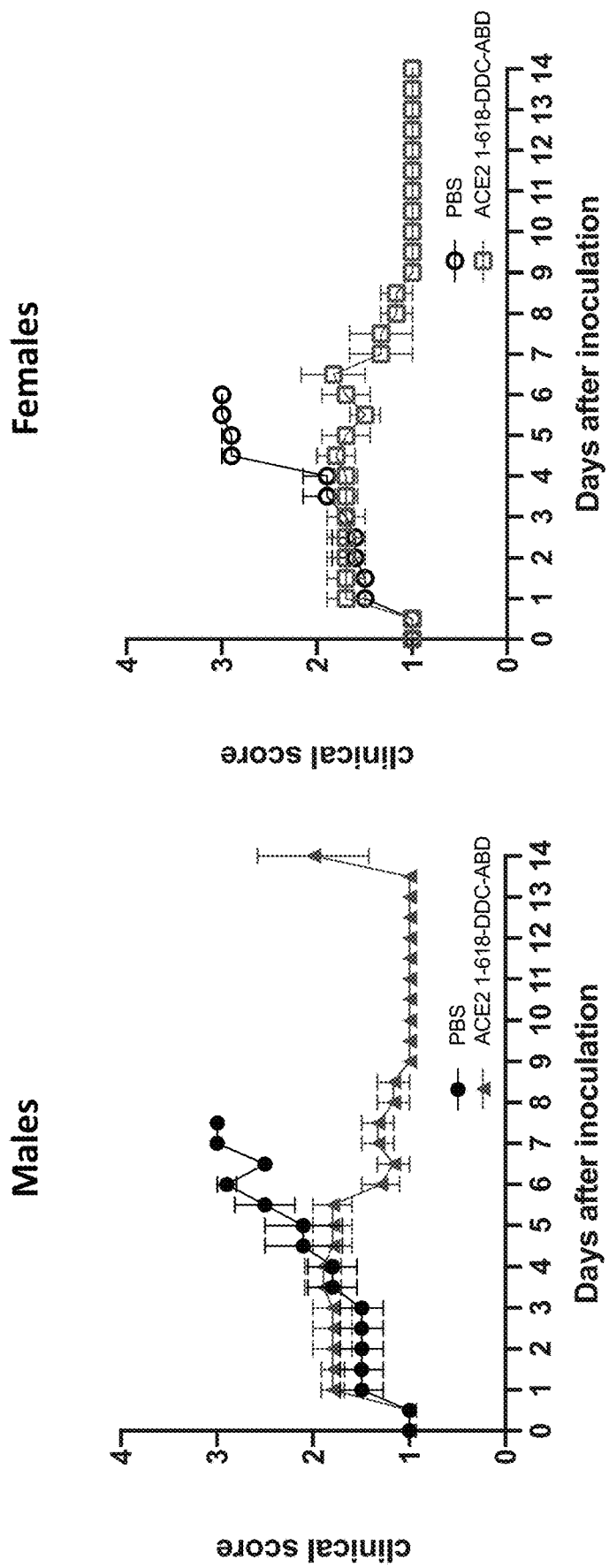
Figure 22B:
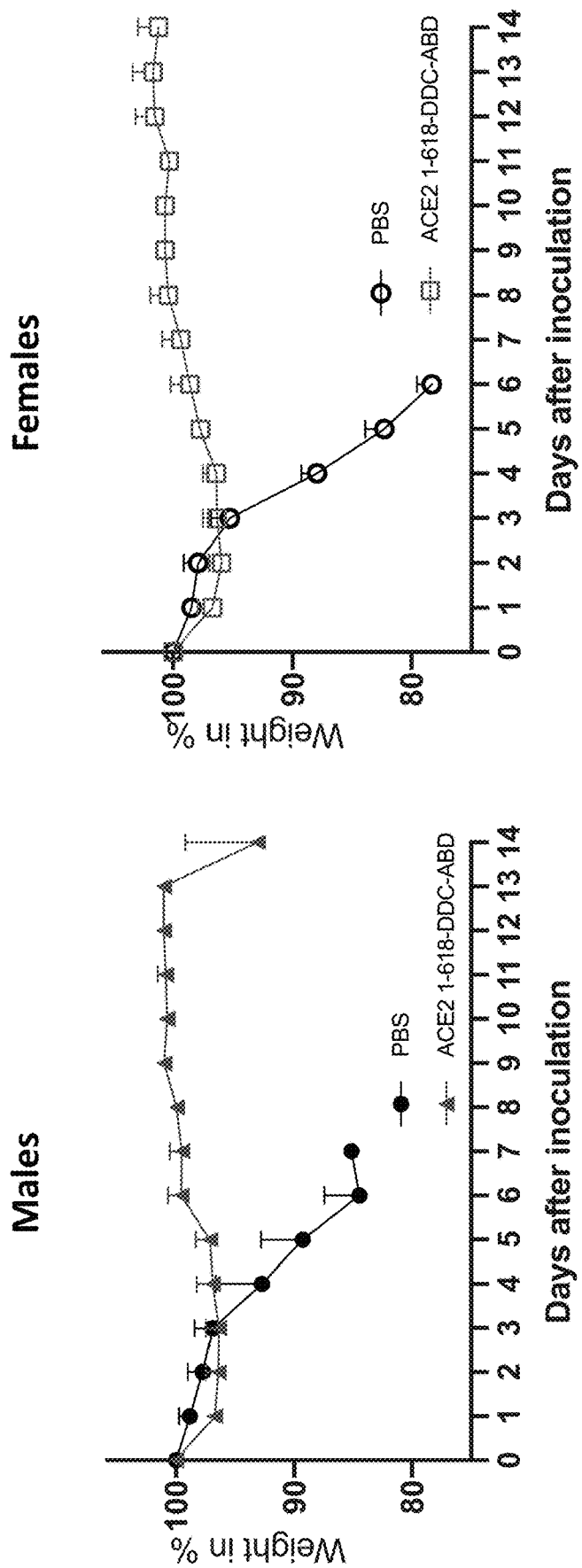
Figure 22C:
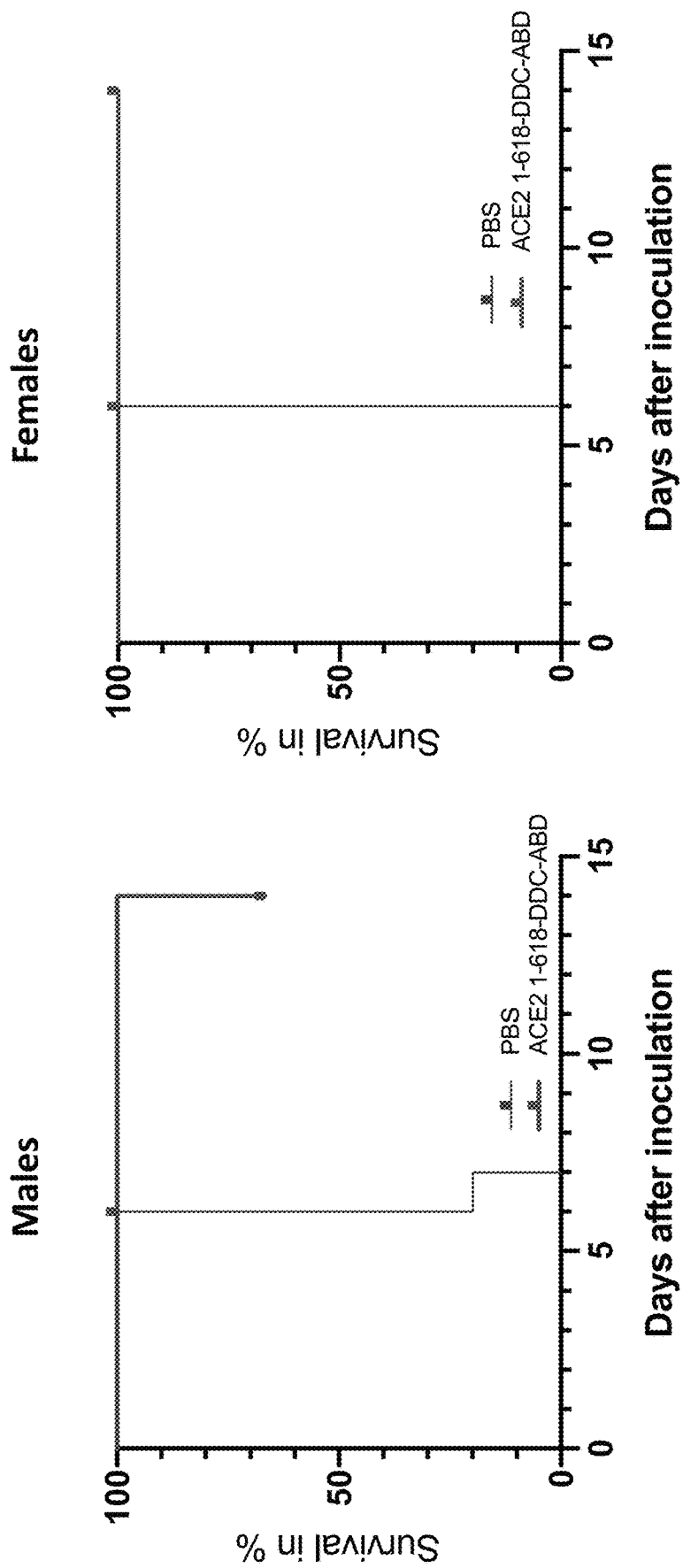

FIGS. 22(a), 22(b), and 22(c). Prevention of mortality and a marked improvement of clinical parameters after ACE2 618-DDC-ABD administration to human transgenic k18-hACE2 mice infected with SARS-CoV-2. The effect of ACE2 618-DDC-ABD was assessed on clinical score (FIG. 22(a)), body weight loss (FIG. 22(b)) and mortality prevention (FIG. 22(c)) in five k18-hACE2 transgenic male (left panels) and five female mice (right panels) as compared to vehicle-mice (PBS) infected with SARS-CoV-2 (also 5 male and 5 female mice).

Figure 23:
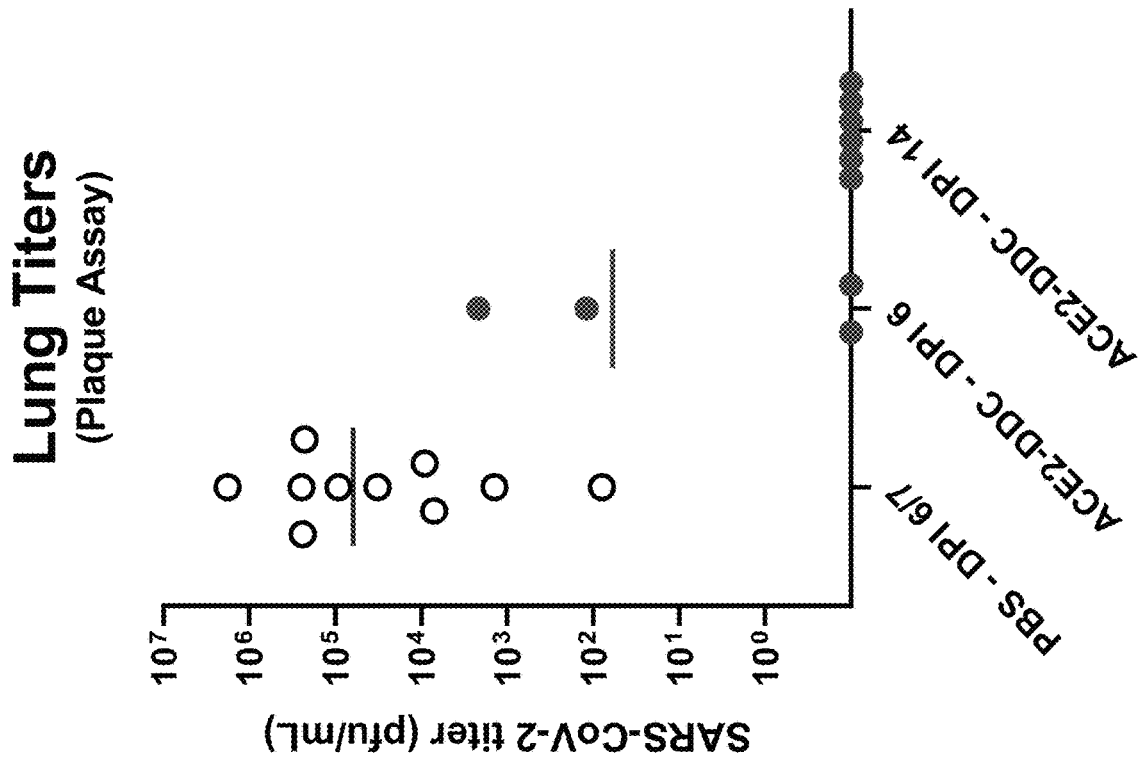

FIG. 23. Administration of ACE2 618-DDC-ABD resulted in a marked reduction of SARS-CoV-2 lung titers measured by plaque assay in k18-hACE2 mice. At 6-7 day post infection (DPI), titers were high in all untreated animals (PBS) that had to be humanely euthanized by study design. In contrast, at the same time point in 2 male and 2 female ACE2 618-DDC-ABD treated mice (DPI 6) that were healthy but were sacrificed, lung viral titers were lower or undetectable. No SARS-Cov-2 virus was detectable in the remaining k18-hACE2 mice that received ACE2 618-DDC-ABD and were sacrificed 14 days after viral inoculation (DPI 14), as per study design.

DEFINITIONS

The present invention is described herein using several definitions, as set forth below and throughout the application.

A: As used in this specification and the claims, the singular forms "a," "an," and "the" include plural forms unless the context clearly dictates otherwise. For example, the term "a polypeptide fragment" should be interpreted to mean "one or more polypeptide fragments" unless the context clearly dictates otherwise. As used herein, the term "plurality" means "two or more."

About: As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

Agent: In general, the term "agent", as used herein, is used to refer to an entity (e.g., for example, a lipid, metal, nucleic acid, polypeptide, polysaccharide, small molecule, etc, or complex, combination, mixture or system [e.g., cell, tissue, organism] thereof), or phenomenon (e.g., heat, electric current or field, magnetic force or field, etc). In some instances, as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form.

Amino acid sequence: The term "amino acid sequence" refers to an oligopeptide, peptide, polypeptide, or protein sequence (which terms may be used interchangeably), or a fragment of any of these, whether naturally occurring or synthetic. Where "amino acid sequence" refers to a sequence found in a naturally occurring protein molecule, "amino acid sequence" and like terms are not meant to limit the amino acid sequence to the complete native amino acid sequence associated with the recited protein molecule. In some embodiments, amino acid sequences contemplated herein may include one or more amino acid substitutions relative to a reference amino acid sequence. For example, a variant polypeptide may include non-conservative and/or conservative amino acid substitutions relative to a reference polypeptide. "Conservative amino acid substitutions" are those substitutions that are predicted to interfere least with the properties of the reference polypeptide. In other words, conservative amino acid substitutions substantially conserve the structure and the function of the reference protein. The following Table provides a list of exemplary conservative amino acid substitutions.

| Original Residue | Conservative Substitution |
| --- | --- |
| Ala | Gly, Ser |
| Arg | His, Lys |
| Asn | Asp, Glu, His |
| Asp | Asn, Gln |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain one or more of: (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally do not maintain one or more of: (a) the structure of the polypeptide backbone in the area of the substitution, for example, as a beta sheet or alpha helical conformation, (b) the charge or hydrophobicity of the molecule at the site of the substitution, and/or (c) the bulk of the side chain. In some embodiments, disclosed peptides may include an N-terminal esterification (e.g., a phosphoester modification) or a pegylation modification, for example, to enhance plasma stability (e.g. resistance to exopeptidases) and/or to reduce immunogenicity.

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the term "corresponding to" is understood to refer to a relationship between two or more entities. For example, the term "corresponding to" may be used to designate the position/identity of a structural element in a compound or composition relative to another compound or composition (e.g., to an appropriate reference compound or composition). For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure. Those of skill in the art will also appreciate that, in some instances, the term "corresponding to" may be used to describe an event or entity that shares a relevant similarity with another event or entity (e.g., an appropriate reference event or entity). To give but one example, a gene or protein in one organism may be described as "corresponding to" a gene or protein from another organism in order to indicate, in some embodiments, that it plays an analogous role or performs an analogous function and/or that it shows a particular degree of sequence identity or homology, or shares a particular characteristic sequence element.

Deletion: A "deletion" refers to a change in a reference amino acid sequence (e.g., SEQ ID NO:1 or SEQ ID NO:2) that results in the absence of one or more amino acid residues. A deletion removes at least 1, 2, 3, 4, 5, 10, 20, 50, 100, or 200 amino acids residues or a range of amino acid residues bounded by any of these values (e.g., a deletion of 5-10 amino acids). A deletion may include an internal deletion or a terminal deletion (e.g., an N-terminal truncation or a C-terminal truncation of a reference polypeptide). A "variant" of a reference polypeptide sequence may include a deletion relative to the reference polypeptide sequence. For example, SEQ ID NO:3 (amino acids 1-619), SEQ ID NO:4 (amino acids 1-605), SEQ ID NO:10 (amino acids 1-618), SEQ ID NO:11 (amino acids 1-542), and SEQ ID NO:12 (amino acids 1-522) include C-terminal deletions relative to reference sequence SEQ ID NO:1 (amino acids 1-805).

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been subjected to a manipulation, so that its genetic, epigenetic, and/or phenotypic identity is altered relative to an appropriate reference cell such as otherwise identical cell that has not been so manipulated In some embodiments, an engineered cell is one that has been manipulated so that it contains and/or expresses a particular agent of interest (e.g., a protein, a nucleic acid, and/or a particular form thereof) in an altered amount and/or according to altered timing relative to such an appropriate reference cell. As is common practice and is understood by those in the art, progeny of an engineered polynucleotide or cell are typically still referred to as "engineered" even though the actual manipulation was performed on a prior entity.

Fragment: A "fragment" is a portion of an amino acid sequence which is identical in sequence to but shorter in length than a reference sequence (e.g., SEQ ID NO:1 or SEQ ID NO:2). A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, or 500 contiguous amino acid residues of a reference polypeptide; or a fragment may comprise no more than 5, 10, 15, 20, 25, 30, 40, 50, 60, 70, 80, 90, 100, 150, 250, or 500 contiguous amino acid residues of a reference polypeptide; or a fragment may comprise a range of contiguous amino acid residues of a reference polypeptide bounded by any of these values (e.g., 40-80 contiguous amino acid residues). Fragments may be preferentially selected from certain regions of a molecule. The term "at least a fragment" encompasses the full length polypeptide. A "variant" of a reference polypeptide sequence may include a fragment of the reference polypeptide sequence. For example, SEQ ID NO:3 (amino acids 1-619), SEQ ID NO:4 (amino acids 1-605), SEQ ID NO:10 (amino acids 1-618), SEQ ID NO:11 (amino acids 1-542), and SEQ ID NO:12 (amino acids 1-522) comprise fragments of reference sequence SEQ ID NO:1 (amino acids 1-805).

Fusion polypeptide: A "fusion polypeptide" refers to a polypeptide comprising at the N-terminus, the C-terminus, or at both termini of its amino acid sequence a heterologous (i.e., exogenous) amino acid sequence, for example, a heterologous amino acid sequence that extends the duration of action of the fusion polypeptide extends the duration of action of the ACE2 variant in plasma and organs, such as lungs, of a subject who has been administered the fusion polypeptide. In some embodiments, the heterologous or exogenous amino acid sequence extends the duration of action of the fusion polypeptide by increasing the half-life of the fusion polypeptide in plasma and organs, such as lungs, of a subject who has been administered the fusion polypeptide. A "variant" of a reference polypeptide sequence may include a fusion polypeptide comprising the reference polypeptide fused to a heterologous or exogenous sequence.

Homology: "Homology" refers to sequence similarity or, interchangeably, sequence identity, between two or more polypeptide sequences. Homology, sequence similarity, and percentage sequence identity may be determined using methods in the art and described herein.

Identity: The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 100, at least 150, at least 200, at least 250, at least 300, at least 350, at least 400, at least 450, at least 500, at least 550, at least 600, at least 650, or at least 700 contiguous amino acid residues; or a fragment of no more than 15, 20, 30, 40, 50, 100, 150, 200, 250, 300, 350, 400, 450, 500, 550, 600, 650, or 700 amino acid residues; or over a range bounded by any of these values (e.g., a range of 500-600 amino acid residues) Such lengths are exemplary only, and it is understood that any fragment length supported by the sequences shown herein, in the tables, figures or Sequence Listing, may be used to describe a length over which percentage identity may be measured.

Include: As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

Insertion: The words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues or a range of amino acid residues bounded by any of these values (e.g., an insertion or addition of 5-10 amino acids). A "variant" of a reference polypeptide sequence may include an insertion or addition relative to the reference polypeptide sequence.

Polypeptide: As used herein refers to a polymeric chain of amino acid moieties linked together by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, glycosylation, lipidation, methylation, pegylation, phosphorylation etc., including combinations thereof. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like. The disclosed methods, compositions, and kits may be utilized to treat a subject in need thereof. A "subject in need thereof" is intended to include a subject having or at risk for developing diseases and disorders such as coronavirus infection.

Variant: In some embodiments, a "variant" of a particular polypeptide sequence may be defined as a polypeptide sequence having at least 20% sequence identity to the particular polypeptide sequence over a certain length of one of the polypeptide sequences using blast with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides, or range of percentage identity bounded by any of these values (e.g., range of percentage identity of 80-99%).

DETAILED DESCRIPTION OF CERTAIN EMBODIMENTS

ACE2

Sudden acute respiratory syndrome coronavirus 2 (SARS CoV-2) is responsible for the recent outbreak of severe respiratory disease throughout the world. The cell receptor for SARS CoV-2 entry into host cells is the angiotensin-converting enzyme 2 (ACE2). The S1 domain of the spike protein of SARS-CoV attaches the virus to its cellular receptor ACE2 on host cells prior to fusion and entry into host cells.

Figure 5:
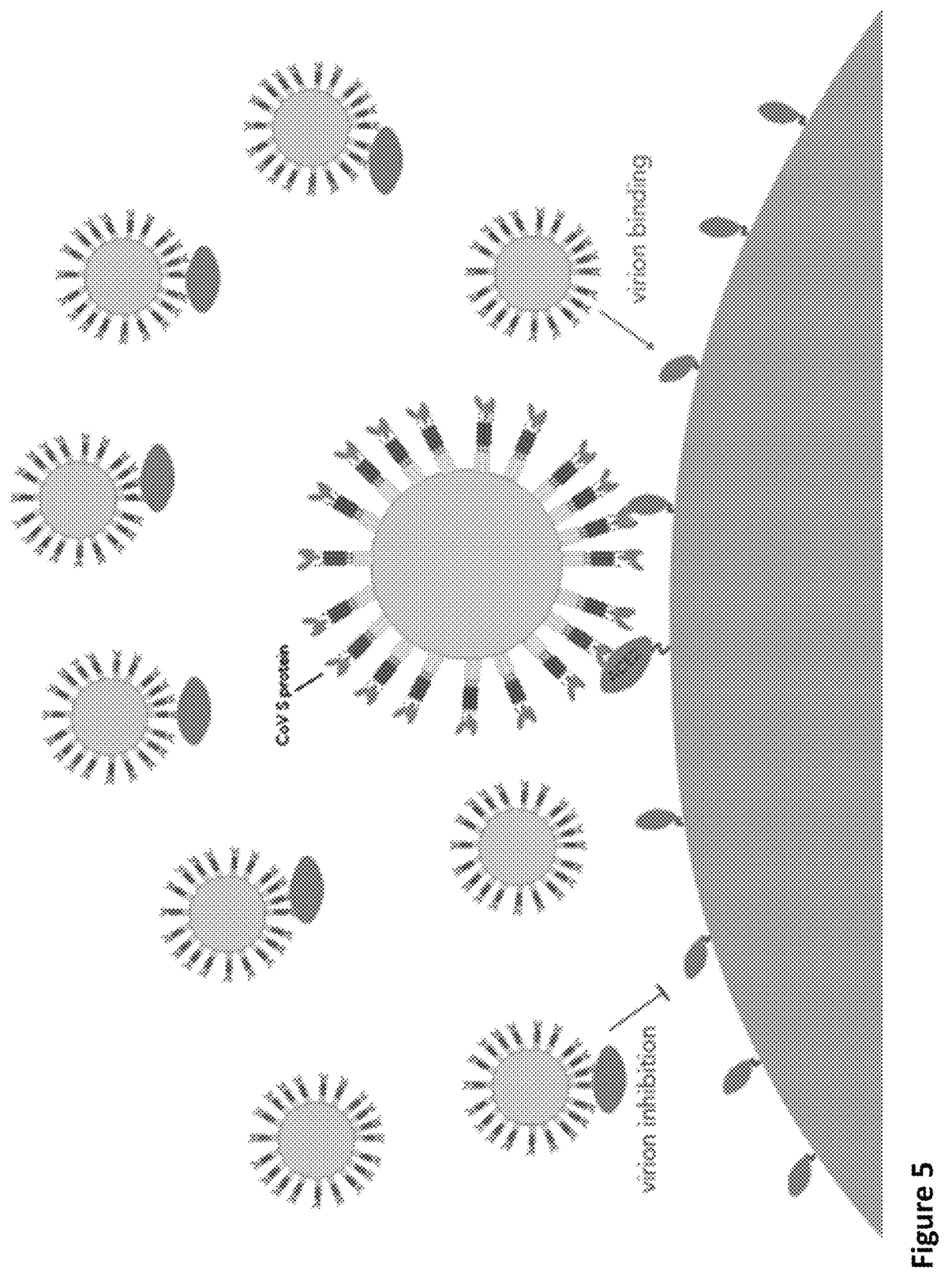

Angiotensin converting enzyme 2 (ACE2) is a monocarboxypeptidase best known for cleaving several peptides within the renin angiotensin system and other substrates such as apelin. ACE2 is present at very low levels in circulation but is widely expressed in organs, such as the kidneys and the gastrointestinal tract. In the lungs, ACE2 is more restricted to type II pneumocytes, which are considered an important entry site for SARS-CoV-2. Functionally, there are two forms of ACE2. The full-length ACE2 contains a structural transmembrane domain, which anchors an extracellular domain to the plasma membrane. The extracellular domain has been demonstrated as a receptor for the spike (S) protein of SARS CoV-2 and SARS CoV-1. The soluble form of ACE2 lacks the membrane anchor and circulates in small amounts in the blood. This soluble form of ACE2 can act as a competitive interceptor of SARS CoV-2, SARS CoV-1, and other coronaviruses by preventing binding of the viral particle to the surface-bound, full-length ACE2. In this context, provision of soluble recombinant human ACE2 proteins could be beneficial as a novel biologic therapeutic to combat or limit infection progression caused by coronaviruses that utilize ACE2 as a receptor. (See FIG. 5).

The present disclosure provides various strategies for using soluble ACE2 variant polypeptide agents for treatment (e.g., prophylactic and/or therapeutic) of viral infection (i.e., for infection by viruses that use ACE2 as a receptor, specifically including coronaviruses and most particularly SARS-CoV-2). Among other things, the present disclosure provides methods of treatment. Moreover, the present disclosure provides various soluble ACE2 variant receptor polypeptide agents, and various insights relating to particularly useful such agents and/or contexts in which they are or may be most applicable.

For example, the present disclosure provides certain extended-duration-of-action variants and teaches beneficial features thereof. The present disclosure also provides certain small-molecular-size variants (e.g., small enough to be amenable to glomerular filtration) and teaches beneficial features thereof. Of particular interest are variants that are both extended-duration of action and small-molecular size.

Disclosed methods of treatment and pharmaceutical compositions utilize and/or include angiotensin converting enzyme 2 (ACE2) or variants thereof such as fragments of ACE2. The nucleotide sequence of the human ACE2 gene is available, for example, from the National Center for Biotechnology Information of the National Institutes of Health. The location of the human ACE2 gene is provided as NC_000023.11 (15494525.15602069, complement). ACE2, isoform 1, is a transmembrane protein which is expressed first as a precursor polypeptide having the amino acid sequence set forth in SEQ ID NO:1. The mouse (Mus musculus) homolog of ACE2 has the amino acid sequence set forth in SEQ ID NO:2.

ACE2 is naturally produced with a leader polypeptide, that is cleaved in production of mature protein. Reports have described amino acids 1-17 of the precursor ACE2 polypeptide as corresponding to the a leader peptide which is cleaved from mature ACE2; amino acids 18-740 have been described as extracellular. Amino acids 741-761 have been said to form a helical transmembrane sequence. Amino acids 762-805 have been described as cytoplasmic. Those skilled in the art will appreciate that the exact number of amino acids in any of these portions (e.g., leader peptide, extracellular, transmembrane, cytoplasmic) may vary from these, and will readily be able to determine appropriate corresponding residues, for example using standard sequence comparison and/or assessment technologies.

Natural variants of ACE2 are contemplated herein and may include the natural variant K26R and the natural variant N638S. Natural isoforms of ACE2 also are contemplated herein include isoform 2 and the differences of its amino acid sequence relative to the amino acid sequence of isoform 1: F555L and/or Δ556-805. Variants of ACE2 disclosed herein, including fragments of ACE2, may have or lack one or more of these amino acid sequences of ACE2.

Among the enzymatic activities that characterize ACE2 is a carboxypeptidase activity conversion of angiotensin I to angiotensin 1-9, a protein of unknown function, and catalyzes the conversion of angiotensin II (1-8) to angiotensin (1-7) (EC:3.4.17.23), which is a vasodilator. ACE2 also catalyzes the hydrolysis of apelin-13 and dynorphin-13. Variants of ACE2 disclosed herein, including fragments of ACE2, may have or lack one or more of these enzymatic activities of ACE2.

In catalyzing the conversion of angiotensin II (1-8) to angiotensin (1-7), ACE2 catalyzes the following reaction: angiotensin II (1-8)+$H_2O$=angiotensin (1-7)+L-phenylalanine, which removes the C-terminal phenylalanine of angiotensin II (1-8). ACE2 has cofactor binding sites for $Zn^{2+}$ and $Cl^-$. The Michaelis constants ($K_m$) for these reactions are as follows: $K_m$=6.9 μM for angiotensin I; $K_m$=2 μM for angiotensin II; $K_m$=6.8 μM for apelin-13; and $K_m$=5.5 μM for dynorphin-13. The optimum pH for these reactions is 6.5 in the presence of 1 M NaCl, but ACE2 is active at pH 6-9. ACE2 is activated by halide ions chloride and fluoride, but not bromide. ACE2 is inhibited by MLN-4760, cFP_Leu, and EDTA, but not by the ACE inhibitors linosipril, captopril and enalaprilat. In some embodiments,variants of ACE2 disclosed herein, including fragments of ACE2, may have or lack one or more of these enzymatic activities of ACE2. In some embodiments, variants of ACE2 disclosed herein, including fragments of ACE2, may have a Michaelis constant for one or more of the reactions above which is ±50% of the Michaelis constant for ACE2.

ACE2 also is the cellular receptor for sudden acute respiratory syndrome (SARS) coronavirus/SARS-CoV and human coronavirus NL63/HCoV-NL63. Variants of ACE2 disclosed herein, including fragments of ACE2, may have biological activities that include binding to coronavirus.

ACE2 exhibits molecular functions and enzymatic functions that may include, for example: carboxypeptidase activity, endopeptidase activity, glycoprotein binding activity, metallocarboxypeptidase activity, cleavage of Angiotensin II, zinc ion binding activity, and binding to the coronavirus (e.g., SARS CoV-2) as a receptor for the coronavirus. Variants of ACE2 disclosed herein, including fragments of ACE2, may have at least one, and in some embodiments preferably all, of these molecular and enzymatic functions of ACE2.

ACE2 regulates biological processes that may include, for example: angiotensin catabolism processes in blood, angiotensin maturation processes, angiotensin-mediated drinking behavior processes, positive regulation of cardiac muscle contraction processes, positive regulation of gap junction assembly processes, positive regulation of reactive oxygen species metabolism processes, receptor biosynthesis processes, receptor-mediated virion attachment processes (e.g., coronaviruses), regulation of cardiac conduction processes, regulation of cell proliferation processes, regulation of cytokine production processes, regulation of inflammatory response processes, regulation of systemic arterial blood pressure by renin-angiotensin processes, regulation of vasoconstriction processes, regulation of vasodilation processes, tryptophan transport processes, and viral entry into host cell processes (e.g., coronaviruses). Variants of ACE2 disclosed herein, including fragments of ACE2, may regulate or may fail to regulate one or more of these biological processes.

Various structural features of ACE2, some or all of which may be included in ACE2 variants provided by and/or utilized in accordance with the present disclosure may include one or more of the following: amino acid position 169—chloride binding site; amino acid position 273—substrate binding site; amino acid position 345 substrate binding site; amino acid position 346—substrate binding site via a carbonyl oxygen; amino acid position 371—substrate binding site; amino acid position 374—metal binding site (e.g., $Zn^{2+}$); amino acid position 375—active site; amino acid position 378—catalytic metal binding site (e.g. $Zn^{2+}$); amino acid position 402—catalytic metal binding site (e.g. $Zn^{2+}$); amino acid position 477—chloride binding site; amino acid position 481—chloride binding site; amino acid position 505—active site; and amino acid position 515 substrate binding site. In some embodiments, a variant of ACE2 disclosed herein, including a fragment of ACE2, may have or lack one or more of these structural features of ACE2.

Alternatively or additionally, structural features of ACE2, some or all of which may be included in ACE2 variants provided by and/or utilized in accordance with the present disclosure may include one or more of the following: amino acid positions 23-52—helix; amino acid positions 56-77; amino acid positions 78-82—turn; amino acid positions 85-87—helix; amino acid positions 91-100—helix; amino acid positions 104-107—helix; amino acid positions 110-129—helix; amino acid positions 131-134—beta strand; amino acid positions 137-143—beta strand; amino acid positions 144-146—turn; amino acid positions 148-154—helix; amino acid positions 158-171—helix; amino acid positions 173-193—helix; amino acid positions 196-198—beta strand; amino acid positions 199-204—helix; amino acid positions 205-207—turn; amino acid positions 213-215—turn; amino acid positions 220-251—helix; amino acid positions 253-255—turn; amino acid positions 258-260—beta strand; amino acid positions 264-266—helix; amino acid positions 267-271—beta strand; amino acid positions 279-282—helix; amino acid positions 284-287—turn; amino acid positions 294-297—turn; amino acid positions 298-300—helix; amino acid positions 304-316—helix; amino acid positions 317-319—turn; amino acid positions 327-330—helix; amino acid positions 338-340—beta strand; amino acid positions 347-352—beta strand; amino acid positions 355-359—beta strand; amino acid positions 366-384—helix; amino acid positions 385-387—turn; amino acid positions 390-392—helix; amino acid positions 400-413—helix; amino acid positions 415-420—helix; amino acid positions 422-426—turn; amino acid positions 432-446—helix; amino acid positions 449-465—helix; amino acid positions 466-468—beta strand; amino acid positions 473-483—helix; amino acid positions 486-488—beta strand; amino acid positions 499-502—helix; amino acid positions 504-507—helix; amino acid positions 514-531—helix; amino acid positions 532-534—turn; amino acid positions 539-541—helix; amino acid positions 548-558—helix; amino acid positions 559-562—turn; amino acid positions 566-574—helix; amino acid positions 575-578—beta strand; amino acid positions 582-598—helix; amino acid positions 600-602—beta strand; and amino acid positions 607-609—beta strand. In some embodiments, a variant of ACE2 disclosed herein, including a fragment of ACE2, may have or lack one or more of these structural features of ACE2.

Still further alternatively or additionally, structural features of ACE2, some or all of which may be included in ACE2 variants provided by and/or utilized in accordance with the present disclosure may include one or more of the following amino acid modifications: amino acid position 53—N-linked glycosylation; amino acid position 90—N-linked glycosylation; amino acid position 103—N-linked glycosylation; amino acid positions 133←→141—disulfide bond; amino acid position 322—N-linked glycosylation; amino acid positions 344←→361—disulfide bond; amino acid position 432—N-linked glycosylation; amino acid positions 530←→542; amino acid position 546—N-linked glycosylation; and amino acid position 690—N-linked glycosylation. In some embodiments, a variant of ACE2 disclosed herein, including a fragment of ACE2, may have or lack one or more of these amino acid modifications of ACE2 and/or may lack the amino acids thusly modified.

It is noted that ACE2 is known to comprise 3 disulfide bonds C133-C141, C344-C361, C530-C542. There are also non-disulfide Cysteines at C261 and C498. Because truncates 1-605, 1-619 and 1-618 are enzymatically active and 1-522 is not active and because the most distal residue seen to contact the active site is Y515, the third disulfide may be essential to enzyme activity. Internal ACE2 disulfides are calculated to contribute significantly to CoV-2 spike protein binding to ACE2 where the most distal ACE2 amino acids interacting with CoV-2 RBD (also SARS-RBD) are residues 351-357, within the second disulfide loop. This CoV-2 binding segment is far from (more than 170 aa proximal) the most distal disulfide, thus less likely to be affected by the latter, which may be dispensable for CoV-2 binding activity for shorter truncated ACE2 (ACE2 variants having a molecular weight less than about 55 kD). As such, ACE2 variants having a molecular weight of less than about 55 kD are contemplated herein and may be utilized as described herein to bind and intercept SARS-CoV-2 and other viruses that use ACE2 as the receptor for cell entry.

Provided ACE2 Variants

The present disclosure provides and/or utilizes certain variants of ACE2, and particularly of human ACE2. Provided variants are preferably soluble. Provided variants preferably bind (e.g., retain binding to) a virus (e.g., a coronavirus such as SARS-CoV-2) or component thereof (e.g., that is involved in infectivity, for example by interaction with ACE2 as a cellular receptor); many embodiments, provided variants specifically bind to a coronaviral spike protein (e.g., the S1 protein of SARS-CoV-2). Provided variants preferably interfere with (e.g., compete with) viral (e.g., viral protein) interaction with membrane-associated ACE2. Thus, the present disclosure provides and/or utilizes one or more soluble human ACE2 variant polypeptide agents that can reduce viral infectivity.

In some embodiments, the present disclosure provides and/or utilizes ACE2 variants that provide (e.g., retain) one or more ACE2 protein activities (e.g., molecular and/or enzymatic activities). For example, in many embodiments, provided soluble human ACE2 variant polypeptide agents are characterized by molecular functions and/or enzymatic functions that may include, for example: carboxypeptidase activity, endopeptidase activity, glycoprotein binding activity, metallocarboxypeptidase activity, cleavage of Angiotensin II, zinc ion binding activity, and binding to the coronavirus (e.g., SARS CoV-2) as a receptor for the coronavirus; in some embodiments, ACE2 variants for use in accordance with the present disclosure are characterized by one or more, and in some embodiments by all, such activities at a level at least comparable to that of natural ACE2 (e.g., naturally produced soluble ACE2) and/or of rhACE2(1-740).

In some embodiments, variants of ACE2 disclosed herein, including fragments of ACE2, may have biological activities that include binding to coronavirus. For example, the variants of ACE2 disclosed herein preferably bind to the spike protein of SARS-CoV-2 and other coronaviruses (e.g., at the receptor binding domain (RBD)) and prevent the coronavirus from binding to the plasma membrane bound ACE2 in a competitive manner. Variants of ACE2 that bind to the spike protein of SARS CoV-2 are disclosed herein. (See also, Chan et al., "Engineering human ACE2 to optimize binding to the spike protein of SARS coronavirus," Science 369, 1261-1265 (2020), published on-line Aug. 4, 2020, the content of which is incorporated herein by reference in its entirety). As disclosed herein, variants of ACE2 that bind to the spike protein of coronavirus (e.g., SARS CoV-2) may be fused to an exogenous polypeptide to create a fusion polypeptide (e.g., an exogenous polypeptide that extends the duration of action of the fusion polypeptide in plasma of a subject that is administered the fusion polypeptide). Preferably, the variant of ACE2, such as fragments of ACE2 and/or fusion proteins comprising the fragments of ACE2, bind to the spike protein of coronavirus with a dissociation constant ($K_D$) of less than about 1000 nM, 500 nM, 100 nM, 50 nM, 40 nM, 30 nM, 20 nM, 10 nM, 5 nM, 1 nM, or lower. In some embodiments, the variant of ACE2, such as fragments of ACE2 and/or fusion proteins comprising the fragments of ACE2, bind to the receptor binding domain (RBD) of spike protein or coronavirus (e.g., amino acid 333-529 of SARS-CoV-2 S (GenBank YP_009724390.1)) with a dissociation constant ($K_D$) of less than about 1000 nM, 500 nM, 100 nM, 50 nM, 40 nM, 30 nM, 20 nM, 10 nM, 5 nM, 1 nM, or lower.

Among other things, the present disclosure provides an insight that ACE2 variants characterized both by binding and enzymatic activity are particularly useful and/or provide one or more unusual or surprising benefits for treatment of viral infection such as coronaviral infection, particularly with SARS-CoV-2.

In some embodiments, soluble ACE2 variant polypeptide agents for use in accordance with the present disclosure are or comprise a fragment (e.g., a truncation) of ACE2; alternatively or additionally, in some embodiments, provided ACE2 variants are or comprise a fusion or conjugate (e.g., a multimer) that includes an ACE2 moiety, which may be or comprise an ACE2 fragment (e.g., truncation).

In some embodiments, soluble ACE2 variant polypeptide agents for use in accordance with the present disclosure may have a maximum molecular weight or size. For example, in some embodiments, such agents may be less than about 250 kD, 225 kD, 200 kD, 175 kD, 150 kD, 125 kD, 100 kD, 95 kd, 90 kD, 85 kD, 80 kD, 75 kD, 70 kD, 65 kD, 60 kD, 55 kD, 50 kD, 45 kD, 40 kD, or 35 kD (or have a molecular weight of a range bounded by any of these values). Alternatively or additionally, in some embodiments, a provided agent may be or comprise an ACE2 fragment that is 70 kD, 65 kD, 60 kD, 55 kD, 50 kD, 45 kD, 40 kD, 35 kD, 30 kD, 25 kD, 20 kD, 15 kD, 10 kD, 5 kD or less (or have a molecular weight of a range bounded by any of these molecular weight values). Active low molecular weight variants of ACE2 are described in U.S. Publication No. 2018/0230447, the content of which is incorporated herein by reference in its entirety.

In some embodiments, soluble ACE2 variant polypeptide agents may be utilized in a non-glycosylated form. In some embodiments, glycosylated forms of disclosed ACE2 variants may exhibit a higher molecular weight than the non-glycosylated forms.

In some embodiments, ACE2 variants (e.g., soluble ACE2 variant polypeptide agents) disclosed herein, whether the ACE2 variants are glycosylated or not, may have a molecular weight of a range bounded by any of the foregoing values (e.g., 250 kD, 225 kD, 200 kD, 175 kD, 150 kD, 125 kD, 100 kD, 95 kd, 90 kD, 85 kD, 80 kD, 75 kD, 70 kD, 65 kD, 60 kD, 55 kD, 50 kD, 45 kD, 40 kD, or 35 kD, and/or 70 kD, 65 kD, 60 kD, 55 kD, 50 kD, 45 kD, 40 kD, 35 kD, 30 kD, 25 kD, 20 kD, 15 kD, 10 kD, 5 kD or less).

In some embodiments, ACE2 variants disclosed herein may be configured for use in (e.g., may be used as reference agents for comparison in) competitive binding assays for coronavirus in order to select (e.g., to identify and/or characterize) additional ACE2 variants that bind to coronavirus with different affinity, and in some cases with higher affinity. For example, provided ACE2 variants may be utilized to measure the binding affinity of additional variants of ACE2 for coronavirus. In some embodiments, relevant methods comprise contacting a variant of ACE2 with a complex comprising coronavirus bound to an immobilized form of ACE2 and determining a concentration of the ACE2 variant required to competitively bind to the coronavirus versus the immobilized form of ACE2. The immobilized variant optionally is a fragment of ACE2 (e.g., SEQ ID NO:10 (a.a. 1-618)) fused to a tag for immobilizing the variant to a solid support.

In some embodiments, an ACE2 fragment or moiety, and particularly an ACE2 moiety included in a conjugate as described herein, may contain one or more cysteine modifications. To give but a few examples, in some embodiments, cysteines 261 and/or 498 may be replaced by other amino acids, and/or tryptophan (610) and/or alanine (614) may be replaced by cysteine. Cysteine substitutions are not limited to the above listed amino acid positions.

In some embodiments, an ACE2 fragment or moiety, and particularly an ACE2 moiety included in a conjugate as described herein, may contain only a single cysteine residue. Single-cysteine moieties are particularly useful where conjugation is via a Cys SH, among other things to improve conjugate consistency and/or homogeneity. In some such embodiments, one or more cysteines that is naturally present in the ACE2 (e.g., hACE2) amino acid sequence may be substituted or removed; alternatively or additionally, cysteine may be introduced at one or more positions which do not contain cysteine in wild type ACE2 (e.g., hACE2), for example by insertion or substitution.

Fragments/Deletions

In some embodiments, ACE2 variants provided by and/or utilized in accordance with the present disclosure may be or include fragments (e.g., deletions or truncations) of ACE2, and particularly of human ACE2.

In some embodiments, ACE2 truncations for use in accordance with the present disclosure are smaller than ACE2(1-740); in some embodiments, useful ACE2 truncations are sufficiently small to be amenable to glomerular filtration; among other things, the present disclosure appreciates that soluble ACE2 variant polypeptide agents, as described herein, that are sufficiently small to be amenable to glomerular filtration, such that they can be filtered by the glomerular filtration barrier of the kidneys for better delivery, may provide particular advantages in treatment of viral infection (e.g., of coronavirus infection, specifically including SARS-CoV-2 infection), especially in certain patient populations (e.g., those who are suffering from or susceptible to acute kidney injury or glomerular damage).

In some embodiments, ACE2 truncations for use in accordance with the present disclosure may correspond to a fragment of ACE2 that comprises fewer than about 750 amino acids of ACE2, more preferably fewer than about 700, 690, 680, 670, 650, 640, 630, 620, 610 or 600 amino acids of ACE2.

In some embodiments, ACE2 truncations for use in accordance with the present disclosure may be described and/or initially produced or provided as including sequences that represent or correspond to leader sequences as described herein; those of ordinary skill in the art will readily appreciate, however, that in some embodiments, leader sequences are or can be removed. Thus, for example, where use of an "hACE2(1-618)" fragment is referenced, those skilled in the art will appreciate that, in some embodiments, a corresponding truncation lacking the leader sequence (e.g., missing approximately the first 15-20 amino acids, and in some embodiments the first 17, 18, or 19 amino acids) may be utilized.

In some embodiments, ACE2 truncations for use in accordance with the present disclosure may correspond to a 1-618 fragment of hACE2.

In some embodiments, polypeptide fragments of ACE2 for use in accordance with the present disclosure may include a deletion relative to full-length ACE2 (SEQ ID NO:1). In some embodiments, disclosed polypeptide fragments may include a deletion selected from an N-terminal deletion, a C-terminal deletion, and both, relative to full-length ACE2 (SEQ ID NO:1). In some embodiments the disclosed polypeptide fragments may include an internal deletion.

In some embodiments, a deletion may remove at least about 1, 2, 3, 4, 5, 10, 15, 20, 25, 50, 100, 150, 200 amino acids or more of full-length ACE2.

In some embodiments, a deletion removes one or more glycosylation sites, and as such, the polypeptide fragments of ACE2 may be less glycosylated than full-length ACE2, further reducing the molecular weight of the polypeptide fragments of ACE2 relative to full-length ACE2.

In some embodiments, disclosed polypeptide fragments of ACE2 may include one or more amino acid substitutions that removes a glycosylation site. In some embodiments, it may be desirable to utilize a variant of ACE2 that exhibits reduced glycosylation. Full-length, wild-type ACE2 has a molecular weight of approximately 110 kD and is a membrane protein (i.e., non-soluble).

Polypeptide fragments of ACE2 disclosed herein preferably are soluble, for example, wherein the polypeptide fragments include a C-terminal truncation related to full-length, wild-type ACE2 that removes a portion that includes the transmembrane region and optionally removes the C-terminal region.

As noted above, ACE2 is known to comprise 3 disulfide bonds C133-C141, C344-C361, C530-C542. There are also non-disulfide Cysteines at C261 and C498. Because truncates 1-605, 1-619 and 1-618 are enzymatically active and 1-522 is not active and because the most distal residue seen to contact the active site is Y515, the third disulfide may be essential to enzyme activity. Internal ACE2 disulfides are calculated to contribute significantly to CoV-2 spike protein binding to ACE2 where the most distal ACE2 amino acids interacting with CoV-2 RBD (also SARS-RBD) are residues 351-357, within the second disulfide loop. This CoV-2 binding segment is far from (more than 170 aa proximal) the most distal disulfide, thus less likely to be affected by the latter, which may be dispensable for CoV-2 binding activity for shorter truncated ACE2 (ACE2 variants having a molecular weight less than about 55 kD). As such, ACE2 truncations having a molecular weight of less than about 55 kD are contemplated for use herein, among other things to bind and intercept SARS-CoV-2 and/or other viruses that use ACE2 as the receptor for cell entry.

Notwithstanding that enzymatic activity is not required for ACE2/RBD interaction and therefore for the decoy effect of soluble ACE2 proteins that retain the binding site for RBD can achieve, such ACE2 activity is often desirable to dispose of peptides like Angiotensin II and des$^9$-arg bradykinin. Therefore, both enzymatically active and not active ACE2 truncates are contemplated herein and may be utilized as disclosed herein to bind and intercept SARS-CoV-2 and other viruses that use ACE2 as the receptor for cell entry.

Fusions/Conjugates

In some embodiments, ACE2 variants provided by and/or utilized in accordance with the present disclosure may be or include constructs in which a soluble ACE2 polypeptide (i.e., a soluble portion of an ACE2 protein) is conjugated to (i.e., covalently linked to) a stabilizing entity such that duration of action of the soluble ACE2 polypeptide is extended relative to that of the non-conjugated, "naked" parent polypeptide.

In some embodiments, a stabilizing entity may be or comprise a polypeptide, so that a provided soluble ACE2 variant polypeptide is a fusion polypeptide. Alternatively or additionally, in some embodiments, a stabilizing entity may be or comprise a non-polypeptide agent, which may in some embodiments may be a polymer (e.g., a polyethylene glycol "PEG") or comprises a polymeric portion.

In some embodiments, ACE2 polypeptide and stabilizing entity moieties are directly associated with one another; in other embodiments they may be associated via a linker.

Fusion polypeptides of ACE2 or variants thereof are disclosed herein. In some embodiments, fusion polypeptide of ACE2 or a variant thereof may include the amino acid sequence of ACE2 or a variant thereof (e.g., the amino acid sequence of a fragment of ACE2) fused to a heterologous or exogenous amino acid sequence. Preferably, the heterologous (e.g., exogenous) amino acid sequence increases duration of action of the fusion polypeptide in plasma of a subject to which such fusion polypeptide has been administered; in some embodiments, the heterologous (e.g., exogenous amino acid sequence increases half-life of the fusion polypeptide in plasma of such a subject.

Disclosed fusion polypeptides may comprise the amino acid sequence of ACE2 or a variant thereof (e.g., the amino acid sequence of a fragment of ACE2) fused directly to a heterologous (e.g., exogenous) amino acid sequence or fused via a linker sequence. In some embodiments, suitable linker sequences may include amino acid sequences of 5, 6, 7, 8, 9, 10, 11, 12, 13, 14, or 15 amino acids or more, or a range bounded by any of these values (e.g., a linker of 5-15 amino acids). In some embodiments, a linker sequence comprises only glycine residues, serine residues, and/or alanine residues.

Fusion polypeptides disclosed herein include the amino acid sequence of ACE2 or a variant thereof fused to the amino acid sequence of a heterologous (e.g., exogenous) polypeptide.

In some embodiments, the exogenous polypeptide is or comprises the ABD of streptococcal protein G or a fragment thereof, such as the C-terminal albumin binding domain 3 (ABD3) of streptococcal protein G (e.g., ABD3 from strain G148, or the ABD035 derivative (SEQ ID NO:5) or ABD-Con (SEQ ID NO:13). (See, e.g., Nilvebrant et al., *Comput. Struct. Biotechnol. J.* 6(7): 108, March 2013 and Jacobs et al., *Protein Engineering, Design and Selection*, 28(10):385-393, October 2015; the contents each of which are incorporated herein by reference in their entireties).

In some embodiments, the exogenous polypeptide is or comprises an antibody or one or more fragments of an antibody, for example, the Fc portion of an antibody (crystallizable fragment of human IgG) which in some cases is devoid of its hinge region, or is otherwise modified, to prevent dimerization of the fusion polypeptide (e.g., SEQ ID NO:6)). In other instances, dimerization may be desired, for example to enhance binding to SARS-CoV-2 receptor binding domain. Fusion of short ACE2 variants like ACE2 (1-618) with Fc (e.g., SEQ ID NO:6) or the monomeric CH3 Fc derivate (e.g., SEQ ID NO:7 or SEQ ID NO:8) can enable its delivery through a functional FcRn-dependent transport pathway in the lung endothelial cells and other tissues that can be used locally for more efficient administration in the treatment of organ injury such as lung injury.

In some embodiments, the exogenous polypeptide is or comprises serum albumin or a fragment thereof, for example domain III of human serum albumin or a fragment thereof (e.g., SEQ ID NO:9). Fusion polypeptides comprising serum albumin or a fragment thereof may exhibit one or more properties associated with serum albumin or the fragment thereof, such as increased duration of action in plasma and/or tissues (e.g., in lungs) (for example, by increasing the half-life of the fusion polypeptides).

In some embodiments, fusion polypeptides disclosed herein may include an amino acid tag sequence, for example, which may be utilized for purifying and or identifying the fusion polypeptide. Suitable amino acid tag sequences may include, but are not limited to, histidine tag sequences comprising 5-10 histidine residues. In some embodiments, such a tag sequence may itself provide or contribute to extension of duration of action (e.g., at least in part by extending half-life). Thus, in some embodiments, a heterologous polypeptide may be or comprise such tag. Alternatively, in some embodiments, a tag may not itself provide or contribute to extension of duration of action. In some embodiments, a fusion polypeptide provided by the present disclosure may comprise each of (i) an ACE2 moiety; (ii) a stabilizing moiety; and (iii) a tag moiety, and may optionally include one or more linker moieties (e.g., between two other linked moieties).

In some embodiments, a stabilizing moiety and/or a tag moiety may be linked at the N-terminus of the ACE2 moiety, at its C-terminus, or internally (without disrupting relevant activity(ies) of the ACE2 moiety). In some embodiments, stabilizing and tag moieties may be linked at different such positions. As noted herein, in some embodiments, linked moieties may be directly conjugated to one another; in other embodiments moieties may be linked with one another by way of a linker which, for example, may be or comprise a polypeptide of, for example, at least about 5, 10, 15, 20, or 25 amino acids, e.g., selected from glycine, serine, and/or alanine, such as the amino acid sequence of SEQ ID NO:14.

In some embodiments, the ACE2 variants disclosed herein are fusion proteins comprising at least a fragment of ACE2 fused to an exogenous polypeptide as disclosed herein (e.g., ABD, ABDCon, Fc). As such, the molecular weight of the exogenous protein will increase the molecular weight of the fragment of ACE2. In some embodiments, the disclosed fusion proteins, whether glycosylated or non-glycosylated, may have a molecular weight of less than about 250 kD, 225 kD, 200 kD, 175 kD, 150 kD, 125 kD, 100 kD, 95 kd, 90 kD, 85 kD, 80 kD, 75 kD, 70 kD, 65 kD, 60 kD, 55 kD, 50 kD, 45 kD, 40 kD, or 35 kD (or have a molecular weight of a range bounded by any of these values).

Other

Soluble ACE2 variant polypeptide agents provided by and/or utilized in accordance with the present disclosure may contain one or more structural features or modifications including but not limited to those described herein.

In some embodiments, disclosed ACE2 variants (e.g., ACE2 variant polypeptide agents) may include an N-terminal methionine residue that does not occur naturally in the native amino acid for ACE2. For example, the amino acid sequence of ACE2 variants contemplated herein may include an N-terminal deletion relative to the amino acid sequence of full-length ACE2, and/or may be modified to include an N-terminal methionine residue that is not present in the amino acid sequence of full-length ACE2.

Alternatively or additionally, in some embodiments, disclosed ACE2 variants (e.g., ACE2 variant polypeptide agents) may be modified so as to comprise an amino acid sequence, or modified amino acids, or non-naturally occurring amino acids, such that the disclosed ACE2 variants cannot be said to be naturally occurring. In some embodiments, the disclosed ACE2 variants are modified and the modification is selected from the group consisting of acylation, acetylation, formylation, lipolylation, myristoylation, palmitoylation, alkylation, isoprenylation, prenylation, and amidation. An amino acid in the disclosed polypeptides may be thusly modified, and in particular embodiments, the modifications may be present at the N-terminus and/or C-terminus of the polypeptides (e.g., N-terminal acylation or acetylation, and/or C-terminal amidation). In some embodiments, such modifications may enhance the stability of the polypeptides and/or make the polypeptides resistant to proteolysis.

In some embodiments, disclosed ACE2 variants variants (e.g., ACE2 variant polypeptide agents) may be modified to replace a natural amino acid residue by an unnatural amino acid. Unnatural amino acids may include, but are not limited to an amino acid having a D-configuration, an N-methyl-α-amino acid, a non-proteogenic constrained amino acid, or a β-amino acid.

In some embodiments, disclosed ACE2 variants (e.g., ACE2 variant polypeptide agents) may be modified in order to increase the stability of the ACE2 variants in plasma. For example, the disclosed peptides may be modified in order to make the peptides resistant to peptidases. In some embodiments, disclosed peptides may be modified to replace an amide bond between two amino acids with a non-amide bond. For example, the carbonyl moiety of the amide bond can be replaced by $CH_2$ (i.e., to provide a reduced amino bond: —CH2-NH—). Other suitable non-amide replacement bonds for the amide bond may include, but are not limited to: an endothiopeptide, —C(S)—NH, a phosphonamide, —P(O)OH—NH—), the NH-amide bond can be exchanged by O (depsipeptide, —CO—O—), S (thioester, —CO—S—) or $CH_2$ (ketomethylene, —CO—$CH_2$—). The peptide bond can also be modified as follows: retro-inverso bond (—NH—CO—), methylene-oxy bond (—$CH_2$—), thiomethylene bond (—$CH_2$—S—), carbabond (—$CH_2$—$CH_2$—), hydroxyethylene bond (—CHOH—$CH_2$—) and so on, for example, to increase plasma stability of the peptide sequence (notably towards endopeptidases).

In some embodiments, disclosed ACE2 variants (e.g., ACE2 variant polypeptide agents) may include a non-naturally occurring N-terminal and/or C-terminal modification. For example, the N-terminal of the disclosed peptides may be modified to include an N-acylation or a N-pyroglutamate modification (e.g., as a blocking modification). The C-terminal end of the disclosed peptides may be modified to increase the duration of action of the ACE2 variants in plasma and/or tissue (e.g., in lungs). Disclosed peptides may be conjugated to carbohydrate chains (e.g., via glycosylation to glucose, xylose, hexose), for example, to increase plasma stability (notably, resistance towards exopeptidases).

In some embodiments, disclosed ACE2 variants (e.g., ACE2 variant polypeptide agents) may include one or more amino acid substitutions or deletions that removes a glycosylation site, and/or may lack glycosylation for some other reason (e.g., may have been produced in a non-glycosylated form).

In some embodiments, an unglycosylated form of an ACE2 variant (e.g., an ACE2 variant polypeptide agent) may have a maximum molecular weight or size. For example, in some embodiments, such non-glycosylated from may be less than about 70 kD, 65 kD, 60 kD, 55 kD, 50 kD, 45 kD, 40 kD, 35 kD, 30 kD, 25 kD, 20 kD, 15 kD, 10 kD, 5 kD or less (or have a molecular weight of a range bounded by any of these molecular weight values).

Multimerization

The present disclosure provides a particular insight that, in some embodiments, useful soluble ACE2 variant polypeptide agents in accordance with the present disclosure may be capable of multimerization. For example, the present disclosure teaches that such multimerization may facilitate and/or stabilize interaction with a virus or viral component (e.g., with a coronaviral spike protein such as a SARS-CoV-2 spike protein), which in turn may improve effectiveness of a soluble ACE2 variant polypeptide agent as a decoy to disrupt viral infectivity.

The coronavirus spike protein is produced as a precursor that is post-translationally cleaved into S1 and S2 components that remain associated with one another. Each S1 component includes an N-terminal domain (NTD), a receptor-binding domain (RBD), and associated intermediate subdomains. Infection is mediated by a spike protein trimer, whose interaction with cell-surface-associated ACE2 triggers cell entry. The present disclosure contemplates that, in some embodiments, more effective decoy action may be achieved by soluble ACE2 variant polypeptide agents that have some ability to interact with one another (i.e., to multimerize), at least when co-localized by interaction with individual RBDs of a spike protein trimer, so that the spike protein trimer-ACE2 variant polypeptide agent complex is stabilized and more effectively blocks the spike protein trimer from interacting with cell-surface-associated ACE2.

The present disclosure further contemplates, as described herein, that in some embodiments, particularly useful ACE2 variant polypeptide agents are those that are sufficiently small to be amenable to glomerular filtration. The present disclosure appreciates that multimerization, even of a small agent, may interfere with glomerular filtration. Thus, in some embodiments, multimerizing ACE2 variant polypeptide agents may not be amenable to glomerular filtration and therefore may not be particularly useful in contexts that require or especially benefit from delivery into the kidney; on the other hand, such variants may be particularly effective as decoy agents and thus especially useful where such decoy activity is paramount.

In some particular embodiments, a soluble ACE2 variant polypeptide variant useful in accordance with the present disclosure, and/or a composition that comprises or delivers it, may be engineered to remain in a monomeric state when present in serum and not bound to a spike protein trimer, while having sufficient multimerization capacity at the high local concentration achieved through co-localization by interaction with individual spike RBDs within a spike protein trimer to provide enhanced stability to the trimeric complex and/or otherwise improve decoy action.

Moreover, in some embodiments, soluble ACE2 variant polypeptide variant useful in accordance with the present disclosure may comprise covalently-linked multimers of individual ACE2 moieties. See, for example, Example 6. It is expected that such multimers may be particularly effective in blocking viral infection. See, for example, Bracken C. J. et al., 2020. Bi-paratopic and multivalent VH domains block ACE2 binding and neutralize SARS-CoV-2. *Nat Chem Biol* doi.org/10.1038/s41589-020-00679-1, which reports that potent enhancement of the blocking of CoV-2 virus infection, >1000-fold can be achieved when RBD-binding polypeptides (10-15 kD) are fused to themselves as trimers, thus simultaneously occupying multiple RBD on a single spike trimer in their tethered form.

Characterization

Among other things, provided soluble ACE2 variant polypeptide agents are characterized by an ability to bind to a viral protein (e.g., a coronaviral spike protein) and/or otherwise to inhibit (e.g., to compete) an interaction between such protein and membrane-associated ACE2; in some embodiments such inhibition is to a degree comparable to that observed with an appropriate positive control reference (which appropriate positive control reference may, in some embodiments, be a non-truncated soluble ACE2 polypeptide such as hACE2(1-740). In some embodiments, provided variants show dose-dependent inhibition of such interaction. In some embodiments, a provided variant may show dose-dependent inhibition that evidences interaction (e.g., multimerization) between or among individual variant polypeptides; in some such embodiments, such interaction (e.g., multimerization) occurs at elevated local concentrations achieved at virus particle surfaces (e.g., even when such variant may be otherwise present in a relevant bodily fluid [e.g., serum] at a concentration sufficiently low that no such multimerization is observed absent virus particles).

In some embodiments, a provided soluble ACE2 variant polypeptide agent is characterized by an ability to inhibit SARS-CoV-2 infection as assessed in an appropriate model system; in some embodiments such inhibition is to a degree comparable to that observed with an appropriate positive control reference (which appropriate positive control reference may, in some embodiments, be a non-truncated soluble ACE2 polypeptide such as hACE2(1-740). In some embodiments, a provided soluble ACE2 variant polypeptide agent is characterized by an ability to inhibit SARS-CoV-2 infection of human kidney organoids.

In some embodiments, a provided soluble ACE2 variant polypeptide agent may be characterized by catalytic efficiency (e.g., cleavage of a substrate such as Ang II-(1-8) and/or des-9Arg-Bradykinin (bradykinin-(1-8), which may, in some embodiments, be determined, for example via a phenylalanine assay as described herein) that is comparable to that observed with an appropriate reference ACE2 polypeptide (e.g., a parent soluble ACE2(1-740)).

In some embodiments, a provided soluble ACE2 variant polypeptide agent may be characterized by blood pressure-lowering effect during acute Ang II infusion (e.g., as may be assessed in a rodent such as a mouse) that is comparable to that observed with an appropriate reference ACE2 polypeptide (e.g., a parent soluble ACE2(1-740)).

In some embodiments, a provided soluble ACE2 variant polypeptide agent may be characterized by increased serum Cmax when compared with an appropriate reference ACE2 polypeptide (e.g., a parent soluble ACE2(1-740)). In some embodiments, a provided soluble ACE2 variant polypeptide agent may be characterized by a serum Cmax that is approximately twice that of such reference, or even more.

In some embodiments, a provided soluble ACE2 variant polypeptide agent may be characterized by prolonged in vivo activity when compared with an appropriate reference ACE2 polypeptide (e.g., a parent soluble ACE2(1-740)). In some embodiments, an assessed in vivo activity may be or comprise a binding activity (e.g., a spike protein binding activity), a neutralization activity (e.g., inhibition of infection), an enzymatic activity (e.g., ACE2 enzymatic activity, such as may be assessed, for example, by direct cleave assay and/or by ability to reduce blood pressure during acute Ang II infusion).

In some embodiments, a provided soluble ACE2 variant polypeptide agent may be characterized by an observed in vivo activity persistence (i.e., detectable activity above an established threshold) in a relevant assay that is at least approximately 5, 10, 15, 20, 25, 30, 35, 40, 45, 50, 55, 60, 65, 70, 75, 80, 85, 90, 95, 100 or more times that of an appropriate reference ACE2 polypeptide (e.g., a parent soluble ACE2(1-740)); alternatively or additionally at least 10, 20, 30, 40, 50, 60, 70, 80, 90, 100, 110, 120, 130, 140 days longer. In some embodiments, a provided soluble ACE2 variant polypeptide agent is characterized by persistence of one or more activities in vivo above a relevant threshold for at least about 1, 2, 3, 4, 5, 6, 7, 8, 9, 10 days or more after administration of the soluble ACE2 variant polypeptide agent, or, in some embodiments at least about 1, 2, 3, 4, 5, 6, 7, 8, 9, 10, 11, 12, 13, 14, 15, 16, 17, 18, 19, 20 weeks or more; in some embodiments, 1, 2, 3, 4, 5, 6 months or more, etc.

In some embodiments, a provided soluble ACE2 variant polypeptide that demonstrates persistence of in vivo activity as described herein may be amenable to dosing according to a regimen that includes only a single dose or a small number of doses and/or in which doses may be separated from one another by a relatively extended period of time (e.g., reflective of time of activity persistence in vivo).

In some embodiments, a provided soluble ACE2 variant polypeptide is assessed for one or more of (i) binding to virus or component (e.g., spike protein) thereof; (ii) inhibiting (e.g., competing) interaction between such virus or component thereof and hACE2 (especially hACE that is displayed on or otherwise associated with cell membranes); (iii) neutralization (e.g., inhibition) of viral infection, cytotoxicity, (iv) impact on receptor downregulation, etc., for example using one or more assays as exemplified herein and/or as would be appreciated by those skilled in the art, reading the present disclosure, to be comparably informative.

In some embodiments, a soluble ACE2 variant polypeptide is characterized relative to a particular reference. To give but a few examples, in some such embodiments, a reference may be or comprise ACE2(1-740) (e.g., hACE2 (1-740)). Alternatively or additionally, in some embodiments, a reference may be or comprise hACE2(1-618) and/or mACE2(1-619)(which may, in some embodiments, be particularly useful as a negative control). Further alternatively or additionally, in some embodiments, an agent that is specifically exemplified herein (e.g., hACE2(1-618)-ABD and/or hACE2(1-618)-Fc, etc) may be utilized as a reference. That is, the present disclosure having identified and/or documented particular attributes of such exemplified agents, and thus having demonstrated feasibility of their performance, the present disclosure further teaches their use as comparators for development or confirmation of additional useful agents, including alternative soluble ACE2 variant polypeptide agents within the scope of the present disclosure.

Viruses

Teachings of the present disclosure are applicable to infection by viruses that use or require (e.g., that bind to) ACE2 as a receptor (e.g., for cell entry). Certain coronaviruses, including SARS-CoV and SARS-CoV-2, in particular, enter cells through interaction with ACE2. See, for example, Perlan & Netland *Nature Rev Microbio* 7:439-450, May 11, 2009; Zhang et al *Intensive Care Medicine* 46:586-590, Mar. 3, 2020; Hoffman et al *Cell* 181(2):271-280.e.8. doi: 10.1016/j.cell.2020.02.052. Epub 2020 Mar. 5). It is expected that additional coronavirus strains, and potentially strains of other viruses, will also be determined to enter cells through interaction with ACE2.

Pharmaceutical Compositions

The compositions disclosed herein may include pharmaceutical compositions that comprise or deliver presently disclosed ACE2 variants and are formulated for administration to a subject in need thereof. Such compositions can be formulated and/or administered in dosages and by techniques well known to those skilled in the medical arts taking into consideration such factors as the age, sex, weight, and condition of the particular patient, and the route of administration.

Provided compositions may include pharmaceutical solutions comprising carriers, diluents, excipients, and surfactants, as known in the art. Further, such compositions may include preservatives (e.g., anti-microbial or anti-bacterial agents such as benzalkonium chloride). Provided compositions also may include buffering agents (e.g., in order to maintain the pH of the composition between 6.5 and 7.5).

Provided pharmaceutical compositions may be administered therapeutically. In therapeutic applications, such compositions are administered to a patient in an amount and/or according to a dosing regimen sufficient to elicit a therapeutic effect (e.g., a response which cures or at least partially arrests or slows or delays onset of symptoms and/or complications of disease (i.e., a "therapeutically effective dose")).

In some embodiments, a pharmaceutical composition comprises a soluble ACE2 variant polypeptide agent as described herein.

In some embodiments, a pharmaceutical composition comprises a nucleic acid that encodes (and/or that templates a nucleic acid that encodes) a soluble ACE2 variant polypeptide agent as described herein. In some such embodiments, such nucleic acid is or comprises DNA or RNA (which may include one or more non-natural residues or modifications, as is known in the art). In some such embodiments, a pharmaceutical composition is or comprises a viral nucleic acid and/or capsid (e.g., an AAV). Alternatively or additionally, in some such embodiments, a pharmaceutical composition is or comprises a lipid delivery agent (e.g., a liposome or lipid nanoparticle or other lipid-based agent as is known in the art).

Preferably, a pharmaceutical composition is formulated for parenteral or pulmonary (e.g., aerosol) administration.

In some embodiments, a pharmaceutical composition is a liquid, or is a solid (e.g., dry powder and/or frozen liquid) material amenable to conversion to a liquid for administration. In some embodiments, a pharmaceutical composition is or comprises an emulsion.

Subjects for Administration

Subjects suitable for the disclosed methods of treatment may include subjects having or at risk for developing coronavirus infection. For example, in some embodiments, subjects may have been exposed, or expect to be exposed (e.g., to be present in a high risk environment or situation) to coronavirus (e.g., SARS-CoV-2). In some embodiments, subjects may not have displayed confirmed symptoms of infection. In some embodiments, subjects may have displayed one or more confirmed symptoms of infection. In some embodiments, subjects may have been diagnosed with infection. In some embodiments, subjects may be suffering from disease. In some embodiments, subjects may be under a doctor's care with respect to infection. In some embodiments, subjects may be or have been hospitalized for the infection.

As described herein, in some embodiments, soluble ACE2 variant polypeptide agents with decoy activity are administered in prophylactic contexts (e.g., to subjects who have not developed symptoms and/or are not known to have been exposed to virus). In some embodiments, soluble ACE2 variant polypeptide agents with enzymatic activity are administered to subjects suffering from or at risk of particular tissue damage (e.g., lung and/or kidney damage). In some embodiments, soluble ACE2 variant polypeptide agents with enzymatic activity and molecular size amenable to glomerular filtration are administered to subjects suffering from or susceptible to kidney damage (e.g, disease or injury).

Routes of Administration

In some embodiments, a composition that comprises and/or delivers a soluble ACE2 variant polypeptide agent as described herein is administered via a parental (particularly intravenous, subcutaneous, and/or intramuscular) route or via a pulmonary (e.g., via aerosol and including nasal administration) route, though other routes (e.g, oral, mucosal [e.g., buccal, rectal, sublingual, vaginal]).

In some embodiments, soluble ACE2 variant polypeptide agents with decoy activity are administered via a pulmonary route, particularly if administered to subjects who do not show symptoms and/or are not known to have yet been exposed to a relevant virus. In some such embodiments, administration is via the nose or the mouth or both. In some embodiments, administration is by aerosol.

In some embodiments, soluble ACE2 variant polypeptide agents with enzymatic activity are administered parenterally, particularly if administered to subjects suffering from or particularly susceptible to tissue damage away from the lungs (e.g., kidney damage), although pulmonary delivery (e.g., via the nose or mouth or both such as by aerosol) is typically also desirable.

Dosing

Those skilled in the art will appreciate that exact dosing regimens utilized in practice of the present invention may depend on particular agent used, subject treated (e.g., age, condition, state of viral exposure and/or infection, etc).

Regardless, among other things, in some embodiments, the present disclosure provides soluble ACE2 variant polypeptide agents with extended duration of action; such agents are amenable to less frequent dosing.

In some embodiments soluble ACE2 variant polypeptide agents provided herein are dosed no more frequently than once per day. In some embodiments, dosing is no more frequent than once every 2, 3, 4, 5, 6, 7, 8, 9, or 10 days. In some embodiments, dosing is no more frequent than twice per week, once per week, once every two weeks, once a month, or less.

In some embodiments, compositions that comprise or deliver soluble ACE2 variant polypeptide agents as described herein may be self-administered, particularly via aerosol (e.g., nebulizer).

Combinations

In some embodiments, provided compositions are administered in combination with (e.g., to subjects who are receiving or have received) other therapy for treatment (e.g., prophylactic and/or therapeutic treatment) of viral infection.

In some embodiments, such other therapy may be or comprise a vaccine, and anti-viral agent, and/or an anti-inflammatory agent.

In some embodiments, such other therapy may be or comprise another agent (e.g., another decoy agent) that disrupts interaction between virus (or viral component, e.g., spike protein) and ACE2, particularly when the administered agent provides ACE2 enzymatic activity and the relevant subject(s) is suffering from tissue damage and/or is otherwise expected to benefit from enhancement of ACE2 enzymatic function. Such a combination, by providing alternative means to disrupt virus/ACE2 interaction, reduces the amount of decoy activity required of the administered ACE2 variant polypeptide agent, such that more may be available to provide ACE2 enzymatic activity.

EXEMPLIFICATION

The following Examples are illustrative and should not be interpreted to limit the scope of the claimed subject matter.

Example 1: A Novel Soluble ACE2 Variant with Prolonged Duration of Action Prevents SARS-CoV-2 Infection in Human Kidney Organoids Significance Statement The severe acute respiratory syndrome coronavirus 2 (SARS-CoV-2) has resulted in a pandemic for which currently there are limited preventative and therapeutic approaches. The present Example document use of a particular soluble ACE2 variant as a way to intercept the SARS-CoV-2 S spike from binding to the full-length membrane-bound ACE2 receptor.

We have developed a newly bioengineered soluble ACE2 variant that (i) includes an ACE2 polypeptide of shorter molecular size than natural ACE2; and (ii) is further modified by fusing the shorter ACE2 polypeptide with an ABD tag. We demonstrate moreover, that our novel soluble ACE2 variant can inhibit SARS-CoV-2 infection in an established human kidney organoids model. Human kidney organoids can be infected by SARS-CoV-2 as they possess the ACE2 receptor and the transmembrane serine protease 2. Effectiveness of our novel soluble ACE2 variant in this model, confirms its potential preventative and therapeutic use as described herein.

Abstract

Background: There is an urgent need for approaches to prevent and treat SARS-CoV-2 infection. Without wishing to be bound by any particular theory, we propose that a administration of a soluble ACE2 variant as described herein, as a decoy to bind to SARS-CoV-2, should limit viral uptake mediated by binding to membrane-bound FL-ACE2; we further propose that the particular ACE2 variant exemplified herein may provide further therapeutic benefit as a result of ensuring enzymatic ACE2 activity to affected organs in COVID-19 patients.

Methods: A short variant of human soluble ACE2 protein consisting of 618 amino acids, hACE2(1-618), was generated and fused with an albumin-binding domain using an artificial gene encoding ABDCon, which has improved albumin binding affinity relative to ABD. Human kidney organoids were used for infectivity studies of SARS-CoV-2 in a BSL-3 facility to examine the neutralizing effect of these novel ACE2 variants.

Results: Whereas plasma ACE2 activity of the naked hACE2(1-618) and hACE2(1-740) lasted about 8 hours, the hACE2(1-618-ABD) resulted in persistent substantial activity at 96 hours, and it was still biologically active 3 days after injection. Moreover, this hACE2(1-618)-ABD variant neutralized SARS-CoV-2 infection of human kidney organoids, which express ACE2 and TMPRSS2.

Conclusions: This novel hACE2(1-618)-ABD can neutralize SARS-CoV-2 infectivity in human kidney organoids. Moreover, its prolonged duration of action, for example relative to hACE2(1-618), should ensure improved efficacy to prevent viral escape and dosing convenience.

Introduction

Angiotensin converting enzyme 2 (ACE2) has been primarily studied for its properties as a monocarboxy-peptidase that efficiently cleaves Angiotensin (Ang) II to form Ang 1-7 (1, 2). ACE2 cleaves also several substrates of interest in cardiovascular and kidney disease, such as apelin 13 and 36 and des 9Arg bradykinin (2-15). Early in 2020, it was recognized that ACE 2 is the main receptor for SARS-CoV-2 (16-20). After binding of SARS-CoV-2 S spike to membrane-bound full length ACE2 (FL-ACE2) there is priming by a protease TMPRSS2 that is needed for the fusion and internalization of the ACE2-viral spike complex (16). Administration of soluble ACE2 protein agent acting as a decoy to bind to SARS-CoV-2 should limit viral uptake mediated by membrane-bound FL-ACE2. Consequently, SARS-CoV-2 entry into the cells and viral replication should be prevented. In addition, further therapeutic benefit should result from restoring decreased ACE2 activity and therefore correct the altered balance of Ang II and bradykinins (21).

We have recently generated soluble short recombinant mouse ACE2 variants that exhibit full ACE2 activity (15). Among other things, the present disclosure has provided an insight that such short soluble variants of ACE2 may be particularly useful as decoys to inhibit infection by SARS-CoV-2 (and, in some embodiments, other viruses that utilize the ACE2 receptor).

The present disclosure reports the generation of a human counterpart of the above-mentioned short recombinant mouse ACE2 variant; this exemplified human ACE2 (hACE2) variant has 618 amino acids and is referred to herein as hACE2(1-618).

Furthermore, the present disclosure identifies the source of a problem in certain strategies that might be pursued to utilize a soluble ACE2 variant as a decoy for treatment of SARS-CoV-2 (as, for example, is described in reference (23), which describes a case report of a COVID-19 patient that appeared to respond favorably to the administration of soluble ACE2 therapy given for compassionate use) in that relatively short duration of action (e.g., relatively short serum half life) may hinder effectiveness.

Among other things, the present disclosure provides a soluble ACE2 variant in which a short ACE2 (e.g., hACE2 (1-618)) is fused with a moiety (e.g., albumin binding domain (ABD) polypeptide, and specifically with an ABD-Con polypeptide); the present Example demonstrates that such a fused variant (referred to herein as hACE2(1-618)-ABD) has an increased duration of action, including relative to naked (i.e., unfused) hACE2(1-618). Without wishing to be bound by any particular theory, we reasoned that, when administered in vivo, this feature of enhanced duration of action should provide a more favorable profile in terms of intercepting the SARS-CoV-2 than, for example, the natural soluble protein (i.e., hACE2(1-740)), which has a short duration of action of only a few hours (9, 24).

The present Example also confirms that our novel soluble ACE2 variants (e.g., hACE2(1-618), and moreover hACE2 (1-6180-ABD) can reduce SARS-CoV-2 mediated infectivity. Specifically, the present Example documents, using an established human kidney organoids model, that our provided soluble hACE2 variants show efficacy of our novel ACE2 variants in neutralizing SARS-CoV-2 infectivity.

With respect to our choice of the human kidney organoid model for assessment of our provided soluble ACE2 variant polypeptides, we note that rodent ACE2 lacks the binding domain for the S spike of SARS-CoV-2 (25) found in human ACE2 (16-20), and therefore are naturally resistant to infection with SARS-CoV-2 infection. We further note that this model, which was originally developed to facilitate study of certain aspects of kidney injury including inherited kidney diseases, development disorders and nephrotoxicity (26-28), is acknowledged in the field to be informative in the context of viral infectivity, specifically including SARS-CoV-2 infection (see, for example, reference (22), which reports a neutralizing effect of soluble ACE2(1-740) on SARS-CoV-2 infectivity in human kidney organoids). Those skilled in the art will appreciate, therefore, that human kidney organoids data provided herein confirms the efficacy of our novel soluble ACE2 variants in neutralizing SARS-CoV-2 infectivity.

Methods

Generation of human hACE2(1-618) and a fused chimera with an Albumin Binding Domain tag. A C-terminally truncated recombinant human ACE2 protein of 618 amino acids that we termed ACE2(1-618) was generated using an approach similar to that used previously by us to generate a short mouse ACE2 variant of 619 amino acids (i.e., mACE2 (1-619)(15) (see Example 2, Methods), which we showed retained enzymatic activity comparable to that of non-truncated soluble ACE2 (i.e., ACE2(1-740). This hACE2(1-618) polypeptide was then fused with a small (5 kDa) albumin-binding domain (ABD) tag in order to prolong in vivo duration of action (as described in more detail in the Example 2, Methods). Specifically, hACE2(1-618) was fused with an artificial ABD variant known as ABDCon, which is known to have improved albumin binding affinity (fM range), favorable biophysical characteristics and improved stability. A a flexible linker (G4S3) which engineered into the construct at the N-terminus from the ABD-Con (IDT) by using "sewing" PCR to link (i) a cDNA encoding the G4S3-ABDCon construct with (ii) a cDNA encoding hACE2(1-618) cDNA. The encoded fusion chimera is referred to here as hACE2(1-618)-ABD). The cDNA encoding the hACE2(1-618)-ABD fusion chimera was inserted into pcDNA6 plasmid (Invitrogen) using custom synthesized complementary primers (IDT) and the Gibson assembly kit (NEB). After verifying the DNA sequence of the pcDNA6 including the hACE2(1-618)-ABD coding sequences, HEK293 cells were then transfected with the plasmid construct. Both the naked (i.e., un-fused) hACE2 (1-618) and the hACE2(1-618)-ABD fusion were expressed in human kidney embryonic cell line 293 and purified using Fast Protein Liquid Chromatography on Q-Sepharose followed by size exclusion chromatography on Superdex 200 pg.

Enzyme Activities and Kinetic Constants of Purified Soluble ACE2 Variants. To compare enzymatic activities of purified hACE2(1-618) and hACE2(1-618)-ABD, we tested their ability to cleave two natural substrates of ACE2, Ang II-(1-8), to form Ang-(1-7), as well as des-9Arg-Bradykinin (bradykinin-(1-8)), to form bradykinin-(1-7) (5). ACE2 is known to remove the C-terminal amino acid phenylalanine from the cleavage reaction with either substrate (5). An assay quantifying phenylalanine formation from these two substrates (29) was used to evaluate the relative enzymatic potency of the two short soluble ACE2 variants as compared to equivalent molar amounts of the standard soluble ACE2 (1-740), which was used as a benchmark. For assessment of activity levels, the Michaelis-Menten model was used to derive the parameters of catalytic kinetics such as Km and Kcat (29, 30).

Plasma ACE2 activity. The pharmacokinetic profiles of hACE2(1-618)-ABD were assessed in WT mice as compared to those of naked hACE2(1-618) and the non-truncated soluble parent polypeptide, ACE2(1-740). The mice received a single i.p. injection of each purified soluble ACE2 variant at a dose of 1 ug/g body weight. Blood samples were collected by tail bleeding either before or at several indicated time points after injection. Blood samples were collected in heparinized capillaries and plasma was isolated by centrifugation at 1850 g for 10 min at 4° C. Mca-APK(Dnp) substrate (Bachem, Bubendorf, BL, Switzerland), PA) was used to measure ACE2 enzyme activity in plasma. The pharmacokinetic parameters based on plasma ACE2 activity measurements were calculated (30) using Prism 8 software (GraphPad, La Jolla, CA).

Blood Pressure Response to Ang II-Induced Hypertension. Biologic enzymatic activity was assessed in vivo for our hACE2(1-618) variants, and the ACE2(1-740) parent polypeptide, using a model of Ang II-induced hypertension (9, 15). The effect of these three ACE2 poltpeptides on acute Ang II induced hypertension were examined as previously described by us (9, 15, 31). We injected 10-20-week old male C57bl/6 mice i.p. with either vehicle (PBS), ACE2(1-618) or ACE2(1-618)-ABD (both 1 mg/kg of body weight). After 1 hour, 3 days or 7 days, mice were anesthetized with an i.p. injection of ketamine (150 mg/kg of body weight) and then placed on a temperature-controlled platform immediately. Systolic blood pressure (SBP) was monitored noninvasively every 30 seconds for a period of 20 minutes including five minutes of baseline SBP recording, after which acute hypertension was induced with an i.p. bolus injection of Ang II (0.2 mg/kg of body weight).

Generation of human kidney organoids and culture conditions. Human kidney organoids (HKO) were generated using a published protocol (26), with slight modifications. H9 cells (WA09 cell line from WiCell, NIH approval number NIHhESC-10-0062) were plated at a density of $1.7 \times 10^4$ cells/cm$^2$ in mTeSR1 medium (STEMCELL Technologies, Canada) on a geltrex (ThermoFisher Scientific) coated six-well plate. Once cells became ~50% confluent, differentiation was started with the treatment of 8 µM HIR99021 (Reprocell) in the basic differentiation medium (advanced RPMI 1640 containing 1×L-gluatmine supplement). On day 4, medium was replaced with basic differentiation medium supplemented with 10 ng/ml Activin A, and on day 7 medium was replaced with basic differentiation medium supplemented with 10 ng/ml FGF9. On day 9, differentiated kidney progenitors form renal vesicle-like clusters and were fed with the basic differentiation medium supplemented with 10 ng/ml FGF9 and 1 µM CHIR99021. On day 11, the medium was changed to the basic differentiation medium containing 10 ng/ml FGF9. From day 14, the cells were fed with the basic differentiation medium every 2-3 days until harvest on day 21. On day 21, some organoids were transferred to a 6-well plate or collected for isolation of cellular fractions. Several days later, using sterile tips, organoids from the 6 well plate were plated onto a sterile 96-well plate with fresh medium (5 organoids/well) for subsequent tissue infectivity experiments.

Another set of human kidney organoids was generated from human pluripotent stem cells (hPSC) as described (32) and used for staining studies. Briefly, highly functional kidney cells were generated by keeping an optimal balance between static traditional tissue culture and 3D organ culture. We used an NIH-approved human H9 ESC line (WA09 cell line from WiCell, NIH approval number NIHhESC-10-0062). For the directed differentiation of H9 cells in kidney progenitors, cells were plated at a density of $1.7 \times 10^4$ cells/cm2 in StemFit (ams-bio) on a geltrex (ThermoFisher Scientific) coated six-well plate (see Example 2). Staining was done using anti-human ACE2 (AF933, R&D Systems) and anti-TMPRSS2 antibodies (Novus, NBP-2 38263) to localize expression of ACE2 and TMPRSS2.

In vitro assay for detection of hACE2-RBD interaction. Using an artificial ACE2 substrate, Mca-APK-Dnp (10 µM), activity of ACE2(1-740) was not affected by the presence of recombinant glycosylated RBD in a 0.001 to 100 ng/ml concentration range. Based on this finding, we developed a method that measures interaction between viral S1 RBD and human ACE2 using as a readout ACE2 activity. Purified His-tagged RBD protein was dissolved in Tris-buffered saline (TBS) pH 7.4 and loaded into 96-well Ni-coated black plate for binding. TBS alone was loaded to blank wells. After incubation for 1 hour at room temperature, five washes were done. 100 µL of human ACE2(1-740) (positive control), and mouse ACE2(1-740) (negative control) were added to the wells and incubated for 1 hour at room temperature at concentrations ranging from 1000 ng/ml to 6.25 ng/ml. Afterward, wells were washed 5 times. Finally, Mca-APK-Dnp substrate (1 µM final concentration) was added and fluorescence formation was measured in microplate fluorescence reader (see detailed description in Example 2, Methods). Dose-dependent binding of enzymatically active hACE2 polypeptide to the RBD-His protein immobilized onto the Ni-coated microplate was confirmed by concentration-dependent increase in fluorescence formation (expressed in relative fluorescence unit—RFU) from the cleavage of the Mca-APK-Dnp ACE2 substrate.

We used lysates of isolated cytosol, nuclear or membrane fractions from human kidney organoids to assess binding of hACE2 polypeptides from those isolated fractions to the RBD domain of SARS-CoV-2 S1 protein. Purified His-tagged RBD protein was dissolved in TBS and loaded into 96-well Ni-coated black plate (100 μL/well) for binding for 1 hour. After five washes, the organoid tissue lysate samples (10 μL) were diluted in 90 μL TBS, loaded onto the plate and left for 1 hour at room temperature. Afterward, wells were washed 5 times, before Mca-APK-Dnp substrate (1 μM final concentration) was added and fluorescence formation was measured in a microplate fluorescence reader (see detailed description in Example 2, Methods). The measured fluorescence in organoid lysates was corrected for total protein content and converted to a concentration of ACE2 polypeptide by reference to a standard curve of recombinant ACE2 (R&D Systems) assayed under the same conditions.

Figure 1:
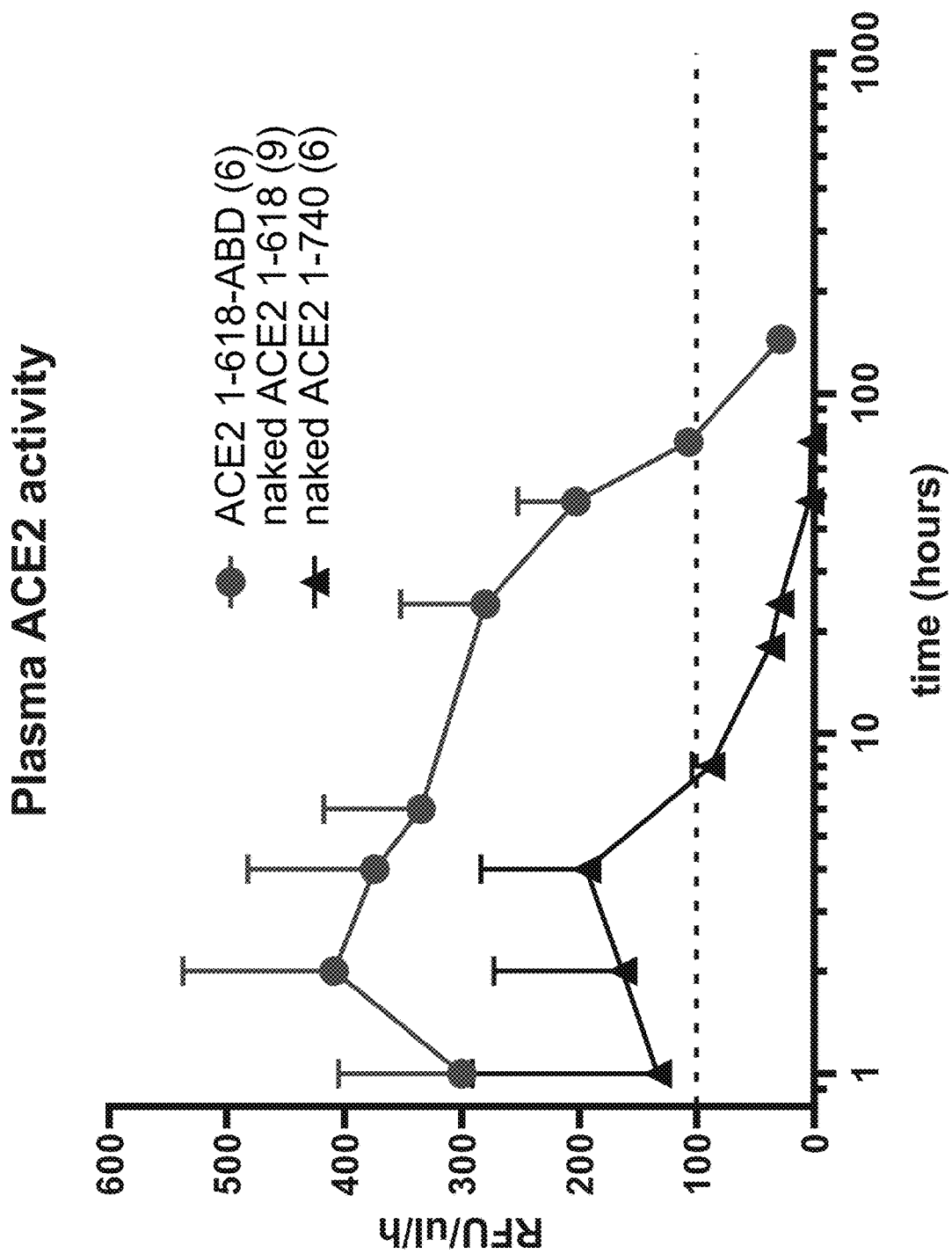
FIG. 1. Pharmacokinetics of soluble human recombinant ACE2 variants in vivo after i.p. injection. Mice were injected i.p. with either the novel human ACE2(1-618)-ABD, the novel human naked ACE2(1-618) or the native human ACE2(1-740). Plasma ACE2 activity was measured at various time points, starting 1 hour post injection as a way to determine duration of action. The ACE2(1-618)-ABD variant resulted in a higher peak plasma ACE2 activity as compared to the naked ACE2(1-618) and the non-truncated ACE2(1-740). Whereas the activity of the naked ACE2(1-618) and ACE2(1-740) had decreased markedly by 8 hours, the ACE2(1-618)-ABD resulted in persistent activity at 72 and 96 hours, therefore demonstrating a marked extension of in vivo duration of action of ACE2 1-618 achieved by adding the ABD tag.
Figure 2:
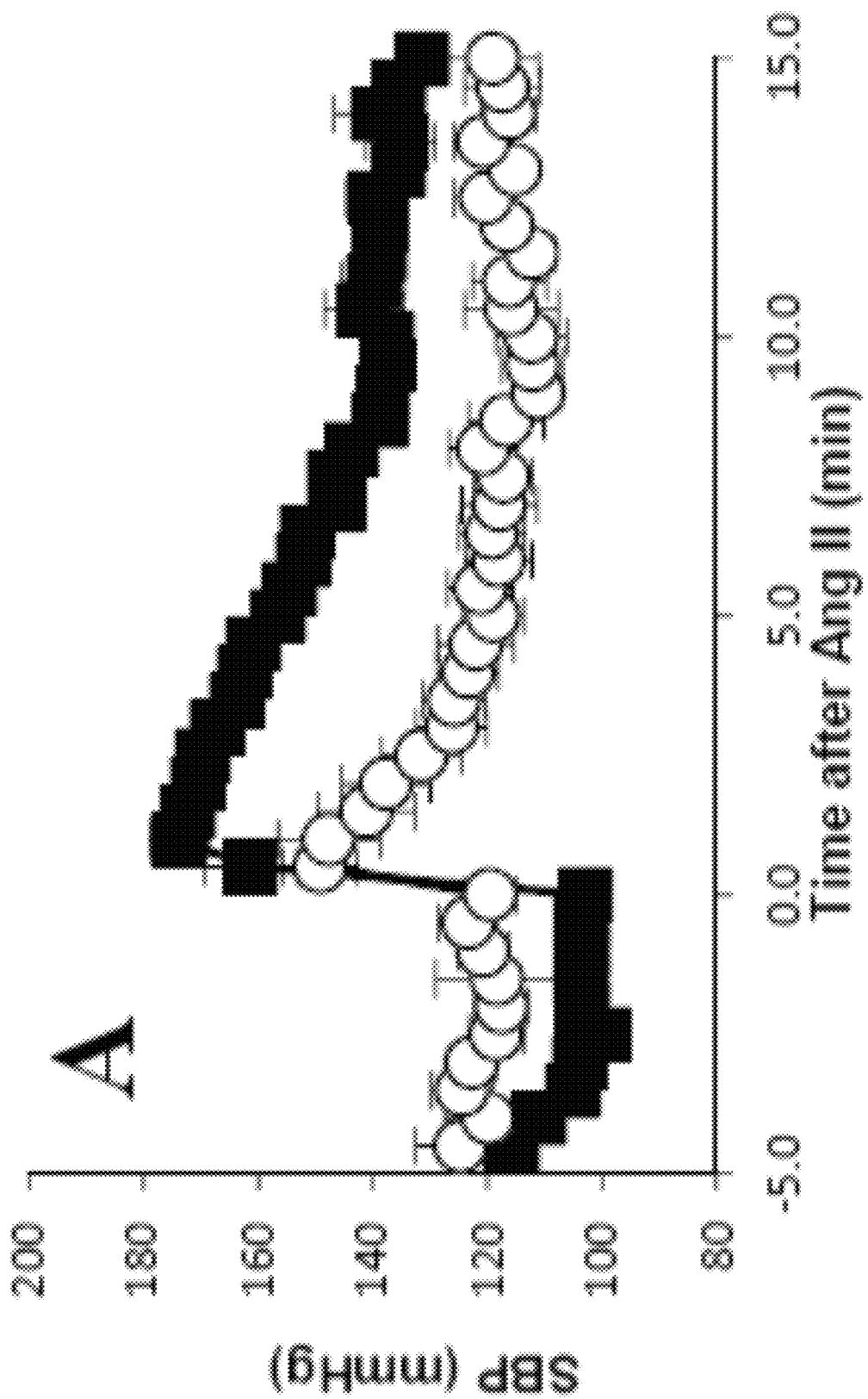
FIG. 2. Blood pressure-lowering effect of human ACE2 proteins in Angiotensin II (Ang II) induced hypertension in mice as a measure of biologic activity. In Panels A, B and C the ACE2 proteins were given i.p. 1 hour prior to Ang II injection. The increase in systolic blood pressure (SBP) as compared to controls (A: n=6, B: n=4, C: n=4) was blunted and normalized by the ACE2(1-740) (n=6) ($p<0.01$) (Panel A). Similarly, ACE2(1-618) (n=5) (Panel B) and ACE2(1-618)-ABD (n=5) both blunted the raise in BP and resulted in much lower values ($p<0.05$ and $p<0.01$, respectively) (Panel C). In Panels D and E the ACE2 proteins were given i.p. 3 days prior to Ang II injection. Both, the naked ACE2(1-618) (n=5) and the ACE2(1-740) (n=5) were no longer effective in normalizing the SBP after Ang II injection as compared to controls (n=4) (Panel D). In contrast, ACE2(1-618)-ABD (n=4) significantly attenuated Ang II induced hypertension as compared to controls (n=9) ($p<0.01$) (Panel E). In Panel F, ACE2(1-618)-ABD protein (n=5) was given i.p. 7 days prior to Ang II injection and was no longer effective in lowering the SBP after Ang II injection just like the controls that received PBS (n=9). ABD=Albumin binding domain.
Figure 2:
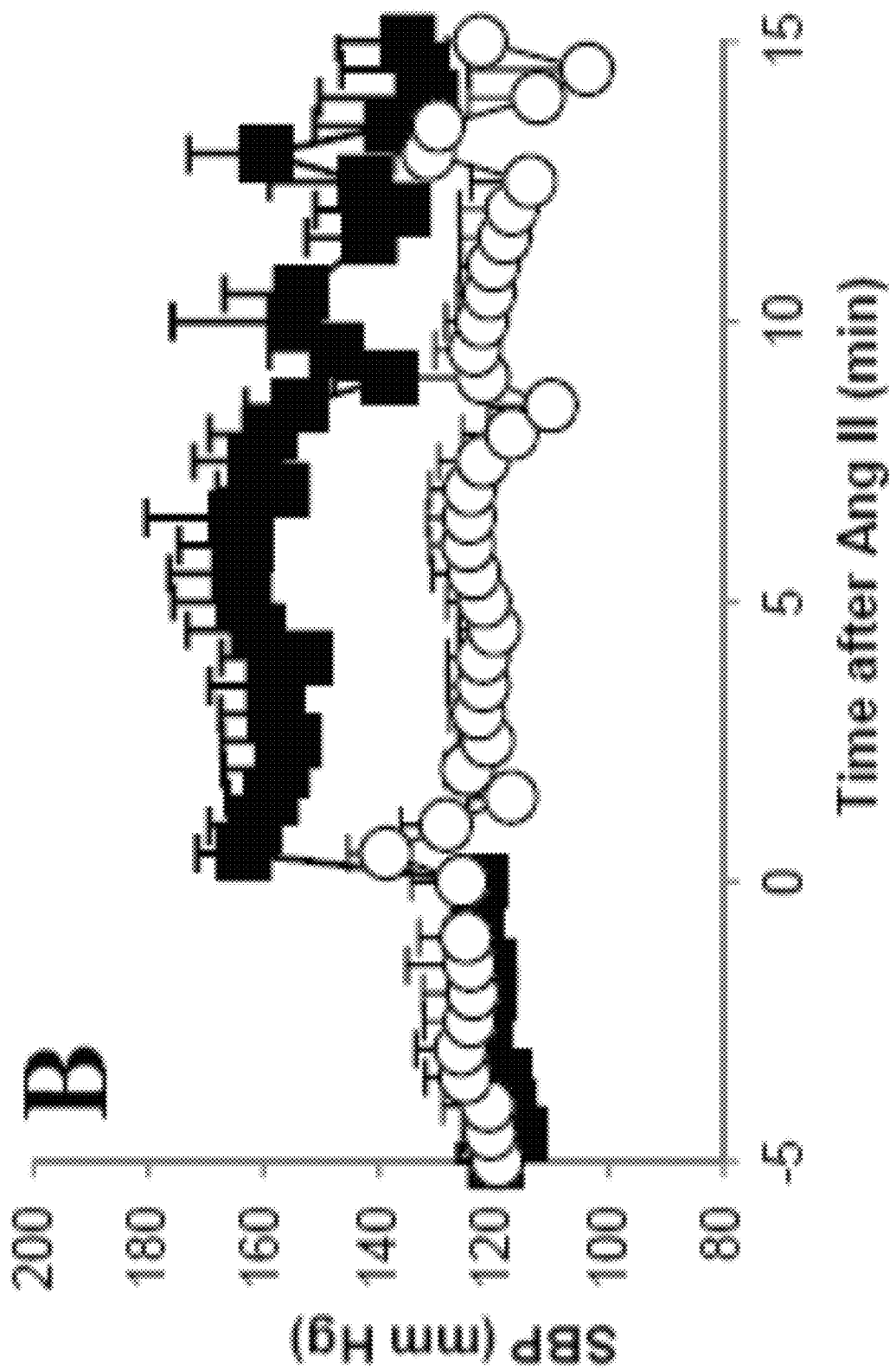
Figure 2:
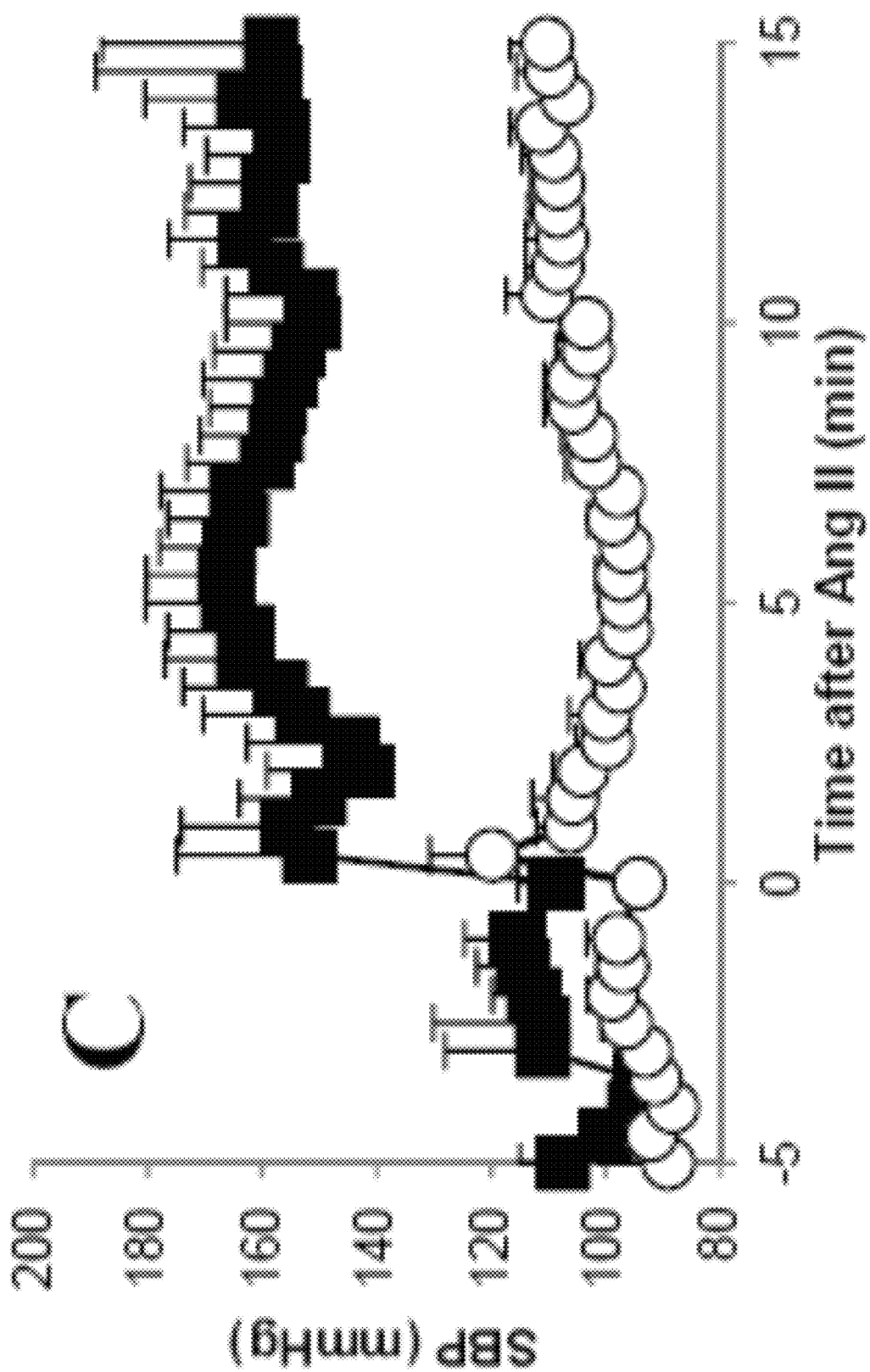
Figure 2:
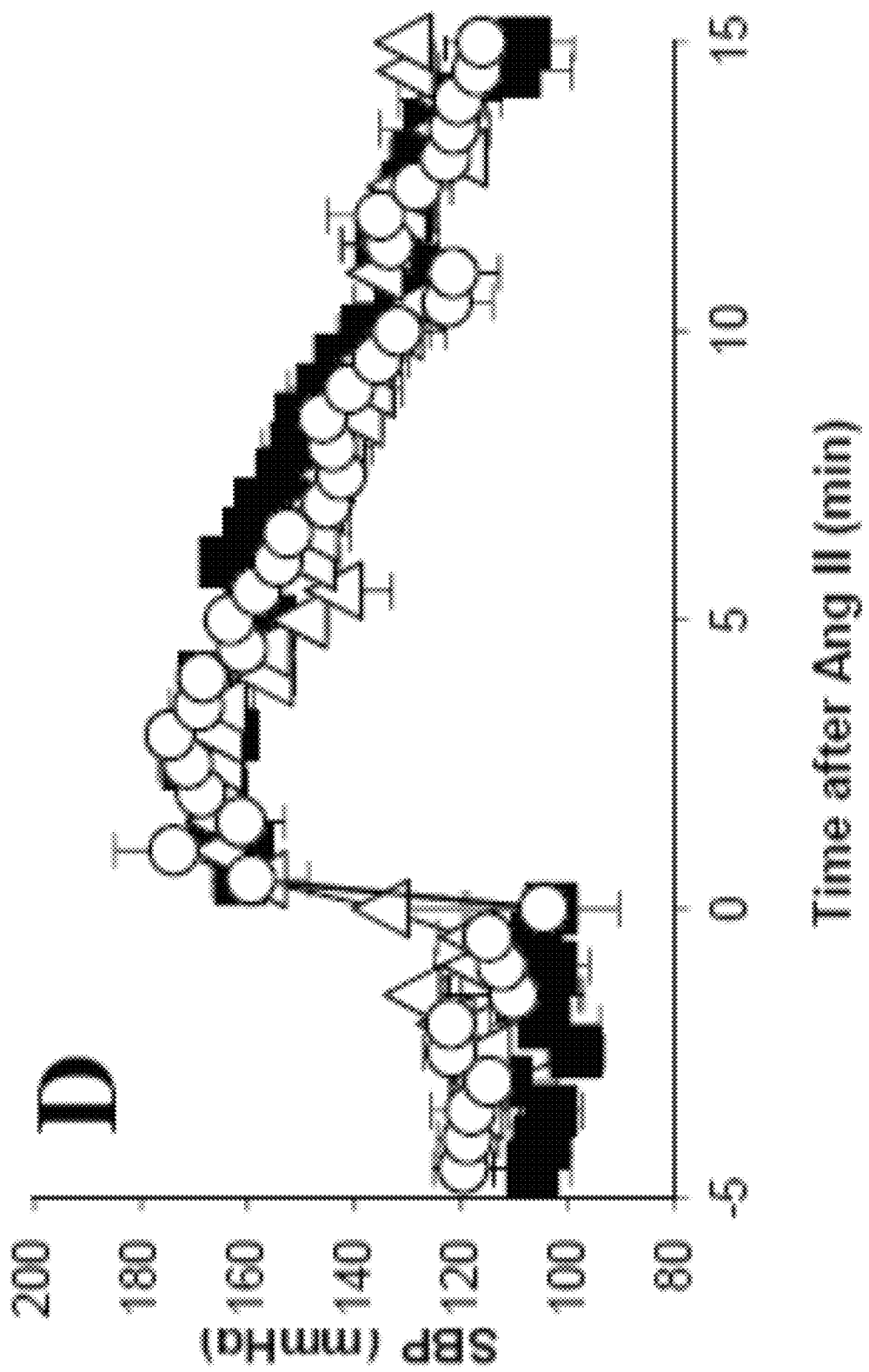
Figure 2:
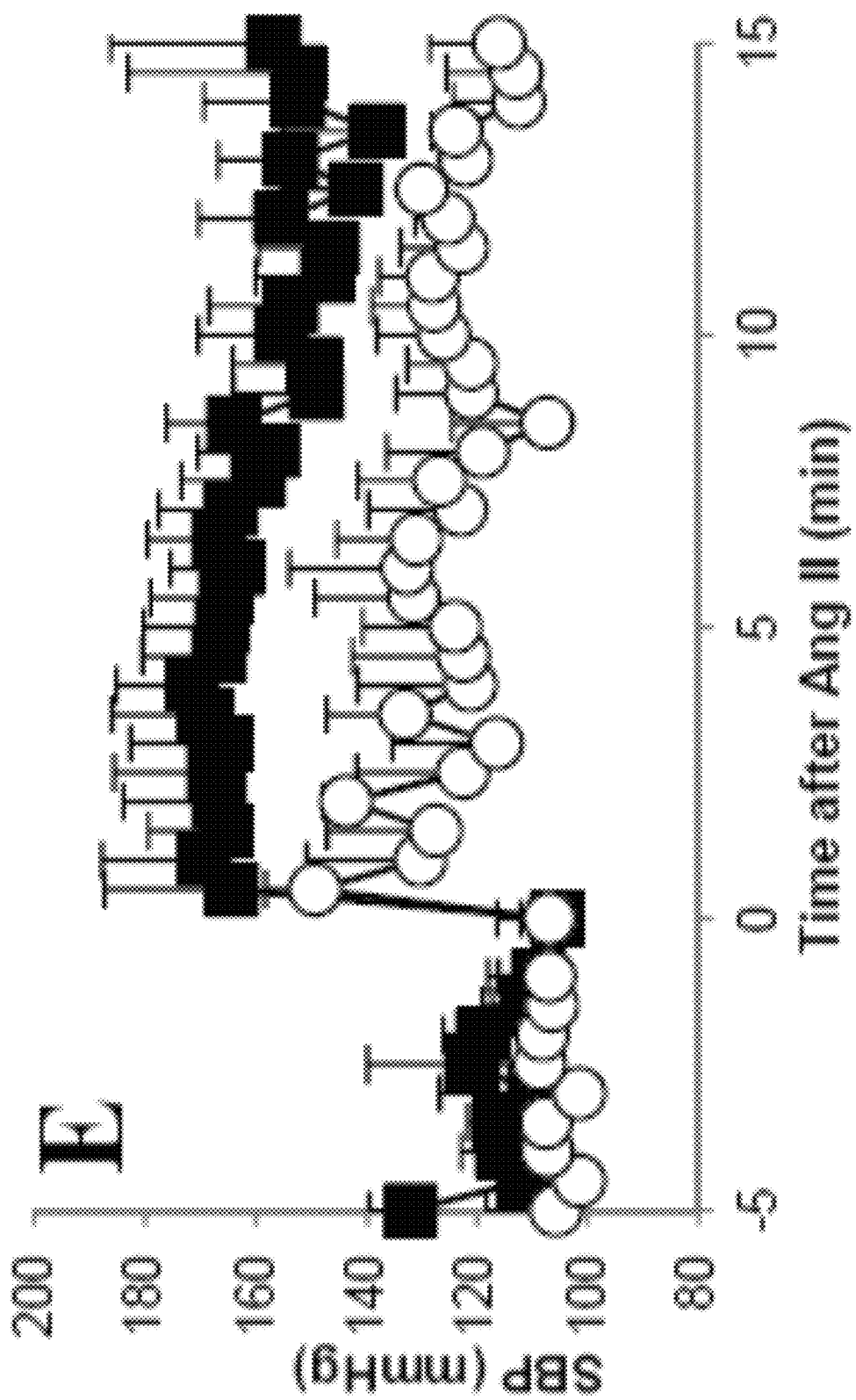
Figure 2:
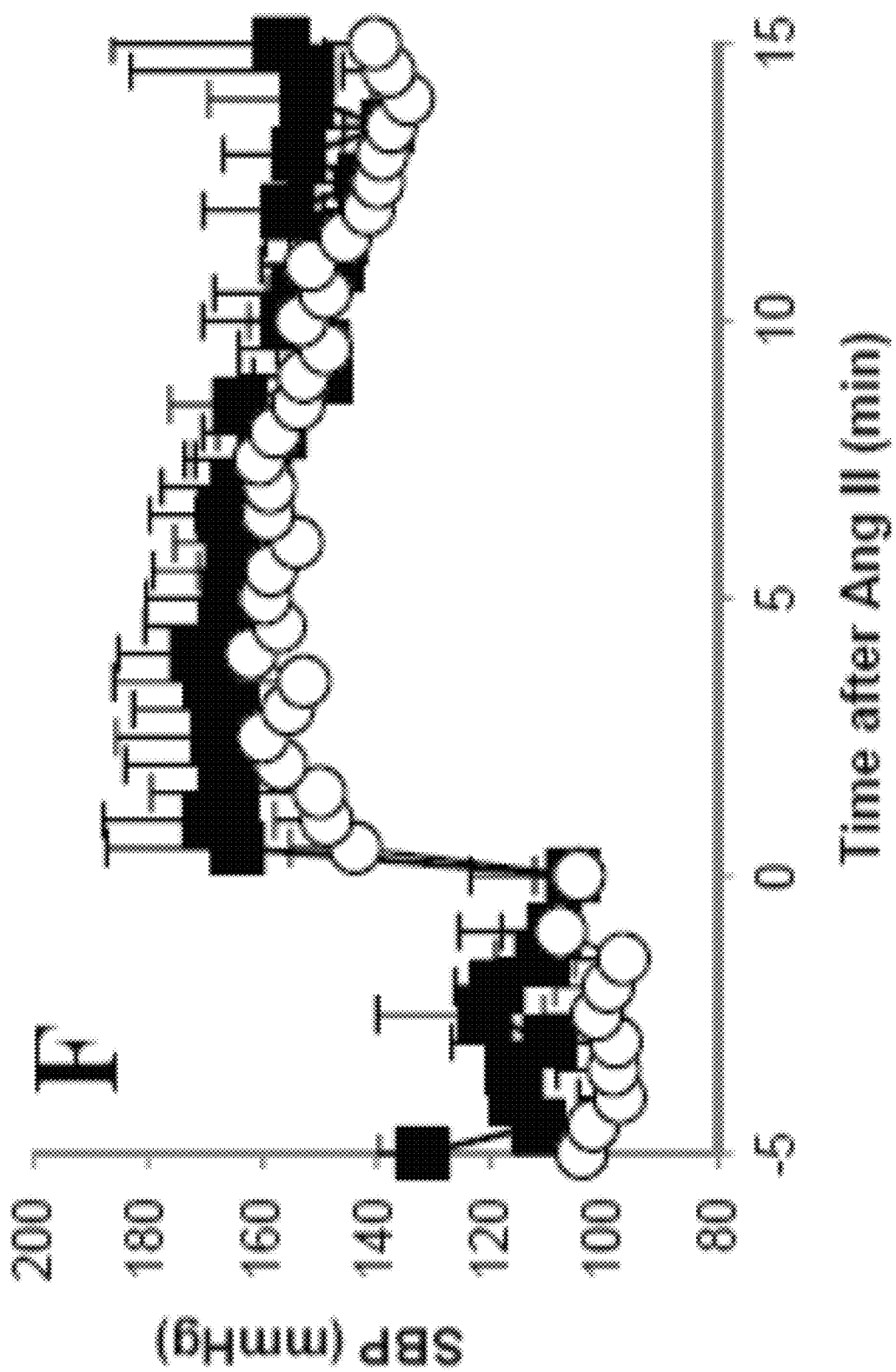
Figure 3:
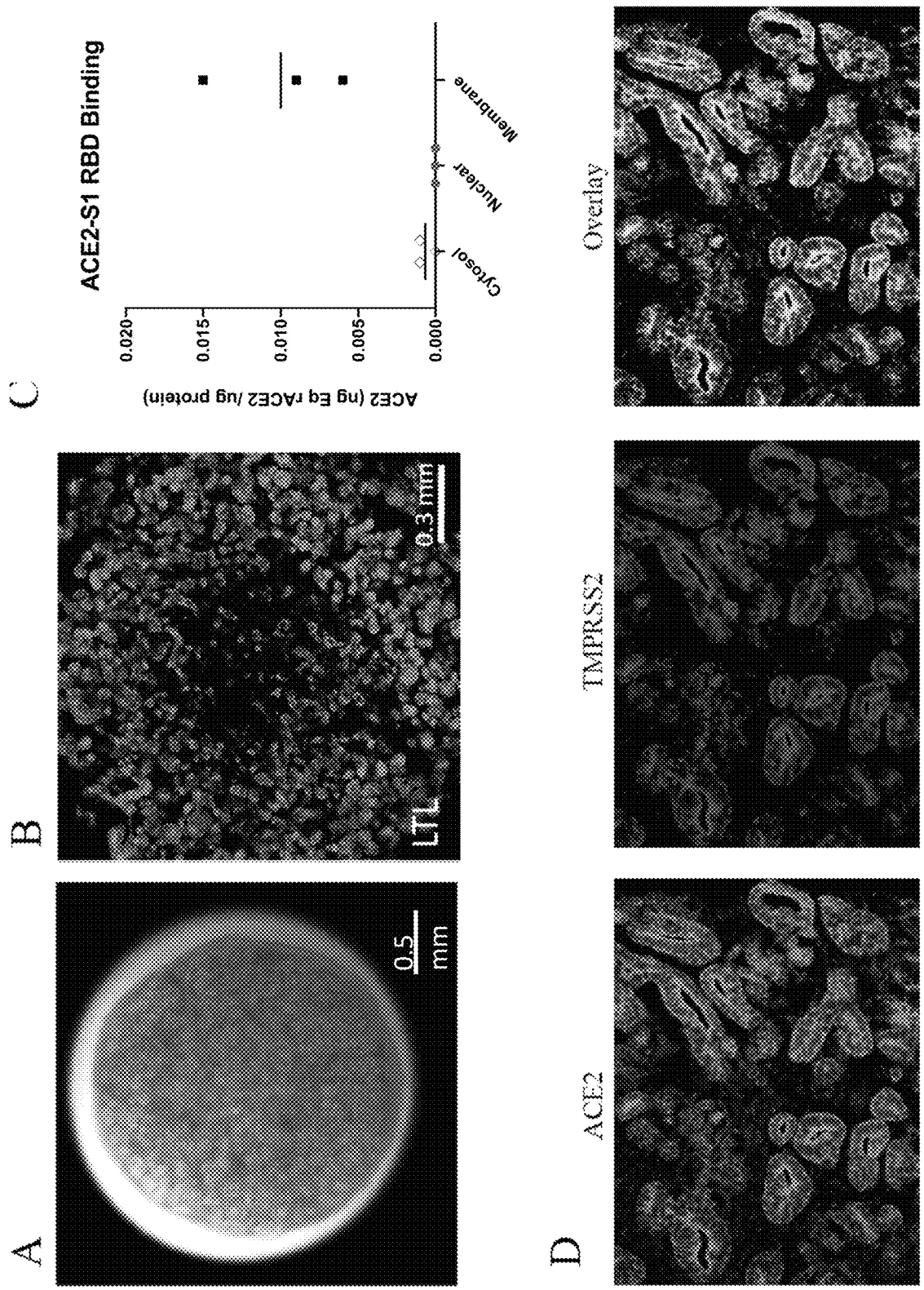
FIG. 3. Human Kidney Organoids express ACE2 which can bind to the RBD domain of the SARS-CoV-2 S1 spike protein. Kidney organoids were generated from asynchronous mixing of two differentiating human ESCs derived kidney progenitors at the air-liquid interface. Representative photomicrograph of kidney organoid showing tightly packed tubular clusters on day 18 (Panel A) and Lotus Tetragonolobus Lectin (LTL) staining showing that kidney organoids were filled with proximal tubule like structures (Panel B). In silico pull-down assay showing binding of ACE2 to the RBD domain of SARS-CoV-2 S1 spike protein. ACE2 from either cytosol, nuclear or membrane fractions of kidney organoids (n=3 per group) (Panel C). Immunofluorescence staining showing high expression of ACE2 and TMPRSS2 in tubule-like structures of kidney organoids and areas of colocalization in the apparent apical membrane (Panel D).
Figure 4:
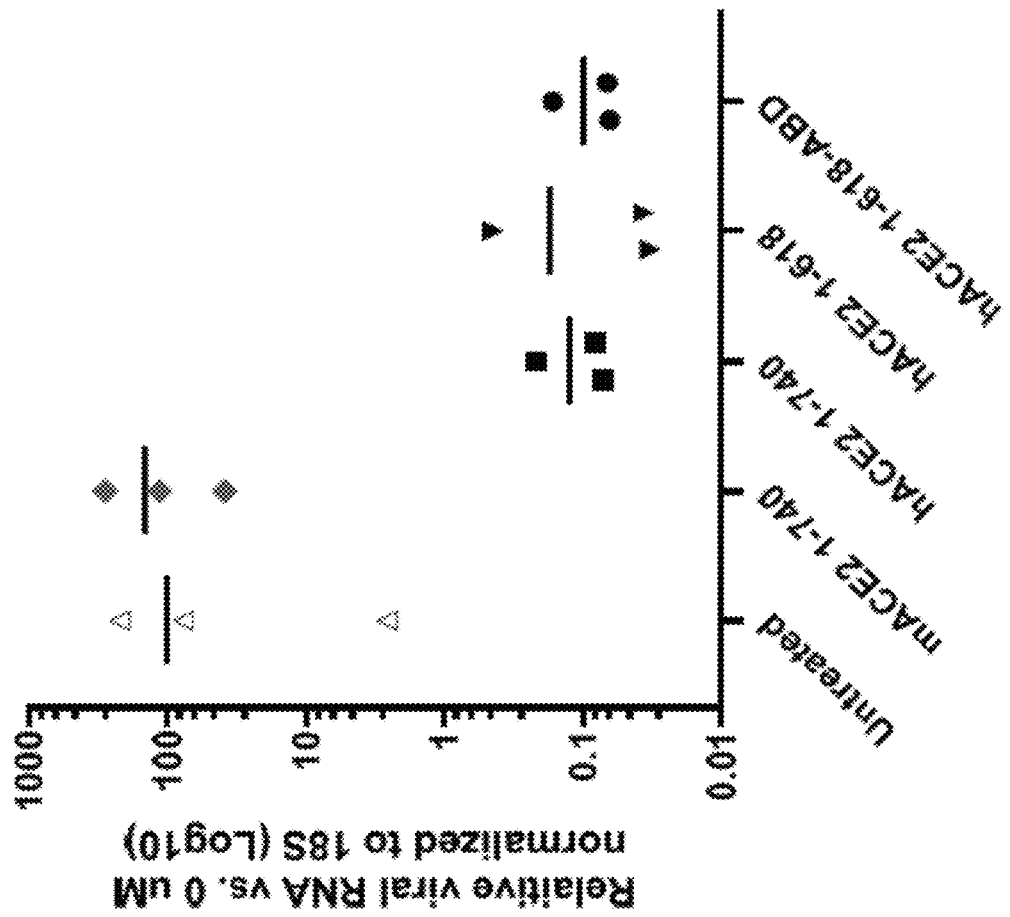
FIG. 4. Effect of recombinant soluble ACE2 proteins on SARS-CoV-2 on infected human kidney organoids. Kidney organoids were infected with a combination of infectious viral particles (400 PFU) and soluble human or mouse ACE2 proteins (n=3 per each group) for 1 hour. Three days post infection, levels of viral RNA were assessed by RT-qPCR. All three human ACE2 variants markedly reduced RNA levels of SARS-CoV-2 whereas the mouse ACE2(1-740) counterpart that lacks the binding site for SARS-CoV-2, did not. Single data points and mean are shown for each group.

SARS-CoV-2 neutralization assay. Under Biosafety Level 3 (BSL-3) conditions, 0 and 200 μM of indicated ACE2 polypeptides (mouse ACE2(1-740), and human ACE2(1-740), human ACE2(1-618) and human ACE2(1-618)-ABD) in PBS were mixed with 400 PFU of SARS-CoV-2 (nCoV/Wasington1/2020, kindly provided by the Bational Biocontainment Laboratory, Galveston, TX) in DMEM for one hour at 37° C. and then used to infect kidney organoid cells for three days. Advanced RPMI medium without ACE2 was used as not-treated reference. Cells were washed and lysed in RNA extraction buffer and purified using a NucleoSpin 96 RNA kit following the manufacturer's instructions (Macherey-Nagel). SARS-CoV-2 RNA was quantified by qRT-PCR using SuperScript™ III Platinum™ One-Step qRT-PCR Kit w/ROX (ThermoFisher Scientific) and normalized using Eukaryotic 18S rRNA Endogenous Control (VIC™/MGB probe, 29Applied Biosystems) via a StepOnePlus real-time PCR system (Applied Biosystems). All reactions were performed in a dual-plex qRT-PCR using the CDC recommended primers for N1. Primer and probe sequences are as follows:

```
2019-nCoV_N1
Forward Primer (2019-nCoV_N1-F),
GACCCCAAAATCAGCGAAAT;

2019-nCoV_N1
Reverse Primer (2019-nCoV_N1-R),
TCTGGTTACTGCCAGTTGAATCTG;

Probe (2019-nCoV_N1-P),
FAM-ACCCCGCATTACGTTTGGTGGACC-BHQ1.
```

Results

Catalytic Efficiency of hACE2(1-618) and hACE2(1-618)-ABD as determined by Phenylalanine assay (see Example 2, Results).

Prolonged in vivo activity of human ACE2 Variant hACE2(1-618)-ABD. The peak plasma ACE2 activity for the naked hACE2(1-618) and the non-truncated soluble hACE2(1-740) was between 2 and 4 hours (FIG. 1). The hACE2(1-618)-ABD variant resulted in a higher peak plasma ACE2 activity as compared to the naked ACE2(1-618) and the reference ACE2(1-740). Furthermore, whereas the activity of the naked hACE2(1-618) and non-truncated soluble ACE2(1-740) had decreased markedly by 8 hours, the hACE2(1-618)-ABD variant showed persistent activity at 72 and 96 hours (FIG. 1). For duration of action of the ACE2 proteins see Example 2. Thus, the provided hACE2 (1-68)-ABD variant showed both improved level of ACE2 catalytic activity and improved duration of action relative to the reference soluble ACE2(1-740), and even relative to the hACE2(1-618) truncation variant.

Blood pressure-lowering effect of hACE2(1-618) and hACE2(1-618)-ABD during Acute Ang II Infusion. In one set of experiments, mice were pretreated with either vehicle (PBS), ACE2(1-740), hACE2(1-618) or hACE2(1-618)-ABD by a single i.p. injection (at 1 mg/kg BW) 1 hour before receiving a bolus injection of Ang II (0.2 mg/kg BW). The injection of Ang II 1 hour later resulted in a rapid increase in BP in the control group that had received PBS as pre-injection vehicle, followed by its decline. In contrast, the increase in BP was markedly blunted and normalized to about the same extent by the three proteins (FIG. 2, panels A, B and C).

To examine their duration of action, the same injection protocol was used except that Ang II was injected 3 days after injection of ACE2(1-740), naked hACE2(1-618) and hACE2(1-618)-ABD. Three days after their injection, neither ACE2(1-740) nor the naked hACE2(1-618) were effective in normalizing the BP after Ang II injection (FIG. 2, Panel D). By contrast, hACE2(1-618)-ABD, when given 3 days prior to Ang II injection, still had a significant attenuation of BP (FIG. 2, Panel E). When hACE2(1-618)-ABD was given 7 days prior to Ang II injection, however, the response was no longer different from the PBS-treated control (FIG. 2, Panel F).

Human Kidney Organoids express ACE2 which can bind to the RBD domain of the SARS-CoV-2 S spike. Human kidney organoids were generated as described (26, 32). A representative photomicrograph of a kidney organoid showed tightly packed tubular clusters on day 18 (FIG. 3A). Lotus Tetragonolobus Lectin (LTL) staining confirmed that kidney organoids were filled with proximal tubules (FIG. 3B). We examined the presence of ACE2 and TMPRSS2, a protease needed for SARS-CoV-2 S spike and ACE2 activation (16). We confirmed by immunofluorescence and confocal microscopy, that ACE2 was expressed in tubular-like structures mainly in what appears to represent the apical membrane (FIG. 3D). Staining for the protease TMPRSS2 was also present in these structures and moreover, there was colocalization with ACE2 staining (FIG. 3D).

Human kidney organoids were used to isolate cytosolic, nuclear and membrane fractions for subsequent evaluation of ACE2 activity. Consistent with immunostaining, in the membrane fraction ACE2 activity was clearly detectable (0.55±0.18 ng Eq rACE2/μg total protein, n=3). ACE2 activity was also found in the nuclear fraction but none could be detected in the cytosolic fraction (not shown).

To confirm that ACE2 from kidney organoids is capable to bind the receptor-binding domain (RBD) of the SARS-CoV-2 S1 spike protein, the same isolated cell fractions were tested in an in vitro pull-down assay capable of detecting human ACE2-RBD interaction. Interaction of the SARS-CoV-2 S1 spike protein and ACE2 was found to take place mainly in the membrane fraction of the kidney organoids. This finding confirms that the ACE2 that is present in the human kidney organoids plasma membrane can bind the SARS-CoV-2 S1 spike protein (FIG. 3C). Negligible ACE2-RBD interaction was detected in the nuclear fraction and in the cytosolic fraction, consistent with low ACE2 activity measured in these fractions.

Neutralization of SARS-CoV-2 in kidney organoids pre-exposed to soluble ACE2 polypeptides. Naked and ABD-tagged human ACE2(1-618) were used at a concentration (200 μg/ml) at which soluble non-truncated human ACE2 (1-740) was found effective in maximally neutralizing SARS-CoV-2 (22). Soluble human ACE2(1-740) was used as a positive control, and mouse ACE2(1-740) (which does not bind to SARS-CoV-2 S1 spike) as a negative control at the same concentration. Provided soluble ACE2 variant polypeptide agents (specifically, hACE2(1-618) and hACE2 (1-618)-ABD) were mixed with SARS-CoV-2 particles (MOI 0.02 for 30 min at 37° C.) in an advanced RPMI medium. Kidney organoids were then infected for 1 hour at 37° C., washed with PBS and a new medium was added. On the 3rd day after infection, levels of viral RNA were assessed by RT-qPCR. As expected, mouse ACE2(1-740) did not prevent viral infectivity, as shown by similar high viral mRNA levels as in the untreated group (FIG. 4). By contrast, both naked and ABD-tagged hACE2(1-618) markedly reduced viral replication to the same extent as human ACE2(1-740) used as positive control (FIG. 4).

Discussion

The present Example provides details relating to the generation of a truncated soluble human ACE2 with 618 amino acids (i.e., hACE2(1-618)), and also of a fusion polypeptide of hACE2(1-618) with ABD (i.e., hACE2(1-618)-ABD. The present Example further demonstrates that such fusion with ABD extends the duration of action relative to that observed with naked hACE2(1-618), or to that observed with non-truncated soluble human ACE2, which has 740 amino acids (i.e., hACE2(1-740).

Moreover, the present Example documents that both hACE2(1-618) and hACE2(1-618)-ABD are as active as hACE(1-740) as demonstrated by their catalytic efficiency and biologic activity. The latter was demonstrated by the response of blood pressure to infused Ang II which was comparable to that of hACE2(1-740) in acute studies. Remarkably, the present disclosure further documents that the fused hACE2(1-618-ABD) chimera has dramatically extended effect as compared with either naked hACE2(1-618) or hACE2(1-740); indeed, enzymatic activity and BP lowering effects of hACE(1-618)-ABD in assays reported herein lasted for at least 3 days.

The present Example further documents that the novel hACE2(1-618)-ABD variant was capable of neutralizing SARS-CoV-2 infectivity in human kidney organoids. The present Example specifically documents that such neutralizing effect was achieved at a dose comparable to that at which non-truncated soluble protein is reported to show maximal neutralizing effect (22). We also confirmed that no neutralization is observed at this dose with the mouse counterpart, which is known not to bind to the SARS-CoV-2 spike protein.

The present Example further confirms that human kidney organoids have membrane bound ACE2 and that can interact with the receptor-binding domain of the SARS-CoV-2 S1 spike protein. Additionally, we show the presence of TMPRSS2 with areas of colocalization with ACE2 in proximal tubule-like structures. This protease is critically needed for activation of the ACE2-SARS-CoV2-spike complex and subsequent internalization into the cell (16, 34).

Infection with SARS-CoV-2 may result in internalization and loss of membrane bound FL-ACE2, as reported for SARS-CoV (41), degradation of Ang II and des 9Arg bradykinin would be impaired (21). ACE2 loss may increase proinflammatory peptides in lungs and other organs like the kidneys, prone to local injury (21, 41, 42). Thus, administration of soluble enzymatically active ACE2 may have therapeutic benefit added to its decoy effect, by restoring the altered balance of Ang II and bradykinins that ensues with depletion of this enzyme.

Human soluble ACE2(1-740) is a large molecule of ~110 kDa size (11, 35). In fact, under native conditions, ACE2 (1-740) is even bigger, as it forms homodimers roughly double the size of the monomeric protein (31), a process mediated by the collectrin-like domain at the C-terminal part of ACE2 (amino acids 616-726) (36). The present disclosure provides truncated variants of soluble human ACE2, including the hACE2(1-618) variant exemplified in the present Example, that are materially smaller than hACE2(1-740). The present disclosure also provides soluble polypeptides in which a soluble ACE2 fragment (e.g., in the present Example, hACE2(1-618)) is fused to another moiety (e.g., in the present Example, an ABD—specifically ABDCon); the present disclosure teaches, and the present Example confirms, that such fusion polypeptides can maintain relevant ACE2 activity(ies) and have remarkably prolonged duration of action (e.g., relative to the same soluble ACE2 polypeptide but lacking the fusion partner).

Applicant notes that recent literature reports underscore the significance of contributions provided herein. For example, non-truncated soluble human ACE2(1-740) is currently being studied in a clinical trial (NCT04335136) and was also successfully administered i.v. twice a day for compassionate use in a single patient case report recently (23). The present disclosure provides an insight that extending duration of action of a soluble ACE2 can provide important advantages including, for example, a better way to prevent viral escape, and/or feasibility of dosing regimens that involve only a single dose, or a relatively small number of doses, and/or that permit relatively extended spacing between doses.

Still further, the present disclosure provides an insight that use of soluble human ACE2 variant polypeptides that retain ACE2 activity and are sufficiently small to avoid kidney filtration may provide particular advantages in the context of viral infection, and specifically in the context of infection with SARS-CoV-2. For example, the present disclosure provides insights that protective effect on the kidneys provided by shorter variants may be particularly beneficial in this context. Moreover, the present disclosure teaches that combination of such protective effect in the kidneys and long in vivo duration can be particularly beneficial in the treatment of SARS-CoV-2 infection.

The truncated soluble human hACE2(1-618) variant reported here is the counterpart to a mouse ACE2(1-619) that we have recently reported (15), and for which we have document its ability to address associated kidney disease due at least in part to its shorter molecular size, which should render it filterable by the kidney. For example, we have shown that the mouse counterpart mACE2(1-619) protects against AKI in the ischemia-reperfusion model (40). Given that acute kidney injury and collapsing glomerulopathy are frequent complications of COVID-19 (37-39), the present disclosure teaches that truncated soluble ACE2 variants (and particular truncated soluble human ACE2 variants), as described herein, have particular utility for treatment of SARS-CoV-2 infection, particularly in patients suffering from or susceptible to kidney disease or impairment.

Separately, the present disclosure teaches that prolonged-action variants of soluble human ACE2 may have particular utility in the treatment of SARS-CoV-2 infection. It has been reported that fusion with a Fragment crystallizable (Fc) moiety can elongate duration of action of non-truncated ACE2(1-740) (30). The present disclosure teaches (and documents) that activity(ies) of truncated soluble ACE2 variants can be extended by fusion and, moreover, documents such extension by fusion with a tag of a shorter size, e.g., ABD.

Thus, the present disclosure provides soluble ACE2 variant polypeptide agents of smaller size and/or longer duration, documents certain characteristics and surprising attributes of certain such variants, and teaches their specific utility in treatment of viral infection. Importantly, the present disclosure teaches and confirms effectiveness of certain such variants in blocking SARS-CoV-2 infection.

REFERENCES

1. Guy J L, Lambert D W, Warner F J, Hooper N M, Turner A J: Membrane-associated zinc peptidase families: comparing ACE and ACE2. Biochim Biophys Acta, 1751: 2-8, 2005
2. Tipnis S R, Hooper N M, Hyde R, Karran E, Christie G, Turner A J: A human homolog of angiotensin-converting enzyme. Cloning and functional expression as a captopril-insensitive carboxypeptidase. J Biol Chem, 275: 33238-33243, 2000
3. Donoghue M, Hsieh F, Baronas E, Godbout K, Gosselin M, Stagliano N, Donovan M, Woolf B, Robison K, Jeyaseelan R: A novel angiotensin-converting enzyme-related carboxypeptidase (ACE2) converts angiotensin I to angiotensin 1-9. Circulation research, 87: e1-e9, 2000
4. Vickers C, Hales P, Kaushik V, Dick L, Gavin J, Tang J, Godbout K, Parsons T, Baronas E, Hsieh F: Hydrolysis of biological peptides by human angiotensin-converting enzyme-related carboxypeptidase. Journal of Biological Chemistry, 277: 14838-14843, 2002
5. Guy J L, Jackson R M, Acharya K R, Sturrock E D, Hooper N M, Turner A J: Angiotensin-converting enzyme-2 (ACE2): comparative modeling of the active site, specificity requirements, and chloride dependence. Biochemistry, 42: 13185-13192, 2003
6. Brosnihan K B, Li P, Ganten D, Ferrario C M: Estrogen protects transgenic hypertensive rats by shifting the vasoconstrictor-vasodilator balance of RAS. The American journal of physiology, 273: R1908-1915, 1997
7. Ferrario C M: ACE 2: More of Ang 1-7 or less Ang II? Current opinion in nephrology and hypertension, 20: 1, 2011
8. Chappell M C, Marshall A C, Alzayadneh E M, Shaltout H A, Diz DI: Update on the Angiotensin converting enzyme 2-Angiotensin (1-7)-MAS receptor axis: fetal programing, sex differences, and intracellular pathways. Frontiers in endocrinology, 4: 201, 2014
9. Wysocki J, Ye M, Rodriguez E, Gonzalez-Pacheco F R, Barrios C, Evora K, Schuster M, Loibner H, Brosnihan K B, Ferrario C M, Penninger J M, Batlle D: Targeting the degradation of angiotensin II with recombinant angiotensin-converting enzyme 2: prevention of angiotensin II-dependent hypertension. Hypertension (Dallas, Tex.: 1979), 55: 90-98, 2010
10. Batlle D, Wysocki J, Soler M J, Ranganath K: Angiotensin-converting enzyme 2: enhancing the degradation of angiotensin II as a potential therapy for diabetic nephropathy. Kidney international, 81: 520-528, 2012
11. Wysocki J, Garcia-Halpin L, Ye M, Maier C, Sowers K, Burns K D, Batlle D: Regulation of urinary ACE2 in diabetic mice. American Journal of Physiology-Renal Physiology, 305: F600-F611, 2013
12. Haber P K, Ye M, Wysocki J, Maier C, Haque S K, Batlle D: Angiotensin-Converting Enzyme 2-Independent Action of Presumed Angiotensin-Converting Enzyme 2 Activators: Studies In Vivo, Ex Vivo, and In Vitro. Hypertension (Dallas, Tex.: 1979), 63: 774-782, 2014
13. Serfozo P, Wysocki J, Gulua G, Schulze A, Ye M, Liu P, Jin J, Bader M, Myöhänen T, Garcia-Horsman J A: Ang II (angiotensin II) conversion to angiotensin-(1-7) in the circulation is POP (prolyloligopeptidase)-dependent and ACE2 (angiotensin-converting enzyme 2)-independent. Hypertension (Dallas, Tex.: 1979), 75: 173-182, 2020
14. Marquez A, Wysocki J, Pandit J, Batlle D: An update on ACE2 amplification and its therapeutic potential. Acta Physiol (Oxf): e13513, 2020
15. Wysocki J, Schulze A, Batlle D: Novel Variants of Angiotensin Converting Enzyme-2 of Shorter Molecular Size to Target the Kidney Renin Angiotensin System. Biomolecules, 9, 2019
16. Hoffmann M, Kleine-Weber H, Schroeder S, Kruger N, Herrler T, Erichsen S, Schiergens T S, Herrler G, Wu N H, Nitsche A, Muller M A, Drosten C, Pohlmann S: SARS-CoV-2 Cell Entry Depends on ACE2 and TMPRSS2 and Is Blocked by a Clinically Proven Protease Inhibitor. Cell, 2020
17. Walls A C, Park Y-J, Tortorici M A, Wall A, McGuire A T, Veesler D: Structure, function, and antigenicity of the SARS-CoV-2 spike glycoprotein. Cell, 2020
18. Wrapp D, Wang N, Corbett K S, Goldsmith J A, Hsieh C-L, Abiona O, Graham B S, McLellan J S: Cryo-EM structure of the 2019-nCoV spike in the prefusion conformation. Science, 367: 1260-1263, 2020
19. Lan J, Ge J, Yu J, Shan S, Zhou H, Fan S, Zhang Q, Shi X, Wang Q, Zhang L: Structure of the SARS-CoV-2 spike receptor-binding domain bound to the ACE2 receptor. Nature, 581: 215-220, 2020
20. Wang Q, Zhang Y, Wu L, Niu S, Song C, Zhang Z, Lu G, Qiao C, Hu Y, Yuen K Y, Wang Q, Zhou H, Yan J, Qi J: Structural and Functional Basis of SARS-CoV-2 Entry by Using Human ACE2. Cell, 2020
21. Davidson A M, Wysocki J, Batlle D: The interaction of SARS-CoV-2 and other coronavirus with Angiotensin Converting Enzyme 2 (ACE2) as their main receptor: therapeutic implications. Hypertension (Dallas, Tex.: 1979), 2020
22. Monteil V, Kwon H, Prado P, Hagelkruys A, Wimmer R A, Stahl M, Leopoldi A, Garreta E, Hurtado Del Pozo C, Prosper F, Romero J P, Wirnsberger G, Zhang H, Slutsky A S, Conder R, Montserrat N, Mirazimi A, Penninger J M: Inhibition of SARS-CoV-2 Infections in Engineered Human Tissues Using Clinical-Grade Soluble Human ACE2. Cell, 181: 905-913 e907, 2020
23. Zoufaly A, Poglitsch M, Aberle J H, Hoepler W, Seitz T, Traugott M, Grieb A, Pawelka E, Laferl H, Wenisch C: Human recombinant soluble ACE2 in severe COVID-19. The Lancet Respiratory Medicine, 2020
24. Haschke M, Schuster M, Poglitsch M, Loibner H, Salzberg M, Bruggisser M, Penninger J, Krähenbühl S: Pharmacokinetics and pharmacodynamics of recombinant human angiotensin-converting enzyme 2 in healthy human subjects. Clinical pharmacokinetics, 52: 783-792, 2013
25. Wan Y, Shang J, Graham R, Baric R S, Li F: Receptor recognition by the novel coronavirus from Wuhan: an analysis based on decade-long structural studies of SARS coronavirus. Journal of virology, 94, 2020
26. Morizane R, Bonventre J V: Generation of nephron progenitor cells and kidney organoids from human pluripotent stem cells. Nature protocols, 12: 195, 2017
27. Morizane R, Lam A Q, Freedman B S, Kishi S, Valerius M T, Bonventre J V: Nephron organoids derived from human pluripotent stem cells model kidney development and injury. Nature biotechnology, 33: 1193, 2015

28. Wu H, Uchimura K, Donnelly E L, Kirita Y, Morris S A, Humphreys B D: Comparative analysis and refinement of human PSC-derived kidney organoid differentiation with single-cell transcriptomics. Cell Stem Cell, 23: 869-881. e868, 2018
29. Liu P, Wysocki J, Serfozo P, Ye M, Souma T, Batlle D, Jin J: A Fluorometric Method of Measuring Carboxypeptidase Activities for Angiotensin II and Apelin-13. Sci Rep, 7: 45473, 2017
30. Liu P, Wysocki J, Souma T, Ye M, Ramirez V, Zhou B, Wilsbacher L D, Quaggin S E, Batlle D, Jin J: Novel ACE2-Fc chimeric fusion provides long-lasting hypertension control and organ protection in mouse models of systemic renin angiotensin system activation. Kidney international, 94: 114-125, 2018
31. Ye M, Wysocki J, Gonzalez-Pacheco F R, Salem M, Evora K, Garcia-Halpin L, Poglitsch M, Schuster M, Batlle D: Murine recombinant angiotensin-converting enzyme 2: effect on angiotensin II-dependent hypertension and distinctive angiotensin-converting enzyme 2 inhibitor characteristics on rodent and human angiotensin-converting enzyme 2. Hypertension (Dallas, Tex.: 1979), 60: 730-740, 2012
32. Gupta A K, Sarkar P, Wertheim J A, Pan X, Carroll T J, Oxburgh L: Asynchronous mixing of kidney progenitor cells potentiates nephrogenesis in organoids. Communications biology, 3: 1-11, 2020
33. Ichimura T, Mori Y, Aschauer P, Das K M P, Padera R F, Weins A, Nasr M L, Bonventre J V: KIM-1/TIM-1 is a Receptor for SARS-CoV-2 in Lung and Kidney. medRxiv, 2020
34. Matsuyama S, Nao N, Shirato K, Kawase M, Saito S, Takayama I, Nagata N, Sekizuka T, Katoh H, Kato F: Enhanced isolation of SARS-CoV-2 by TMPRSS2-expressing cells. Proceedings of the National Academy of Sciences, 117: 7001-7003, 2020
35. Poglitsch M, Domenig O, Schwager C, Stranner S, Peball B, Janzek E, Wagner B, Jungwirth H, Loibner H, Schuster M: Recombinant Expression and Characterization of Human and Murine ACE2: Species-Specific Activation of the Alternative Renin-Angiotensin-System. International journal of hypertension, 2012: 428950, 2012
36. Yan R, Zhang Y, Li Y, Xia L, Guo Y, Zhou Q: Structural basis for the recognition of SARS-CoV-2 by full-length human ACE2. Science, 367: 1444-1448, 2020
37. Su H, Yang M, Wan C, Yi L-X, Tang F, Zhu H-Y, Yi F, Yang H-C, Fogo A B, Nie X: Renal histopathological analysis of 26 postmortem findings of patients with COVID-19 in China. Kidney international, 2020
38. Wu H, Larsen C P, Hernandez-Arroyo C F, Mohamed M M, Caza T, Sharshir M d, Chughtai A, Xie L, Gimenez J M, Sandow T A: AKI and collapsing glomerulopathy associated with COVID-19 and APOL1 high-risk genotype. Journal of the American Society of Nephrology, 31: 1688-1695, 2020
39. Batlle D, Soler M J, Sparks M A, Hiremath S, South A M, Welling P A, Swaminathan S, Covid, Ace2 in Cardiovascular L, Kidney Working G: Acute Kidney Injury in COVID-19: Emerging Evidence of a Distinct Pathophysiology. J Am Soc Nephrol, 2020
40. Mina Shirazi J W M Y, Chad Haney, Ming Zhao, Yasphal Kanwar, Jenny Zhang Zheng and Daniel Batlle: Novel ACE2 truncate for acute kidney injury. ASN abstract, 2019
41. Kuba K, Imai Y, Rao S, Gao H, Guo F, Guan B, Huan Y, Yang P, Zhang Y, Deng W: A crucial role of angiotensin converting enzyme 2 (ACE2) in SARS coronavirus-induced lung injury. Nature medicine, 11: 875-879, 2005
42. Sodhi C P, Wohlford-Lenane C, Yamaguchi Y, Prindle T, Fulton W B, Wang S, McCray Jr P B, Chappell M, Hackam D J, Jia H: Attenuation of pulmonary ACE2 activity impairs inactivation of des-Arg9 bradykinin/BKB1R axis and facilitates LPS-induced neutrophil infiltration. American Journal of Physiology-Lung Cellular and Molecular Physiology, 314: L17-L31, 2018.

Example 2: A Novel Soluble ACE2 Variant with Prolonged Duration of Action Prevents SARS-CoV-2 Infection in Human Kidney Organoids Methods Design, production and purification of the short human ACE2 1-618 (hACE2(1-618)) and of the human ACE2 1-618 with an Albumin Binding Domain (ABD) tag (hACE2 (1-618)-ABD). The short variant of human ACE2 protein consisting of 618 amino acids (hACE2(1-618)) and hACE2 1-618 fused albumin-binding domain (ABD)(hACE2(1-618)-ABD were generated and tested as follows. The cDNA of human ACE2 was generated by PCR amplification using as a template human kidney cDNA library (Milipore). We used specific primers that determine the length of the short ACE2(1-618) cDNA to be amplified compatible with the expression vector restriction sites (pcDNA, Invitrogen, Carlsbad, CA, USA). The absence of mutations in the amplified cDNA was verified by sequencing. The plasmid with the inserted cDNA of the short ACE2 variant 1-618 was then expressed by stable transfection in human embryonic kidney cells (293 cell line) (see below).

An artificial gene encoding an ABDCon (a variant of ABD with improved albumin binding affinity (fM range), favorable biophysical characteristics and improved stability 12), with a flexible linker (G453) at its N-terminus from the ABDCon was prepared. The cDNA encoding the G4S3-ABDCon construct was fused to short ACE2(1-618) cDNA using a "sewing" PCR to produce the fusion chimera (hACE2(1-618)-ABD), in which the ABDCon was linked, via the G4S3 linker, to the ACE2(1-618) moiety at its the C terminal end. The cDNA of the fusion chimera ACE2(1-618)-ABD was then inserted into pcDNA6 plasmid (Invitrogen) using custom synthesized complementary primers (IDT) and the Gibson assembly kit (NEB). After verifying the DNA sequence of the pcDNA6 fused with the ACE2(1-618)-ABD, HEK293 cells were then transfected with the plasmid construct.

The hACE2(1-618) and hACE2(1-618)-ABD polypeptide variants were overexpressed, and their presence and size were verified in Western blot using a specific ACE2 antibody (Abcam, Ab38888). Enzyme activity was confirmed by the detection of fluorescence formation using an artificial ACE2 substrate Mca-APK (Dnp) in the culturing medium.

For large scale production and purification of the naked and ABD-tagged ACE2(1-618) polypeptides in stably transfected HEK cells, single clones were selected and expanded to large culture flasks. Conditioned serum-free medium from the selected clones of stably transfected 293 cells overexpressing the naked and ABD-tagged ACE2(1-618) polypeptides was concentrated on Centricon 70 centrifugal devices (cut off 30 kDa). The resulting retentate was cleared by centrifugation 23,000 g for 10 min at 4 C, subjected to anion exchange Q-sepharose followed by size exclusion chromatography on Superdex 200 pg. Eluted fractions were applied to SDS-PAGE, transferred to PVDF membrane and stained with Brilliant Blue to assess protein and screened for ACE2 activity using Mca-APK-Dnp substrate. Protein concentration in fractions containing ACE2 activity was determined using BCA assay (Pierce).

Generation of human kidney organoids. For staining studies, we used a set of human kidney organoids derived from human pluripotent stem cells (hPSC) as described (27). On day 3, once culture became ~50% confluent, culture medium was replaced with basic differentiation medium Advanced RPMI 1640 (ThermoFisher Scientific) and 1× GlutaMAX (ThermoFisher Scientific) containing 8 µM CHIR99021(Reprocell). On day 4, culture medium was replaced with basic differentiation medium containing 10 ng/ml Activin A (R&D Systems). On day 7, medium was replaced with basic differentiation medium containing 10 ng/ml FGF9 (R&D Systems). On day 9, differentiated kidney progenitors form renal vesicle like clusters in the wells of six-well plate. For asynchronous mixing of progenitors, directed differentiation was performed on two batches of H9 cells staggered 2 days apart. On day 9, the first batch of kidney progenitors were harvested with TrypLE Express (ThermoFisher Scientific) and resuspended at a density of 2.5×105 cells/pi in organoid initiation medium containing APEL2 (Stemcell Technologies), 1.5% PFHM-II (ThermoFisher Scientific), 100 ng/ml FGF9, 100 ng/ml BMP7 (R&D Systems), and 1 µg/ml Heparin (Sigma-Aldrich). In a 24-well plate, organoid initiation medium was added (1 ml/well) and an air-liquid interface was created by suspending isopore membranes (EMD Millipore) at the surface of the medium. Resuspended kidney progenitors were aggregated on top of the filter (2 µl/aggregate). On day 11, aggregated cells were gently dissociated into small cell clusters with a 200 µl micropipette and mixed with second batch of newly differentiated kidney progenitor cells. One dissociated aggregate was mixed with 5×105 kidney progenitor cells in 4 µl of organoid initiation medium and re-aggregated again in two aggregates at the air-liquid interface. Medium was changed every 48 h or when it turned yellow. On day 13, all growth factors were removed from the medium and organoids were cultured for the next 5 days with APEL2 containing 1.5% PFHM-II.

In vitro assay for detection of hACE2-RBD interaction. Using an artificial ACE2 substrate, Mca-APK-Dnp (10 µM) (Bachem), ACE2 activity of hrACE2(1-740) was not affected by the presence of recombinant glycosylated RBD (aa 319-541, RayBiotech) in a 0.001 to 100 ng/ml concentration range. Purified His-tagged RBD protein (aa 319-541, RayBiotech) was dissolved in Tris-buffered saline (TBS) pH 7.4 and loaded into 96-well Ni-coated black plate (ThermoFisher) (100 µL/well) for binding. TBS alone (100 ul/well) was loaded to blank wells. After incubation for 1 hr at room temperature, five washes were done using 200 µL of TBS supplemented with 0.05% Tween20 (wash buffer). 100 µL of hrACE2(1-740) (positive control), and mouse rACE2 (negative control) were added to the wells and incubated for 1 hour at room temperature at concentrations ranging from 1000 ng/ml to 6.25 ng/ml. Afterwards, wells were washed 5 times using 2004, of wash buffer for each wash. Finally, Mca-APK-Dnp substrate (1 µM final concentration) was added and fluorescence formation was measured in microplate fluorescence reader FLX800 at 320 nm using excitation and 400 nm emission filters.

Dose dependent binding of enzymatically active human rACE2 protein to the RBD-His protein immobilized onto the Ni-coated microplate was confirmed by concentration-dependent increase in fluorescence formation (expressed in relative fluorescence unit—RFU) from the cleavage of the Mca-APK-Dnp ACE2 substrate. There was no increase in RFU in negative control wells, i.e. coated with mrACE2 at any tested concentration (from 1000 ng/ml to 6.25 ng/ml) as well as in wells not coated with RBD (TBS only).

We used lysates of isolated cytosol, nuclear or membrane fractions (Invent Biotechnologies, Inc, Plymouth, MN, USA) from human kidney organoids to assess binding of soluble hACE2 variant polypeptide agents from those isolated fractions to the RBD domain of SARS-CoV-2 S1 protein. Purified His-tagged RBD protein (aa 319-541, RayBiotech) was dissolved in Tris-buffered saline (TBS) pH 7.4 and loaded into 96-well Ni-coated black plate (ThermoFisher) (100 µL/well) for binding for 1 hour. After five washes with 200 µL of wash buffer, the described above organoid tissue lysate samples (10 uL) were diluted in 90 µL TBS, pH 7.4, and applied in a total volume of 100 µL loaded onto the plate and left for 1 hr at room temperature. Afterwards, wells were washed 5 times using 200 µL of wash buffer for each wash. Finally, Mca-APK-Dnp substrate (1 µM final concentration) was added and fluorescence formation was measured in microplate fluorescence reader FLX800 at 320 nm using excitation and 400 nm emission filters. The organoid tissue lysates on wells without His-tagged RBD protein coating did not produce any measurable fluorescence at otherwise the same assay conditions. The measured fluorescence in organoid lysates was corrected for total protein content (measured using BCA Protein Assay Kit, ThermoFisher) and converted to a concentration of ACE2 protein by reference to a standard curve of recombinant ACE2 (R&D Systems) assayed under the same conditions.

Results

Catalytic Efficiency of Human ACE2(1-618) and Human ACE2(1-618) with an ABD tag. The catalytic efficiency to form Phenylalanine (Km/Kcat M-1*s-1) from Ang II was essentially the same for ACE2(1-618) (n=4) and ACE2(1-618)-ABD (n=4) (1.44±0.09 and 1.63±0.36, respectively) and slightly lower but not significantly than that of ACE2 (1-740) (n=4) (2.00±0.31).

Using the same assay, we found that all three of hACE2 (1-740) (positive control), truncated variant hACE2(1-618), and stabilized truncated variant hACE2(1-618)-ABD were able to generate Phenylalanine from des-9Arginine. Catalytic efficiency was slightly but significantly higher for hACE2(1-618)-ABD (n=6) (1.45±0.14 M-1*s-1), than for hACE2(1-740) (n=6) (0.69±0.15 M-1*s-1 (p=0.002)) or the naked truncated hACE2(1-618) (n=6) (0.94±0.15 M-1*s-1) (p=0.023).

Prolonged in vivo activity of human ACE2(1-618)-ABD variant polypeptide. The elimination phase duration of action and the mean residence time were markedly longer for the ABD-tagged ACE2(1-618) (25.7±4.1 hours) compared to the naked ACE2(1-618) polypeptide (3.2±0.6 hours) and the non-truncated ACE2(1-740) polypeptide (6.8±1.0 hours) (p<0.001). These results confirm a marked extension of in vivo duration of action of ACE2(1-618) achieved by adding the ABD tag.

Example 3: Fusion of Novel Soluble ACE2 Variant Provides Extended Duration of Action The present disclosure teaches that duration of action of truncated soluble human ACE2 polypeptides can be achieved by fusion with certain other polypeptide moieties.

Figure 6:
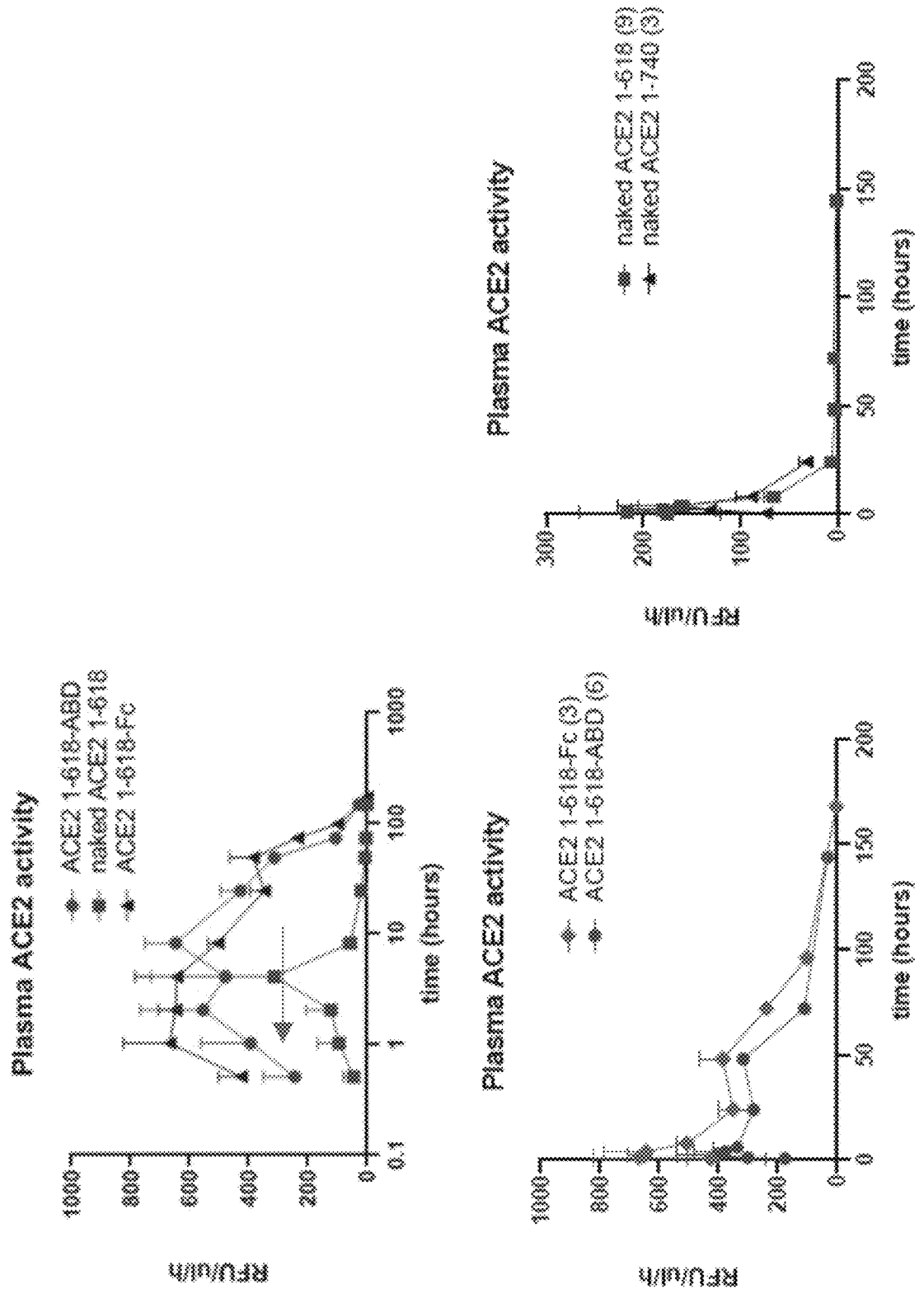
FIG. 6. ACE2 618-Fc and ACE2 618-ABD proteins still retained substantial ACE2 activity between 72 and 96 hours (3-4 days) after i.p. injection (see arrow) (bottom left panel) The ACE2 618 variant and ACE2 740 do not result in any plasma activity after 7 or 8 hours. (bottom right panel).

The present Example documents an extended duration of action by fusion of hACE2(1-618) with either Fc or ABD, specifically demonstrating of at least 3 days as demonstrated by persistence of ACE2 enzymatic activity in plasma for a period of at least 3 days (see FIG. 6).

As noted herein, the present disclosure teaches particular utility of such extended-duration-of action variants for treatment of infection with SARS-CoV-2. Furthermore, the present specification teaches that smaller soluble ACE2 variant polypeptides, and particularly those small enough to avoid filtration by the kidneys, may be further particularly useful for treatment of SARS-CoV-2 infection, especially in certain subjects.

Example 4: Characterization of ACE2 Variants in Mice

Figure 7:
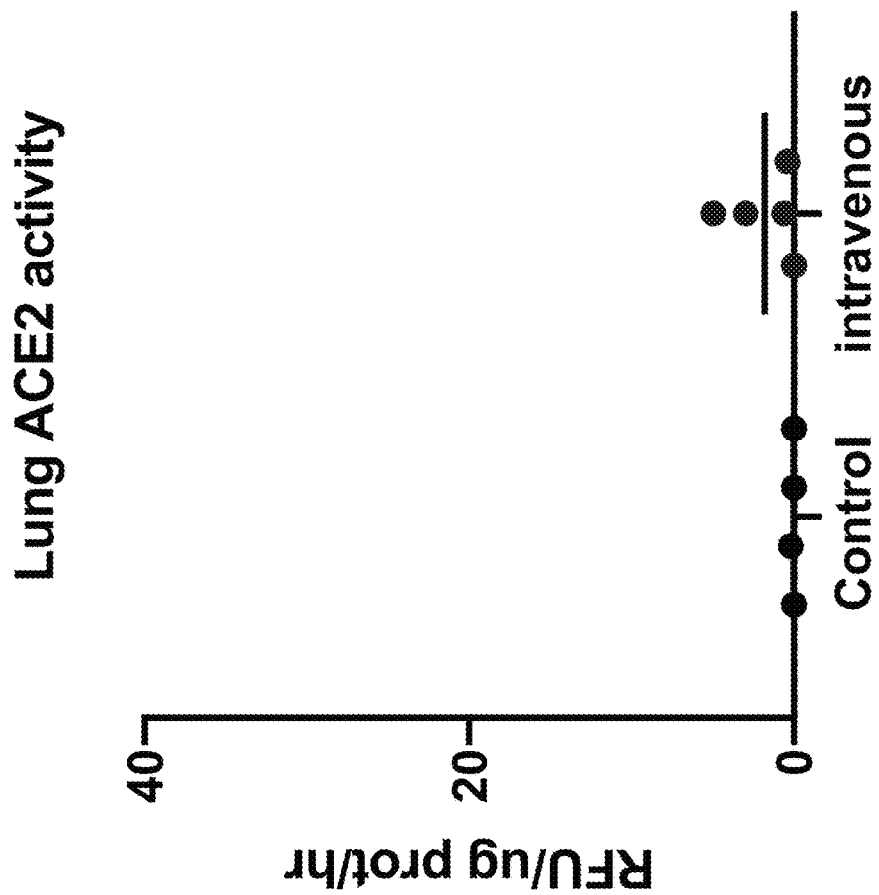
FIG. 7. ACE2 deficient mice were injected i.v. 1 ug/g BW of human rACE2(1-618)-ABD. After 1 hour from delivery, mice were euthanized and perfused with PBS to flush out blood from the organs. ACE2 deficient mice that were not injected served as controls. The graph shows ACE2 activity in total cell lysate of the lungs corrected per total protein content. The intravenous route had only a very marginal increase in lung ACE2.

ACE2 deficient mice were injected i.v. with 1 μg/g BW of hACE2(1-618)-ABD. After 1 hour from delivery, mice were euthanized and perfused with PBS to flush out blood from the organs. ACE2 deficient mice that were not injected served as controls. FIG. 7 shows ACE2 activity in total cell lysate of the lungs corrected per total protein content. The intravenous route had only a very marginal increase in lung ACE2.

Figure 8:
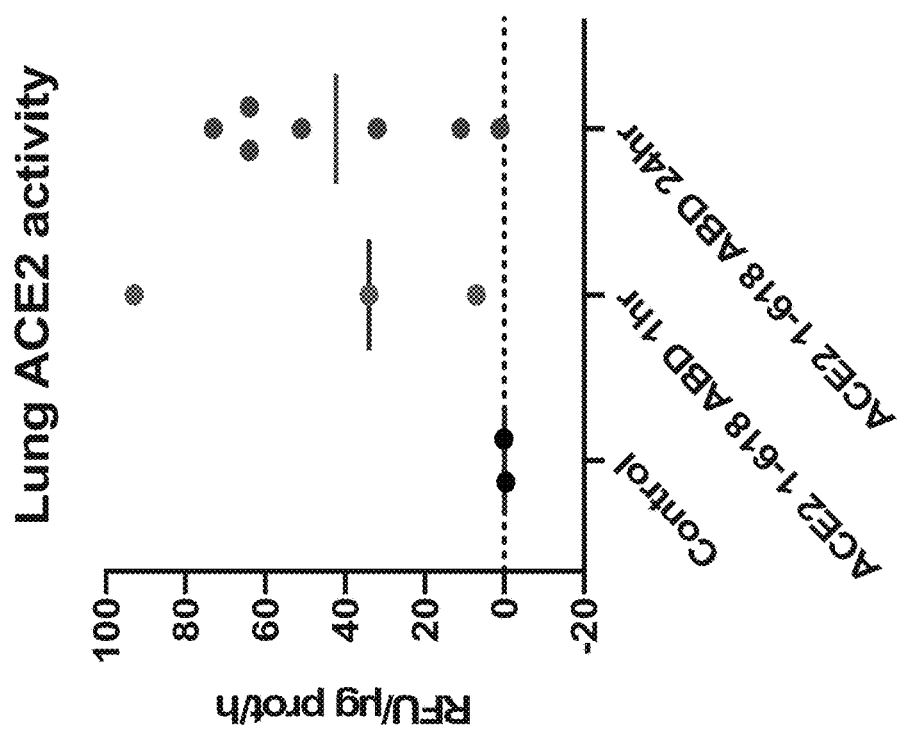
FIG. 8. Wild-type mice were given intranasally 1 or 2 μg/g BW of hrACE2(1-618)-ABD. One hour or 24 hours later, mice were euthanized and perfused with PBS to flush blood out of the organs. Mice that were vehicle treated (PBS) served as controls. The graph shows substantial ACE2 activity increase in total cell lysate of the lungs corrected per total protein content both, 1 hour and 24 hours after hrACE2 (1-618)-ABD.
Figure 9:
FIG. 9. ACE2KO mice lungs were stained with anti-human ACE2 and anti-TMPRSS2 antibody. ACE2(1-618)-ABD (1 μg/g BW) was given intranasally. Mice were euthanized 24 hours after delivery and perfused with PBS to flush blood out of the organs. The presence of ACE2 staining after ACE2(1-618)-ABD given intranasallay is documented in a KO model that normally has no ACE2 whatsoever.
Figure 10:
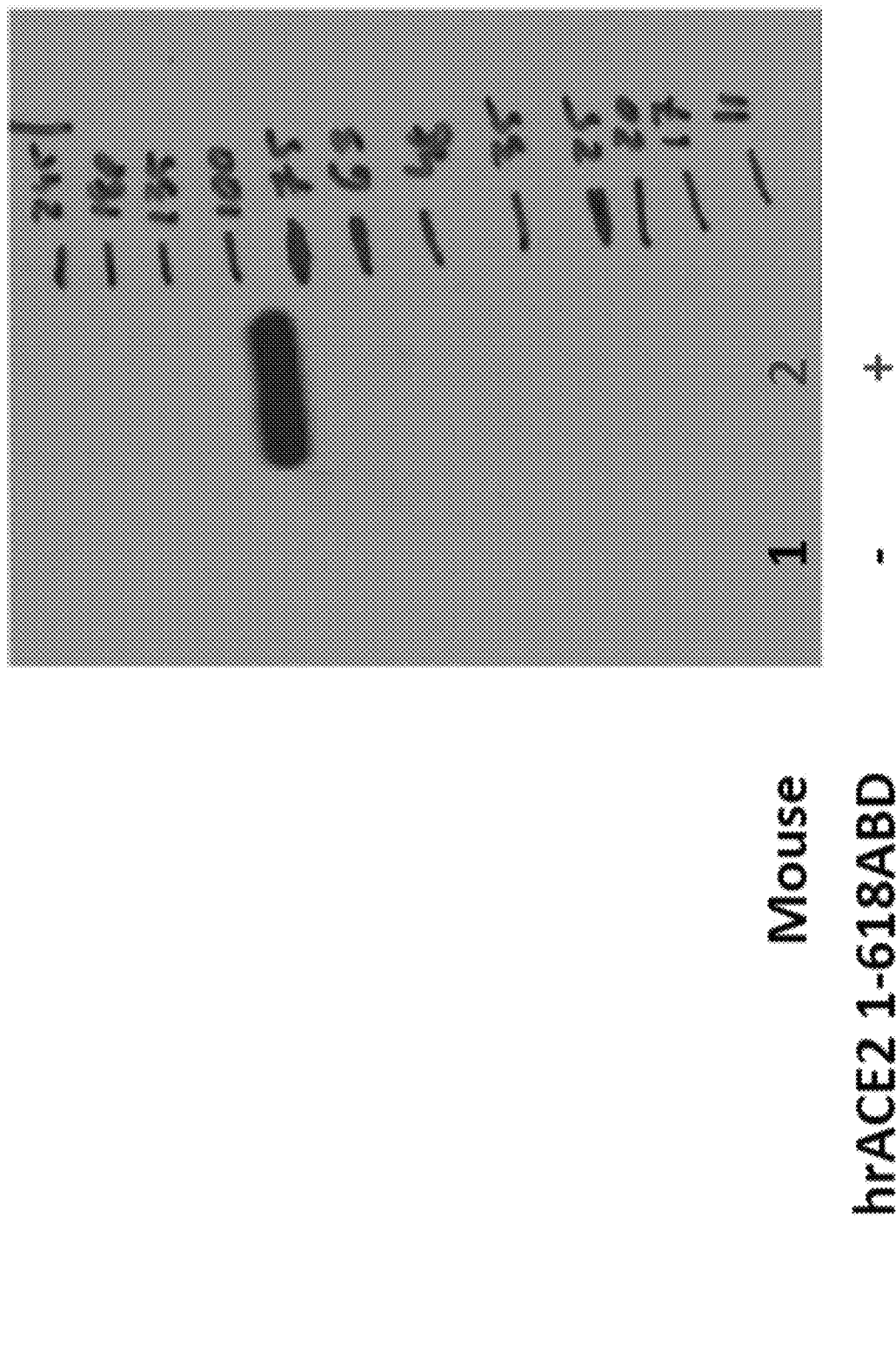
FIG. 10. Wild-type mice were given either 2 μg/g BW ACE2(1-618)-ABD-6His or PBS (vehicle control) intranasally for lung delivery. 1 hour after delivery, mice were euthanized and perfused with PBS to flush blood out of the organs. This example shows that using an anti-His-antibody, by Western blot an ACE2 band is present in lungs from a mouse given intranasally ACE2 1618-ABD-His (mouse number 2) but not in a control mouse (mouse number 1).

Wild-type mice were given rACE2(1-618)-ABD intranasally at doses of either 1 or 2 μg/g BW. One hour or 24 hours later, mice were euthanized and perfused with PBS to flush blood out of the organs. Mice that were vehicle treated (PBS) served as controls (black). The graph in FIG. 8 shows substantial ACE2 activity increase in total cell lysate of the lungs corrected per total protein content both, 1 hour and 24 hours after hACE2(1-618)-ABD.

The present Example thus documents, as described herein, that hACE2(1-618)-RBD can be effectively administered to, and active in, the lungs.

Example 5: Combined Decoy Effect and Protective Activity of Soluble Human ACE2 Variant Polypeptide Agents Introduction While lung injury is the principal manifestation of severe COVID-19, AKI is also a main complication that is associated with mortality as high as 30-70%. Like for SARS-CoV, the main receptor for SARS-CoV2 entry into host cells is tissue-bound, full-length (FL) angiotensin-converting enzyme 2 (ACE2). In its FL form, ACE2 has a transmembrane domain that anchors it to the cell plasma membrane. Current thinking is that the main entry sites for SARS-CoV2 are nasal goblet cells and lung type II pneumocytes which express both FL-ACE2 and TMPRRS2, a protease needed to facilitate cell entry of the activated SARS-CoV2-ACE2 complex.

The SARS-CoV2 exhibits high affinity for human but not murine FL-ACE2. Consistent with this, inoculation of SARS-CoV to wild type mice had little effect whereas in transgenic mice expressing human FL-ACE2 the mortality rate is very high.

Without wishing to be bound by any particular theory, we propose that infection with SARS-CoV2 results in internalization and loss of membrane bound FL-ACE2, resulting in impaired degradation of its substrates namely Ang II and des 9Arg bradykinin. We further propose this impaired degradation, coupled with activation of Ang II by the inflammatory and stress response to viral infection, is apt to foster organ injury.

The present disclosure provides an insight that administration of soluble, active ACE2 should have particular therapeutic benefit in the treatment of SARS-CoV-2 infection, both through its action as a decoy to interfere with viral infectivity and through its ability to restore ACE2 the altered balance of angiotensin II and bradykinins that ensues with depletion of the FL-ACE2 enzyme. Furthermore, the present disclosure teaches that administration of small, soluble, active ACE2 variants may be particularly useful, especially if they are sufficiently small to be filterable in the kidney.

Among other things, the present Example describes studies to delineate and/or distinguish separate mechanisms of action for soluble hACE2 variant polypeptides through (i) action as a decoy that binds SARS-CoV-2 and limits viral update that occurs when the virus interacts with membrane-bound FL-ACE2; and (ii) restoration of depleted ACE2 activity.

The present Example further assesses various modes of administration—including for example (i) via minicircle DNA delivery (which provides unlimited supply of soluble ACE2 to circulation); or (ii) directly to the lung by Adeno associated viral vectors (AAV), and considers protection against SARS-CoV2 infection and/or its associated organ damage.

As described herein, we have developed soluble ACE2 variant polypeptides that have the advantage of being shorter than natural soluble ACE2, which is a large protein of 740 amino acids that naturally occurs as a dimer (>200 kDa) and therefore is not filterable by the kidney. We have described a truncated soluble mouse ACE2 variant of 619 amino acids (mACE2(1-619)) that is filterable and enhances local Ang 1-7 formation and prevents Ang II accumulation as a way to confer organ protection, including kidney as we demonstrated in an acute kidney injury (AKI) model. We describe herein a human counterpart to mACE2(1-619), which is also a truncated soluble ACE2 variant polypeptide, in this case of 618 amino acids (hACE2(1-618)). This human variant, unlike the mouse variant, has the binding site for the receptor binding domain of SARS-CoV2 S spike.

Furthermore, as also described herein, we have also invested effort in extending the duration of action of soluble ACE2 variant polypeptides, and specifically of this truncated human ACE2(1-618) variant; we have demonstrated extension from hours to days—significantly enhanced therapeutic potential.

The present Example describes further characterization of useful soluble ACE2 polypeptide variants, and particularly of small (e.g., truncated) variants, moreover including fusion polypeptides in which a tag is added to such truncated soluble variant, which the resulting fusion polypeptide retaining solubility and activity (and desirably susceptibility to kidney filtration), and moreover achieving prolonged duration of activity.

Among other things, the present Example describes characterization in a mouse model, including to document both reduced infectivity and provision of sufficient ACE2 enzymatic activity to attenuate lung and kidney injury.

Specific aims of the present Example include:
(1) providing assessments for characterizing soluble ACE2 variant polypeptide agents as described herein with respect to:
  (a) prevention of SARS-CoV2 infectivity in permissive cells and human kidney organoids; and
  (b) effectiveness upon administration by various routes, such as (i) minicircle DNA delivery (ii) AAV delivery to the lungs and (iii) administration of soluble recombinant polypeptide
(2) elucidating contribution of two main mechanisms whereby soluble hACE2 polypeptide variants provided herein are protective: (i) the decoy effect versus (ii) the effect attributable to provision of ACE2 enzymatic activity, which in itself may attenuate acute lung and kidney injury;

(3) assessing SARS-CoV2 infection in older mice of both sexes, mice with AM, diabetes, obesity and hypertension as a way to mimic known risk factors for COVID-19 and characterize provided soluble hACE2 variant polypeptide agents with respect to these risk factors (e.g., as proxies for certain patient populations such as, for example, people of older age, males, etc. and/or people with AKI, diabetes, obesity and/or hypertension); this work will be done using models where human FL-ACE2 is introduced via AAV or minicircle DNA delivery to render them susceptible to SARS-CoV2 infection, and then assess the efficacy of soluble hACE2 variant polypeptide agents as described herein.

Significance

Lung injury is the principal manifestation of severe COVID-19 disease. In recent months it has been clear that Acute Kidney Injury (AKI) is also a main complication that is associated with mortality as high as 30-70% [1-13].

Angiotensin converting enzyme 2 (ACE2) was discovered 20 years ago and studied extensively in terms of physiologic and preclinical studies that had mainly centered on its enzymatic properties as a monocarboxypeptidase that cleaves Angiotensin (Ang) II to form Ang 1-7, and its effect on other substrates [14-27].

Figure 11:
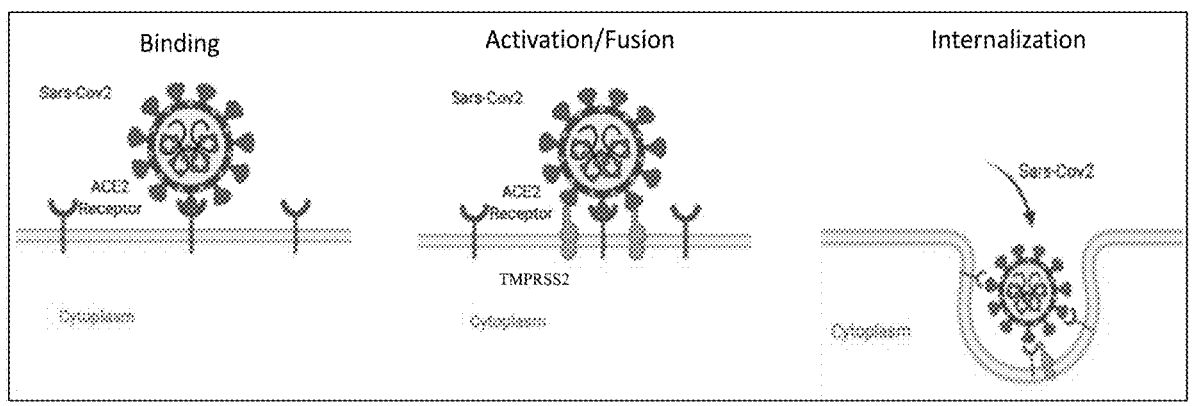
FIG. 11. SARS-CoV2 binds to FL-ACE2 and after priming by the serine protease TMPRSS2 is activated and then internalized. In the process it is believed that FL-ACE2 decreases from the membrane. (from Davidson, Wysocki and Batlle, Hypertension 2020) (60).

SARS-CoV2, like SARS-CoV and other selected coronaviruses (as well as certain other viruses, such as Dengue virus, use membrane bound full length ACE2 (FL-ACE2) as their main receptor [28-35]. After binding of SARS-CoV2 S spike to the FL-ACE2 there is priming by a protease called TMPRSS2 that is needed for the fusion and internalization of the ACE2-viral spike complex (FIG. 11). In the process, it is believed that a state of deficiency of the membrane bound FL-ACE2 ensues and this fosters lung injury [36-40].

Normally the FL-ACE2 enzymatic functions protect against organ injury largely as a result of cleavage and thus disposal of Ang II and formation of Ang 1-7 [40, 41]. In addition, ACE2 degrades des-arg$^9$ bradykinin (BK 1-8); deficiency of ACE2 can thus lead to accumulation of des-arg$^9$ bradykinin (BK 1-8), and its attendant proinflammatory effects [41-45].

Without wishing to be bound by any particular theory, we propose that internalization of FL-ACE2 pursuant to viral infection results in loss of ACE2 acting as a guardian to prevent excessive levels of peptides with proinflammatory effects, which in turn can damage not only the lungs but also other organs like the kidneys, which are prone to local injury. The present disclosure provides soluble ACE2 variant polypeptides with ACE2 activity and teaches that they are particularly useful in preventing and treating SARS-CoV2 infection.

The present Example describes studies to develop animal data that can provide key gain mechanistic insights relevant to characterization and/or development of therapies based on soluble ACE2 protein administration and their impact on the RAS and Bradykinin cascades as well as organ function.

Furthermore, we propose that intravenous administration is unlikely to be as effective as intranasal administration which facilitates direct delivery to the nose and the lungs which are the presumed viral entry sites.

Still further, we appreciate that the duration of action of natural human ACE2 moreover is only a few hours [21, 48], and we suggest that therapeutic strategies that rely upon such natural human ACE2 may be hindered by challenges of effective administration. The present disclosure teaches, among other things, that variants with extended duration of action may be particularly useful for treatment as described herein.

We have generated a novel shorter variant of soluble mouse ACE2 that is filterable by the kidney and markedly attenuates AKI in the ischemia-reperfusion model [24, 49]. We herein provide a truncated soluble human variant, and furthermore certain stabilized forms thereof (e.g., fused with Fc or with an ABD), and demonstrate certain desirable attributes of each.

Of particular interest, we provide a truncated soluble hACE2 variant with extended duration of action that is sufficiently small to be filterable by kidneys. Exemplified herein is such a variant, termed hACE2(1-618)-ABD, in which the hACE2(1-618) truncated soluble polypeptide is fused with an albumin binding domain (ABD) that is only 5 kDa in size; this hACE2(10618)-ABD polypeptide has an extended duration of action (days) and is filterable by the kidneys. Without wishing to be bound by theory, we propose that this variant will provide ease of administration and sustained high levels to prevent viral escape. In some embodiments, we specifically propose administration via the intranasal route.

Among other advantages, strategies described herein may permit administration by patients themselves, for example if they may have been recently exposed or infected, and/or by medical personnel who encounter patients exposed to or infected with (or at risk of either), for example, in hospitals, in clinics, in doctor's offices, or even in the community.

Also specifically contemplated is administration to patients in whom infection is established, including in some embodiments in whom infection is progressing so that the patient is suffering from or, in the exercise of sound medical judgement is deemed to be at risk of, serious complications such as respiratory and/or kidney failure. Particularly in such patients, it may be desirable to administer agents as described herein intravenously rather than, or in addition to via pulmonary (e.g., aerosol) delivery. Alternatively or additionally, particularly in such patients, it may be desirable to administer provided agents in combination with one or more other agents and/or other therapeutic modalities. To give but a few examples, in some embodiments, it may be desirable to administer agents as described herein together with therapies that target a different aspect of viral life cycle (e.g., viral replication) and/or a subject's response (e.g., inflammation) to viral infection. Alternatively or additionally, in some embodiments, it may be desirable to combine administration of provided agents with other therapies (e.g., anti-spike antibody therapies) that also target the spike protein-ACE2 interaction, for example so that less of a provided soluble ACE2 variant polypeptide agent may be required to inhibit viral infection, and more may be available to provide ACE2 activity.

These inducible models will facilitate the study of SARS-CoV2 infection as a way to replicate high risk and severity of COVID-19 such as in people of older age, males, and with AKI, diabetes, obesity and hypertension.

Innovation

Our lab developed soluble mouse ACE2 variants with a smaller molecular size (~70 kD) than the natural soluble ACE2, which is a dimer (2×110 KD), which renders them filterable by the kidney [24]. We have shown that these shorter mouse ACE2 variants are capable to increase ACE2 activity and foster Ang 1-7 formation within the kidney exerting a protective effect in the AKI model of ischemia reperfusion [24, 49]. The present disclosure teaches particular usefulness of such small soluble ACE2 variants, and for the first time provides comparable such variants of human ACE2 protein.

Moreover, the present disclosure teaches particular usefulness of extended-duration-of-activity variants of soluble ACE2 proteins, and documents that fusion with particular moieties, such as Fc or ABD, can achieve surprising and significant extended duration of activity.

Still further, the present disclosure teaches that combination of small size and extended duration of activity provides particular significant benefits in the context of viral infection.

Figure 12:
FIG. 12. In vivo image of a WT C57BL/6 mouse with AKI infused with radiolabeled ACE2 1-619-ABD microSPECT is overlaid on microCT in mice injected with $^{99m}$Tc labeled purified ACE2 1-619-ABD. Activity in the kidney was calculated at 9% relative to the whole body. White arrows show the renal uptake. This AKI model has only one kidney.

Among other things, the present Example teaches that small active variants of ACE2, fused to a small (e.g., about 3-5 kDa) tag moiety can be characterized by each of (i) maintained activity; (ii) extended duration of activity; (iii) ability to interfere with viral infection; and (iv) glomerular filtration. For example, FIG. 12 shows kidney delivery via glomerular filtration in a mouse, as demonstrated using advanced radio imaging, of an active soluble ACE2 variant polypeptide agent as described herein—specifically mACE2 (1-619)-ABD. As described herein, such kidney delivery may be an advantage to treat AKI which is frequently associated with COVID-19.

Still further, the present Example teaches that certain provided active soluble ACE2 variants described herein, in addition to features (i)-(iv) noted in the preceding paragraph, are characterized in that, unlike certain other strategies for treating AKI (e.g., blockade of the AT1 receptor, for example using telmisartan), they do not lower blood pressure. This is clearly a safety feature for AKI particularly for those in intensive care units and often associated with hypotension.

Thus, the development and use of truncated soluble human ACE2 variants with extended duration of action as described herein to treat SARS-CoV-2 infection is highly innovative aspect and has clear preventative and therapeutic potential for COVID-19 and associated pulmonary and kidney complications.

Soluble ACE2 proteins by binding to SARS-CoV-2 and acting as a decoy can limit viral uptake by the membrane-bound FL-ACE2. Consequently, SARS-CoV-2 entry into the cells and subsequent viral replication can be reduced or prevented. The present disclosure additionally teaches that, even if the decoy effect is insufficient or is applied too late in the course of the disease the enzymatic effect still can be organ protective. Moreover, the present disclosure identifies and provides certain agents particularly useful to achieve these results, including specifically small (e.g., small enough for glomerular filtration), active, soluble polypeptides with extended duration of action. Of particular interest are variants that are or include human ACE2(1-618).

We also have tagged hACE2(1-618), as well as the non-truncated human soluble ACE2(1-740) with Fc (fragment crystallizable) [50]. The Fc fusion confers longer duration of ACE2 activity but then the size becomes very large and not suitable for kidney delivery via glomerular filtration. Still, this provided variant should be very effective in enhancing the decoy effect of soluble ACE2 [51].

Our hACE2(1-618) tagged with ABD (i.e., hACE2(1-618)-ABD is significantly smaller than the hACE2(1-618)-Fc variant. Moreover, after intranasal instillation, it remains for an extended time-period in the pulmonary space. Delivery of soluble ACE2 protein to the lung is most desirable to intercept the SARS-CoV-2 from binding to FL-ACE2 which is located in target type II pneumocytes. These cells isolated from COVID-19 patients express FL-ACE2 and also TMPRSS2 which explains the cell entry and subsequent viral replication [52].

Provision of a soluble ACE2 variant polypeptide agent as described herein via aerosol should not only be able to intercept the binding of SARS-CoV-2 to FL-ACE2 but also improve the altered angiotensin and bradykinin profile in the lungs associated with the ACE2 deficiency that supposedly occurs from ACE2 internalization (FIG. 11).

The present Example describes studies to dissect out relative contributions of the decoy versus the enzymatic effect of administering soluble active ACE2 polypeptide variants as described herein. This will be done by administering mouse soluble ACE2 that has enzymatic activity but cannot intercept SARS-CoV-2 from binding to the human FL-ACE2 but still may protect against organ injury due to its enzymatic properties. We also will generate and characterize mouse models expressing human FL-ACE2, by means of intranasal adeno associated viral (AAV) vectors and minicircle DNA delivery. These approaches will allow to introduce human FL-ACE2 efficiently and thus create in a matter of days, without lengthy cross-breeding, permissive mouse models of diabetes, obesity and hypertension that in humans confer risk for severe COVID-19. The current pandemic will hopefully subside soon but the reemergence of same or related coronavirus is likely and would benefit from additional insights into the therapeutic role of soluble ACE2 proteins as an effective and innovative therapy.

Approach

Confirmation that that SARS-CoV2 infectivity in permissive cells and human kidney organoids is prevented by active soluble hACE2 variant polypeptide agents as described herein.

Active soluble hACE2 variant polypeptide agents are assessed in a quantitative ACE2-RBD binding assay. Exemplary polypeptides for assessment and/or comparison as described herein are presented in Table 1 (where the term "native" refers to a soluble ACE(1-740) polypeptide, e.g., as is generated in nature, though those skilled in the art will appreciate in context that recombinant ACE(1-740) may, and typically will, be utilized.

TABLE 1

Characteristics of human ACE2 proteins

| ACE2 form | Amino acid residues | Dimerization | Extended Half-life | Predicted Molecular size in native state |
|---|---|---|---|---|
| Full-length ACE2 | 1-805 | Yes (within ACE2) | N/A | >200 kDa |
| Native soluble ACE2 | 1-740 | Yes (within ACE2) | No | >200 kDa |
| Naked short soluble ACE2 | 1-618 | No | No | ~70 kDa |
| ABD-tagged Short soluble ACE2 | 1-618 + ABD | No | Yes | ~75 kDa |
| Fc-tagged short soluble ACE2 | 1-618 + Fc | Yes (within Fc) | Yes | >190 kDa |
| Fc-tagged native soluble ACE2 | 1-740 + Fc | Yes (within ACE2 and Fc) | Yes | >250 kDa |

Each of the polypeptides noted in Table 1 have the receptor binding site for the S spoke protein because they each contain the entire peptidase domain (aa 19-615); we have also confirmed binding using our RBD-ACE2 binding assay as described herein.

Of particular interest, as described herein, are shorter variants with extended half-life (or otherwise with extended duration of action), and especially those that are small enough for glomerular filtration.

We further note that the hACE(1-618) truncation is not only shorter than the natural non-truncated hACE2(1-740), but also lacks dimerization; dimerization of hACE2(1-740) doubles its molecular size (and may have even more significant effects on globular size). Fusion of an Fc to non-truncated hACE2(1-740) can extend its duration of action; plasma ACE2 activity with native ACE2 fused with Fc about a week [50], as compared with only a few hours for the naked hACE2(1-740). The use of an Fc tag, however, could prove deleterious, for example via viral antibody-like dependent enhancement (ADE) such that soluble ACE2-Fc bound to the virus might potentially help the virus infect cells such as macrophages that express high levels of Fc receptor (FcR) [58, 59].

It must be noted that the natural, non-truncated soluble ACE2(1-740), and also our naked truncated hACE2(1-618) variant, have a half-life of few hours only [24, 48]. However, hACE2(1-618)-ABD can achieve sustained high ACE2 activity in plasma 3 to 4 days after a single IP injection (FIG. 13).

Characterization of Soluble ACE2 Variant Polypeptide Agents

Binding Studies. In some embodiments, characterization of active, soluble ACE2 variant polypeptide agents as described herein may involve binding studies to assess affinity for viral S1 glycoprotein. Studies may be performed using either a pseudovirus or live virus. In some embodiments, binding may be assessed, for example, by incubating virus or pseudovirus with active, soluble ACE2 variant polypeptide agent for a period of time (e.g., 1, 2, 3, 4, 5, 6, 7, 8, 9, 10 or more hours, or 1, 2, 3, 4, 5 or more days; in some embodiments within a range of about 1 day to about 3 days, in some embodiments about 3 days), and then contacted with susceptible cells (e.g., HEK cells expressing human ACE2, referred to herein as HEK-hACE2 cells). Relevant positive and/or negative controls may also be performed. FIG. 14 presents results of such an assessment of hACE2(1-618) and hACE2(1-618)-ABD variants described herein, with hACE2(1-740) as a positive control and mACE2(1-74) as a negative control. As can be seen, each of hACE2(1-618) and hACE2(1-618)-ABD variants described herein, with hACE2(1-740) completely suppressed pseudovirus infection of HEK-hACE2 cells; mACE2(1-740), which does not bind well to the SARS-CoV-2 spike protein, was unable to materially impede infection.

Alternatively or additionally, in some embodiments, assessment of affinity for viral S1 glycoprotein may involve performance of an assay in which a polypeptide that comprises a His-tagged spike protein RBD is immobilized on a substrate (e.g., Ni-coated 96-well plates); and capture of a provided active, soluble ACE2 variant polypeptide agent is detected and/or quantified. As with various other assays described herein, in some embodiments, extent of binding (e.g., specific binding) by a particular assessed agent may be compared with appropriate positive and/or negative controls and/or may be considered relative to that of other assessed provided agents; in some such embodiments, an assessed agent shows binding at least comparable to that observed for hACE2(1-740), under conditions where mACE2(1-740) does not bind significantly. Alternatively or additionally, in some embodiments, tissues from hACE2 TG and WT mice may be employed.

Still further alternatively or additionally, in some embodiments, a biophysical binding assay may be utilized to determine the affinity constant ($K_D$) that characterizes the binding of a provided active, soluble ACE2 variant polypeptide agent to the viral spike protein and/or to compare $K_{DS}$ of various provided agents with one another and/or with the soluble human ACE2(1-740).

Still further alternatively or additionally, in some embodiments, proximity AlphaLISA may be utilized to assess binding.

Moreover, in some embodiments, a plurality of different approaches may be utilized to assess binding of one or more variants, including optionally relative to one another and/or to an appropriate reference (e.g., positive and/or negative control). For example, in some embodiments, a plurality of different strategies will be used to assess binding (e.g., to determine affinity constants and/or inhibitory constants provided agents as described herein).

In many embodiments, binding assessments (and/or other studies described herein)will involve determining binding at a plurality of concentration points.

Neutralization Studies. In some embodiments, characterization of active, soluble ACE2 variant polypeptide agents as described herein may involve one or more neutralization studies. For example, in some embodiments, one or more of Monkey kidney Vero E6 cells and/or HEK-hACE (i.e., HEK cells that we transfected with full length hACE2 (hFLACE)) will be used; in many embodiments, non-permissive cells (e.g., non-transfected or mock transfected HEK cells) will be used as a control. In a representative assay, for example, cells will first First, cells will be exposed to pseudoviral particles (coated with S1 spike protein from SARS-CoV-2) or to SARS-CoV-2 live virus. The optimal dose of each soluble protein for neutralization will be determined in comparative studies. Cells will be seeded onto 96-well plates (5*104 cells per well). After growing for 24 hours in complete medium, cells will be pre-incubated for 0.5 hr with PBS or a soluble ACE2 variant polypeptide agent as described herein (e.g., one or more of hACE2(1-618), hACE2(1-618)-ABD, hACE2(1-618)-Fc) or with one or both of a positive (e.g., hACE2(1-740)) and negative (e.g., mACE2(1-740)) control. In many embodiments, each agent (and optionally each control) is tested in triplicate wells, and at multiple concentrations (e.g., at 0.5, 1, 2, 4, 8, 16, 32, 64 and 128 ug/mL). Subsequently, cells will be infected for 1 h with $1.4\times10^3$ TCID50 (50% tissue-culture infectious dose) of the virus, or left uninfected, and washed in culture medium. 72-96 h post-infection, fluorescence will be measured (viral entry of pseudo-typed V) or 15-20 hpi viral mRNA measured by RT-qPCR (replication of SARS-CoV-2). In some studies performed with live virus (e.g., with live SARS-CoV-2, the inoculum after infection will not be removed, and mRNA measured 15-20 hpi to assess the effect of provided agents on viral progeny.

Cytotoxicity Studies. In some embodiments, characterization of active, soluble ACE2 variant polypeptide agents as described herein may involve one or more cytotoxicity studies. For example, in some embodiments, to assess whether a provided active, soluble ACE2 variant polypeptide agent is toxic to cells, $10^4$ Vero E6 and HEK-hACE2 cells per well will be seeded in a 96-well plate. 24 h post-seeding, different concentrations (e.g., 1-200 ug/ml) of agent to be assessed will be added in triplicate and incubated for 15 h; cytotoxicity will be determined using the CellTiter-Glo Luminescent cell viability assay.

Impact on Receptor Downregulation. In some embodiments, characterization of active, soluble ACE2 variant polypeptide agents as described herein may involve assessment of impact on internalization of membrane-associated ACE2 in the presence of virus, or relevant component(s) thereof (e.g., viral spike protein).

Without wishing to be bound by any particular theory, it is proposed that binding of SARS-CoV-2 spike protein to its membrane-associated ACE2 receptor leads to downregulation of the receptor, possibly as a result of internalization and intracellular processing. Reviewed in [60]. Assays in which such down-regulation are detectable can be used to assess ability of provided soluble ACE2 variant polypeptide agents to disrupt such downregulation. In some embodiments, downregulation is assessed through measurement of ACE2 enzymatic activity and/or protein abundance levels, for example in total cell lysates, isolated membranes, and/or a cytosolic preparation. See [61].

It is relevant to note that some reports have described increased ACE2 upon exposure to α and γ interferons in human airway epithelial cells [52, 62]. If in fact ACE is not downregulated by SARS-CoV-2 infection, then of course provided agents need not be assessed for such activity. However, we observe that the reported ACE2 activation, is only at the mRNA level; moreover, what is upregulated is a variant of ACE2 that is neither enzymatically active nor capable of binding the SARS-CoV2 receptor binding domain [63]. One approach to assessing whether downregulation (or upregulation) of ACE2 is associated with SARS-CoV-2 infection would be to use a specific ACE2 antibody to stain human lungs and kidneys from COVID-19 patients and determine expression level of membrane-associated ACE2. If the anticipated downregulation of ACE2 takes place one, then it may be desirable to characterize provided soluble ACE2 variant polypeptide agents for ability to block or interfere with such downregulation. Provided agents can be characterized for such activity, for example, by contacting permissive cells with virus (or pseudovirus or spike protein) in the presence and absence of a relevant agent, for example over multiple concentrations (e.g., 0.5-128 µg/ml serial dilutions) to examine whether the internalization of the SPIKE/ACE2 complex can be prevented.

For example, in some embodiments, impact on plasma membrane associated ACE2 (which is typically FLACE2) can be evaluated both enzymatically (using Mca-APK-Dnp substrate) and by western blot. Using a Cell Fractionation Kit (Invent Biotechnologies) most of ACE2 activity (~90%) was found in the plasma membrane fraction compared to 10% in cytosolic fraction both in Vero E6 cells and HEK-hACE2 cells. Fractions will be tested in WB and ACE2 activity assays as it is plausible that after internalization of membrane-associated ACE2, the protein might be degraded to smaller fragments devoid of enzymatic activity. Fractions normalized for equal amounts of total protein (100 µg) will be incubated in a tube with Ang II ($10^{-8}$M) with and without a specific ACE2 inhibitor (MLN-4760 $10^{-6}$M). The degraded Ang II will be measured over time (0-4 hrs) by ELISA [25]. In addition, Vero E6 will be grown on slides and incubated for immunofluorescence and confocal microscopy to confirm the internalization of plasma membrane-associated ACE2 induced by the spike and its prevention by a provided soluble ACE2 variant polypeptide agent. Membrane-associated (which is expected to be FL-ACE2) will be differentiated from the soluble ACE2s using Abs to a C-terminal part of ACE2. To verify that the changes are associated with Spike entry, pull-down assay using S1 antibody will be performed.

Studies in Human Organoids. As described herein, human kidney organoids provide a useful model system for studying SARS-CoV-2 infection. We have demonstrated that both hACE2(1-618) and hACE2(1-618) markedly reduced viral replication in the organoids, to about the same extent as did hACE2(1-740) under conditions where mACE291-740) did not. See Example 1 and FIG. 4. Thus, human kidney organoids studies are useful for characterization of soluble ACE2 variant polypeptide agents as described herein.

In some embodiments, such assessments may be performed as described in Example 1. Alternatively or additionally, in some embodiments, useful assessments may be performed at lower concentration(s) and/or at multiple concentrations. For example, in some embodiments, kidney organoids may be infected $10^3$-$10^6$ infectious viral particles, in the presence vs absence of a soluble ACE2 variant polypeptide agent as described herein (e.g., for approximately 1 hour), which agent may be provided at one or more concentrations, for example within a range of about 1 to about 200 µg protein/ml). Three days post infection, levels of viral RNA will be assessed by qRT-PCR to assess the level of SARS-CoV2 infections in the kidney organoids.

Alternatively or additionally, in some embodiments, one or more soluble ACE2 variant polypeptide agents as described herein may be assessed for impact on SARS-CoV2 replication kinetics, tropism, and/or host response [69] using a human organoid system (e.g., human kidney organoids). Additionally, in some embodiments, after organoids are infected with SARS-CoV2, immunofluorescence and electron scanning microscope analyses may be used to study cytopathic effects of viral particles on different cell types. Alternatively or additionally, organoids may also be used as otherwise described herein (e.g., to examine cytotoxicity by exposing them to different doses (1-200 µg/ml) of soluble ACE2 variant polypeptide agent for 2 days at 37° C. with 5% $CO_2$. Media will be removed and any toxicity to organoids will be assessed by Viability/Cytotoxicity assays.

Studies in Mice. A transgenic mouse engineered to express full length human ACE2 under control of the K18 promoter (which confers efficient transgene expression in airway epithelial cells, as well as in epithelia of other organs, including liver, kidney, and gastrointestinal tract (72, 74)) has been developed and is available from Jackson Laboratories. Thanks to this expression of the full length human ACE2 in their airway epithelial cells, these mice are susceptible to infection by SARS-CoV-2 when intranasally exposed (e.g., to aerosolized virus), and display severe morbidity and high mortality within about 6-7 days of exposure. [74, 75].

Figure 15:
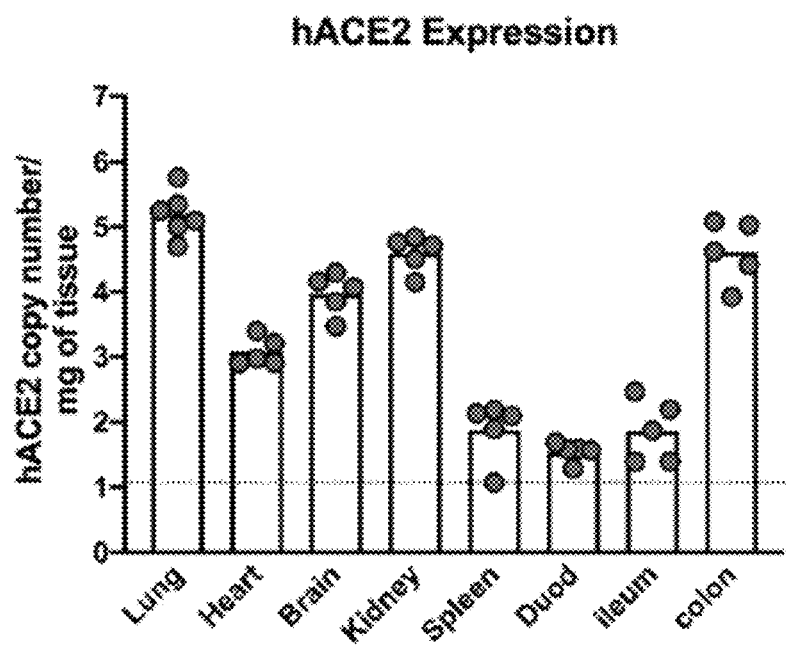
FIG. 15. Panel A. mRNA expression levels of hACE2 in the lung, kidney, heart, brain, spleen, duodenum, colon, and ileum of naïve K18 hACE2 mice (73). Panel B. Enzyme activity of hACE2 in organs from K18 TG (n=2) that has human ACE2 versus WT (n=2) mice based on our S1 RBD-ACE2 binding assay.
Figure 15:
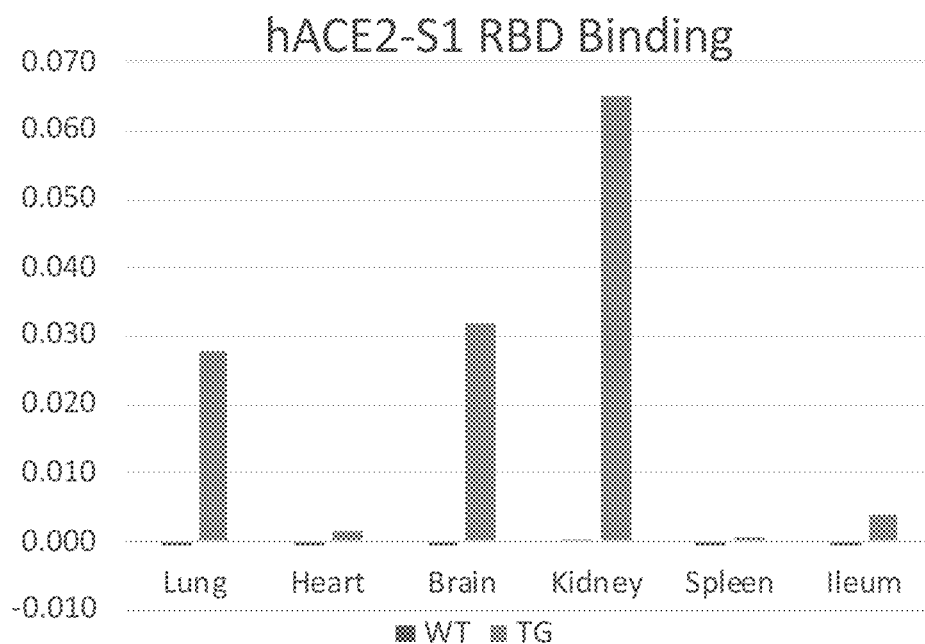

Expression of the human ACE2 in these mice (referred to herein as K18-hACE2 mice) can be detected through mRNA analysis or immunostaining studies, etc. Alternatively or additionally, enzyme activity can be determined. In some embodiments, active human ACE2 can be distinguished from mouse ACE2 in transgenic mouse tissues based on its ability to bind SARS-CoV2 51 RBD. For example, we have developed an assay in which a His-tagged spike protein RBD is immobilized on a solid support (e.g., Nickel-coated microplates. When tissue from transgenic K18-hACE2 mice are contacted with the support, binding is detected; no such binding is observed with tissue from wild type mice, which do not express hACE2 but instead express only mACE2, which does not bind to SARS-CoV-2 spike protein (see FIG. 15). This assay has been validated using negative controls (mouse rACE2, non-coated wells) and human rACE2 standard for dose-response curves. The organ distribution of binding that we found using our assay generally corresponds to that reported by mRNA [74]; that is, expression is clearly seen in lungs, brain and kidneys (FIG. 15).

This approach can also be used to quantify level of binding of SARS-CoV-2 spike to hACE2 in each organ of K18-hACE2 mice, and/or to determine whether detectable hACE2 that is present and/or that is bound to spike protein, is associated with the plasma membrane.

Figure 16:
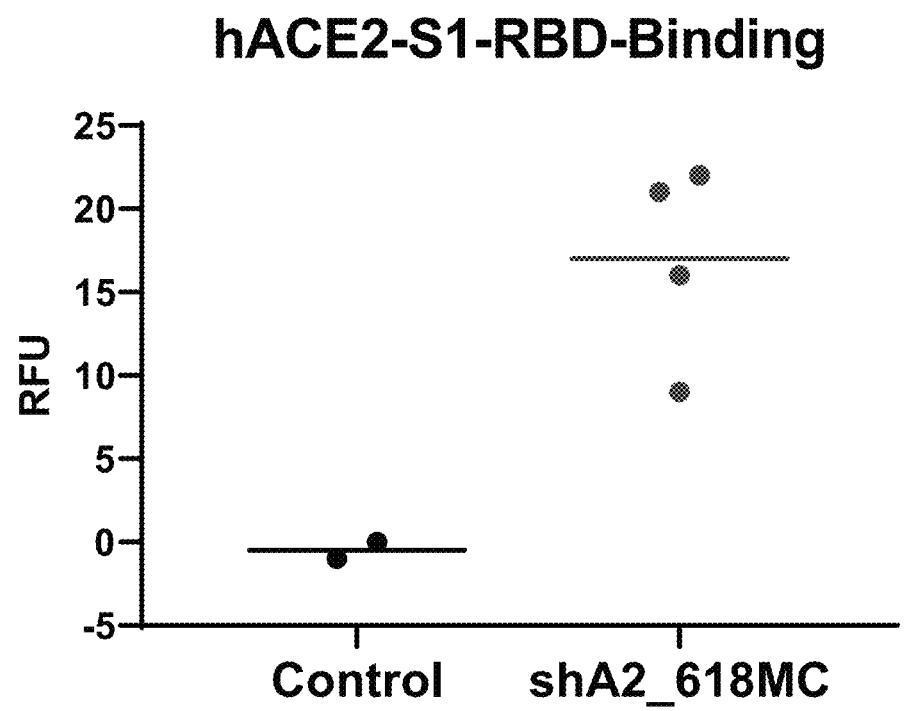
FIG. 16. Binding of human soluble ACE2(1-618) to S1 RBD protein is detected in WT mice 3-4 d after i.v. hydrodynamic injection of hACE2(1-618) mini-circle DNA but not in control WT mice.

Furthermore, we have used this same assay to establish that soluble human ACE2(1-618) can be expressed, detected, and bound by the S protein of SARS-CoV-2 in mice. Specifically, using plasma obtained from mice in which high levels of soluble human ACE2(1-618) are expressed by minicircle delivery, we have shown that there is a marked increase in binding of the SARS-CoV-2 RBD. See FIG. 16. These data confirm, as described herein, that hACE2(1-618) binds to SARS-CoV-2 in vivo and thus can exert a decoy effect.

Mice expressing human ACE2 protein (e.g., full length ACE2), and/or protein variants (e.g., hACE2(1-740) or a variant agent described herein such as hACE2(1-618) or hACE2(1-618)-ABD), are useful, among other things, for assessment and/or analysis of soluble ACE2 variant polypeptide agents as provided herein.

For example, mice (e.g., F18-hACE2 mice) that express full-length human ACE2 are susceptible to infection with SARS-CoV-2, and various aspects of such infection can therefore be studied in such mice, as can any impact thereon of provided soluble ACE2 variant polypeptide agents. For example, extent, type, and/or timing of injury to tissues such as lung and/or kidney can be assessed in such mice. Alternatively or additionally, impact of SARS-CoV-2 infection on level, localization, and/or activity of hACE2 (e.g., full-length hACE2) in tissues of such mice, can be assessed. In some embodiments, provided soluble ACE2 variant polypeptide agents may be characterized by their impact on one or more features of SARS-CoV-2 infection and/or of level, localization and/or activity of hACE2 in a mouse, such as a K18-hACE2 mouse.

For example, in some embodiments, relevant mice are inoculated intranasally with SARS-CoV-2 in PBS (or in PBS alone for the untreated control group; n=10 for each). Animals are monitored for as long as possible, typically less than 2 weeks. Impact of administration of a soluble hACE2 variant polypeptide agent as described herein will be assessed. In some embodiments, such agent may be delivered as a polypeptide (e.g., that is injected or administered as an aerosol); in some embodiments, such agent may be delivered, for example, by DNA minicircle delivery and/or by AAV delivery.

In some embodiments, intranasal inoculation involves administration of a large dose (e.g., $2 \times 10^5$ PFU), so that rapid development of significant morbidity and mortality can be expected and beneficial impact of administering soluble hACE2 variant polypeptide as described herein can readily be assessed. Those skilled in the art will appreciate that this approach may be considered particularly relevant to situations of acute exposure, or expected high risk thereof. Thus, provided agents effective in this context may be particularly useful clinically, for example, in medical personnel at risk, patients and personnel in nursing homes, military personnel, etc, and/or particularly in prophylactic settings. Furthermore, provided agents demonstrated to be effective in such a study when administered intranasally may be particularly appropriate for aerosol delivery, including in self-administration contexts.

In some embodiments, lower doses of virus are administered so that different features and/or stages and/or infection contexts are assessed. Alternatively or additionally, in some embodiments, timing of administration, relative to timing of exposure to virus, may be modified. For example, in some embodiments, agent is administered prior to virus (modeling prophylactic contexts); in some embodiments, agent is administered after virus, and/or after development of detectable morbidity (modeling therapeutic contexts).

In some embodiments, provided soluble hACE2 variant polypeptide agents are characterized in that, when delivered at high levels (e.g., as achieved by minicircle delivery), will show protective effect, e.g., as may be reflected, for example, in improvement in mortality and/or a stable weight in infected K18-hACE2 mice.

It is worth noting that, in some embodiments, useful soluble hACE2 variant polypeptide agents provided herein are characterized in that, when expressed in high levels (e.g., as achieved by minicircle delivery) in mice, they do not confer infectivity to mice not expressing full-length hACE2 (and not otherwise susceptible to infection).

Independent of any characteristic that may be assessed by systemic administration (or administration by any route other than pulmonary), in some embodiments, useful soluble hACE2 variant polypeptide agents provided herein are characterized by an ability to block SARS-CoV-2 infectivity when administered via a pulmonary route (e.g., intranasally, such as by aerosol, etc); in some embodiments, such agents are characterized in that they reduce infectivity when administered prior to exposure, and/or prior to development of symptopms (i.e., in prophylactic contexts); in some embodiments, such agents are characterized in that they reduce infectivity and/or delay onset of, reduce probability of, and/or reduce extent or degree of development of one or more symptoms or features of established infection (e.g., of COVID-19 disease).

Elucidation of Mechanisms. Without wishing to be bound by any particular theory, we note that comparison of mouse and human soluble ACE2 polypeptide variants may be useful to examine the mechanisms of action of provided agents. As noted herein, we propose that decoy action may be particularly useful in preventative contexts; whereas restoration of activity may be particularly useful in established infection; dosing (e.g., timing and/or amount of each dose), identity of agent, and/or combination therapy may differ for these different patient populations.

Figure 17:
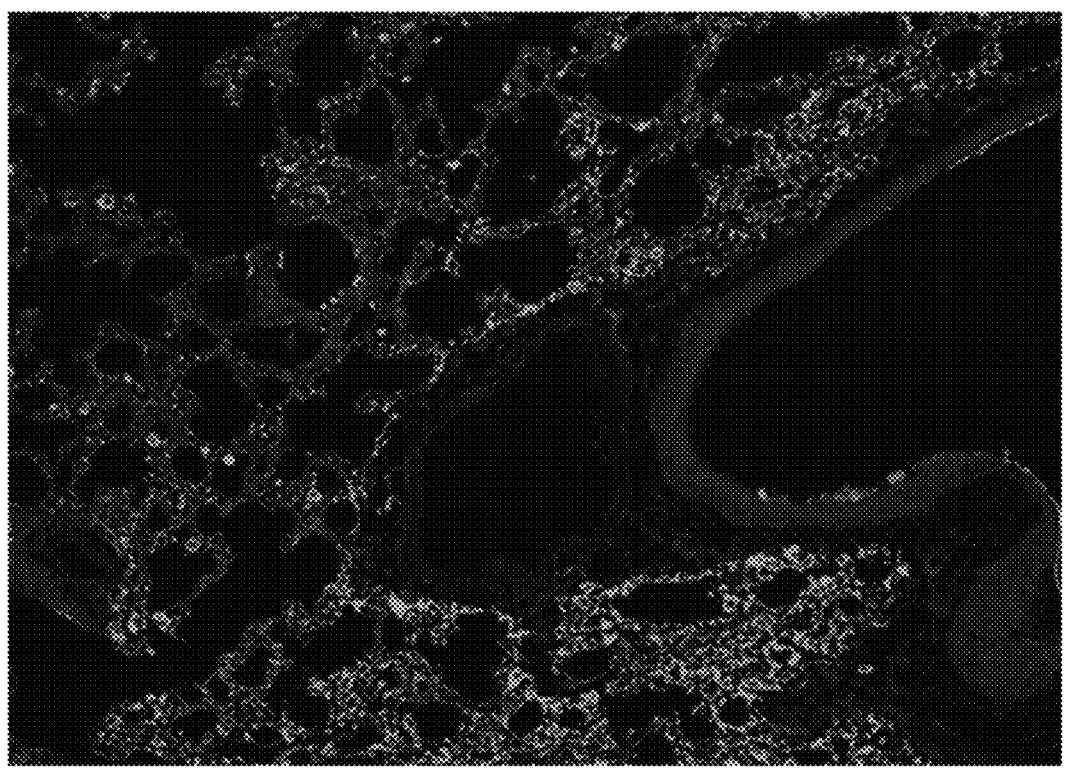
FIG. 17. Immunoreactivity of ACE2 within the alveolar wall (interstitium) in lung tissue from an ACE2KO mouse 24 after intranasal 618ABD instillation (1 mg/Kg BW).

As confirmed herein, fusion of either a mouse (e.g., mACE2(1-619)) or human (e.g., hACE2(1-618)) truncation variant of soluble ACE2 can extent duration of action of the truncation variant; such extension can be to at least about 3-4 days and can be assessed, for example by measuring circulating ACE2 levels over time. Moreover, we have demonstrated that the fusion variant hACE2(1-618)-ABD can be effectively administered intranasally, as documented by detection of alveolar immunostaining in an ACE2 knockout mouse within 24 hours after administration. See FIG. 17. In some embodiments, a provided soluble ACE2 variant polypeptide agent is characterized by effective alveolar delivery upon intranasal administration; in some embodiments, degree of such delivery may be assessed relative to another agent (e.g., to an appropriate reference such as an appropriate positive or negative control, or both; in some particular embodiments, hACE1(1-740) is an appropriate positive control.

Elucidation of mechanism of action (and thus characterization of agents whose mechanism of action is elucidated) may, in some embodiments, involve studies in transgenic mice. For example, in some embodiments, provided agents may be assessed for ability to reduce infectivity and/or to protect from damage (e.g., to lung and/or to kidney). In some embodiments, provided "extended duration of action" variants (e.g., fused with Fc or, in some embodiments, ABD). Indeed, among other things, the present disclosure identifies the source of a problem with strategies that may utilize a soluble ACE2 protein variant that does not have an extended duration, including, for example, that more frequent dosing may be required, which may be expensive or inconvenient or, moreover, may be difficult to achieve. By contrast, a variant characterized by extended duration of action may have surprising advantages including, for example, reducing risk of "viral escape" by reducing the interval when soluble ACE2 protein level and/or activity may be sufficiently low that the virus can "escape" from binding such soluble protein and, for example, bind to the full length receptor instead. We observe that the non-truncated soluble hACE2 (1-740) that is currently in clinical trials (NCT00886353) has a half-life of only a few hours and is given twice a day intravenously. The present disclosure teaches that variant agents with longer duration of action than hACE2(1-740) are preferable, among other things because, in certain embodiments, they may be amenable to less frequent updates. Moreover, the present disclosure teaches that variant agents that have a smaller molecular size than hACE2 (1-740), preferably small enough to be amenable to glomerular filtration, such that they may provide additional benefit to the kidneys and/or may be particularly appropriate and/or beneficial for administration to subjects suffering from or susceptible to kidney damage (e.g., AKI).

In a representative assessment, a provided agent (or plurality of agents, whose performance, in some embodiments, may be assessed relative to one another and/or relative to one or more appropriate control(s)) may be administered either before (e.g., 2 hours before) or after (e.g., about 24 hours after) intranasal viral inoculation. In some embodiments, at least one further dose may be administered, for example within or approximately at 3 days post-innoculation). In some embodiments, a dose may have been selected, for example, via a prior study in which various alternative doses (e.g., each of which is a multiple of a prior dose, such as 2 fold, 3 fold, 4 fold, 5 fold, 6 fold, 7 fold, 8 fold, 9 fold, 10 fold, etc; in some embodiments, for example 0.2, 2.0, and 20.0 ug/g body weight). In some embodiments, performance achieved by a particular variant may be assessed relative to an appropriate reference (e.g., a positive or negative control). In some embodiments, mortality and/or weight will be assessed.

Alternatively or additionally, in some embodiments a comprehensive evaluation may be performed. For example, in some embodiments, at euthanasia, organs will be collected, and viral mRNA measured by RT-qPCR. mRNA levels of SARS-CoV-2 and proinflammatory chemokines IL-6, IFNy, IFNα2, CXCL9, CXCL10, CCL2, and CCL7 can be evaluated. In some embodiments, lung and/or kidney histology from formalin blocks (where the virus is deactivated) may be used. In some embodiments, profiles for angiotensins and/or bradykinins peptides will be evaluated in plasma, lung and kidney homogenates extracted on phenyl silica columns; these peptides can be measured by LC/MS-MS, for example using a fingerprint panel [25] [78]. For these measurements, a protease inhibitor cocktail will typically be used for plasma, while lungs and kidneys will be snap frozen and sent for processing and LC/MS-MS measurement on dry ice. In some of the kidney studies, tubular and glomerular preparations will be separated using magnetic beads, as we have done to assess FL-hACE2 distribution within kidney in k18-FL-hACE2 mice [27]. Kidney function will be evaluated by measurements of BUN and creatinine. Urine protein and markers of proximal tubular injury such as KIM-1 and NGAL will be measured as well.

To examine the contribution of the two proposed mechanisms of potential therapeutic benefit (decoy effect vs increased ACE2 enzymatic activity or both) we will use two approaches. One is based on administering soluble protein devoid of enzymatic activity (mutated hrACE2 protein) and the other is based on mouse soluble ACE2 protein that has enzymatic activity but lacks the human receptor binding site for SARS-CoV-2. First, to address the decoy effect mechanism, we will generate a soluble hACE2(1-618)-ABD mutant that lacks ACE2 enzymatic activity. For this, a site-directed mutagenesis will be performed on hACE2-618 cDNA to generate a catalytically inactive (H374N, H378N) mutant hACE2 (1-618)-ABD. This enzymatically inactive protein (confirmed by lack of enzyme ACE2 activity despite the presence of protein documented by ELISA&WB) will be given to the k18-hACE2 mice. It should be able to intercept the virus but being enzymatically inactive may not provide the same degree of protection. In some embodiments, this will be assessed by mortality, weight loss and organ pathology as compared to the active protein. Second, to assess the importance of simply amplifying ACE2 enzymatic activity we will use a mouse counterpart of ACE2(1-618)-ABD; such a mouse variant (mACE2(1-619)-ABD) has intact ACE2 activity and moreover is filterable by the kidney.

Without wishing to be bound by any particular theory, we propose that human soluble hACE2(1-618)-ABD will markedly reduce mortality, weight loss and improve organ function (Table 2). The mutant human soluble ACE2 is anticipated to have some protective action from its decoy effect, but not as much as the human soluble 1-618-ACE2-ABD because it lacks (Table 2). The mouse soluble ACE2 is also expected to have some protective effect owing to its enzymatic activity, but also less than the human soluble 1-618-ACE2-ABD (table 2). When given only after the viral inoculation we expect improvement as well but possibly to a lesser degree as assessed by mortality and organ damage. The latter will be assessed by lung and kidney histopathology. The viral load in the lungs and the levels of proinflammatory cytokines should be decreased as well. In acute lung injury associated with SARS-CoV2 infection the levels of ACE2 are likely to be decreased with the attendant increase in peptides such as Angiotensin II and des Arg9 Bradykinin that are metabolized by this enzyme. Therefore, normalization of the levels of these peptides is expected.

TABLE 2

|  | Reduced mortality | Retarded weight loss | Organ improvement |
|---|---|---|---|
| Human soluble ACE2(1-618)-ABD | ++++ | ++++ | ++++ |
| Mutant human soluble ACE2 (1-618)-ABD | ++ | ++ | ++ |
| Mouse soluble ACE2 (1-619)-ABD | ++ | ++ | ++ |

Without wishing to be bound by any particular theory, we propose that a smaller variant agent, and particularly an agent that is sufficiently small to be amenable to glomerular filtration, may be particularly useful as described herein. For example, we propose that hACE2(1-618)-ABD may reasonably be expected to provide better protection of kidney histology and function than, for example, hACE2(1-618)-Fc due to its smaller size. In terms of angiotensin profile, we expect, it has a shorter Angiotensin profile. Specifically, increased formation of Angiotensin 1-7 and less accumulation of Angiotensin II. See [24]. Downstream of these peptides there should be more formation of Angiotensin 1-5. In the plasma and lungs there should also be increased formation of Angiotensin 1-7 from Angiotensin II. The levels of Angiotensin II in plasma, if elevated, fall with ACE2 administration, whereas they do not change when the levels are low, which is the normal physiological state. Thus, we propose that provision of ACE2 enzymatic activity alone should be beneficial to treatment of SARS-CoV-2 infection. If levels of ACE2 in the lungs and kidney, then buildup of Angiotensin II and/or des-Arg9 Bradykinin can foster lung injury. The mouse mACE2(1-619)-ABD may be only partially protective; we anticipate that infusing mouse mACE2 (1-619)-ABD alone will not be as protective as human ACE2 proteins (e.g., hACE2(1-618)-ABD) that confer both the decoy effect and enzymatic activity (Table 2). This interpretation will be further supported if the mutant human protein, that lacks the binding site for SARS-CoV2 receptor binding domain, provides total or partial therapeutic benefit. We anticipate some improvement in mortality and kidney and lung injury from the mouse mACE2(1-619)-ABD but definitely less than that provided by the human proteins that, in addition to providing enzymatic activity, provide the decoy effect. These considerations are not only relevant to the understanding of the mechanism but have a practical implication. The decoy effect may not be as critical once the cells are infected by SARS-CoV2 and yet soluble ACE2 proteins may be very valuable in the treatment of SARS-CoV2 infection and its complications because of the enzymatic activity associated with their administration.

Without wishing to be bound by any particular theory, we propose that there will be a role of organ protection independent of any decoy effect. In this regard, the present disclosure teaches that kidney protection is more likely with a short ACE2 variant fused with a small tag (ABD) that is more likely to be filterable by the kidney. Radio imaging studies can examine kidney uptake of shorter human variants. Therefore, we anticipate better kidney outcomes with the short hACE2(1-618)-ABD than the larger hACE2(1-740) or hACE2(1-618)-Fc. The shorter variant moreover is expected to reduce Ang II and increase ANG 1-7 within the kidney as compared to the larger proteins that essentially have only systemic effects but do not reach the kidney because it cannot be filtered [24]. Augmentation of ACE2 activity within the kidney is expected to prevent Ang II accumulation while fostering Ang 1-7 formation as a main mechanism of kidney protection. We anticipate therefore, that human ACE2(1-618-ABD) will be a particularly good candidate to prevent/attenuate AKI associated with SARS-CoV2 infection.

Assessment in Distinct Populations. The present disclosure appreciates that various aspects of SARS-CoV-2 infection and/or of roles of provided soluble hACE2 variant polypeptide agents as discussed herein can more easily be examined using Adeno associated viral (AAV) vectors and/or minicircle DNA delivery of human full length ACE2 (FL-ACE2) than with transgenic lines such as k18-hACE2. With these models of induced permissiveness for SARS-CoV2 infectivity we will be able to study conditions that in humans are known to increase the severity and outcome of COVID19 [80-84]. This approach will not require crossing of the k18-hACE2 mice with the mouse disease models; moreover, we can direct the expression of FL-ACE2 in a more organ specific manner, particularly with AAV. AAV vectors have a transgene cargo capacity of 4.4 kb and can be packaged with numerous serotypes that exhibit different patterns of biodistribution [85-87].

Figure 13:
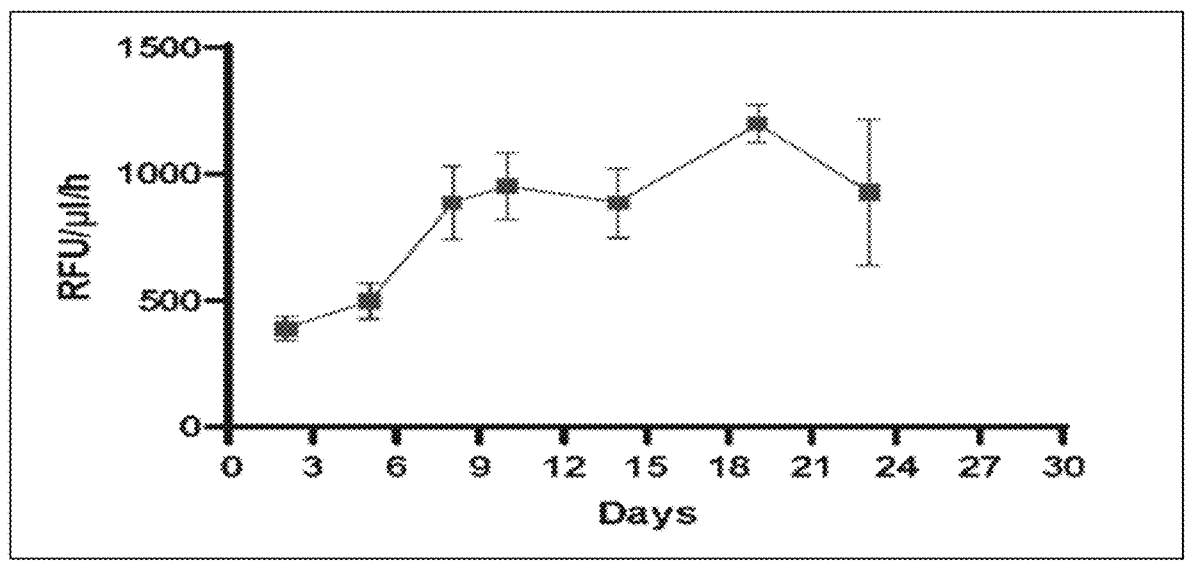
FIG. 13. Human rACE2(1-618) given IP every 3 days results in a sustained high level of ACE2 activity over time.
Figure 14:
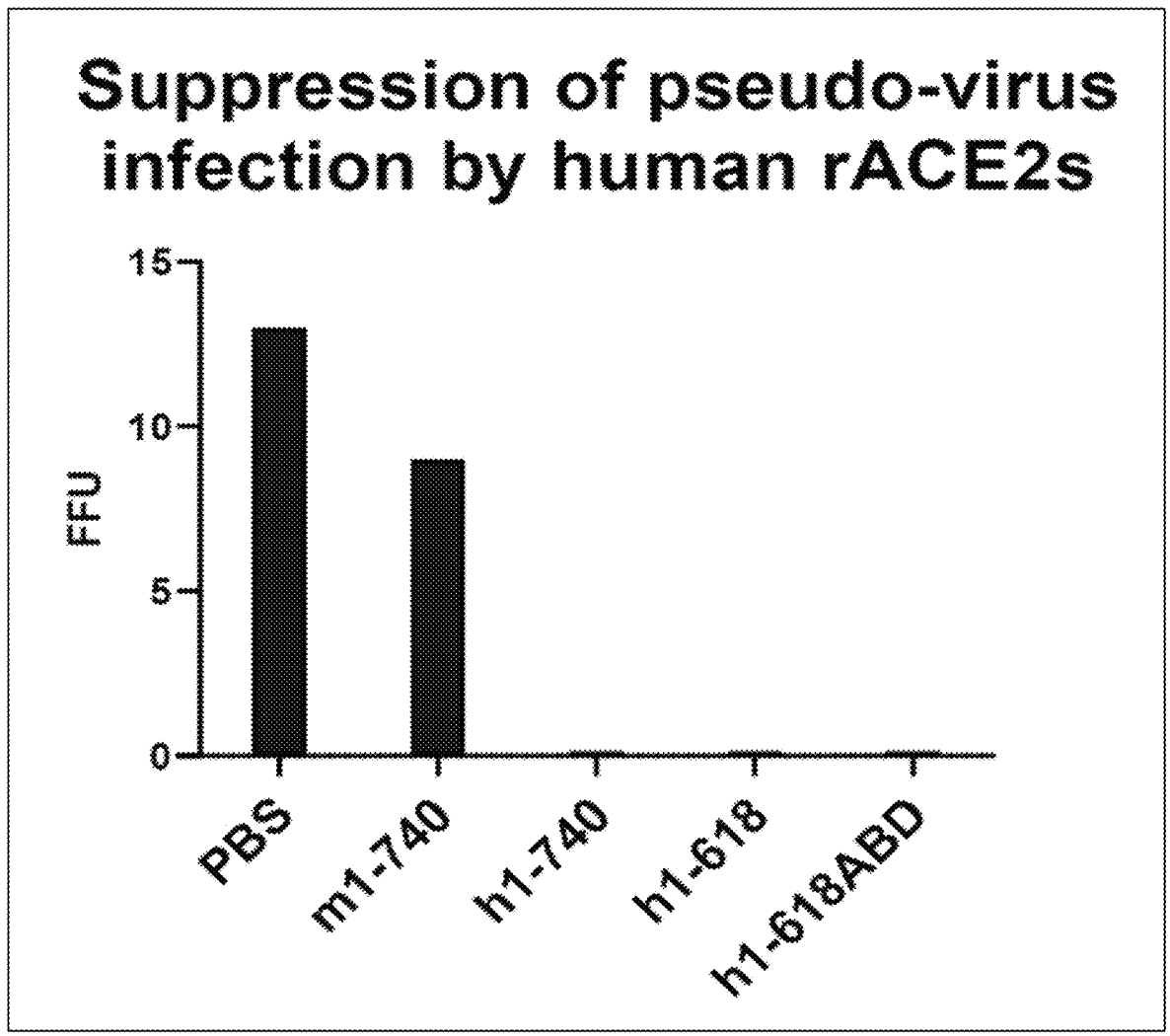
FIG. 14. Non-truncated soluble hACE2(1-740), used as positive control), and short ACE2 proteins (hACE2(1-618) & hACE2(1-618)-ABD) completely inhibited pseudo typed viral entry into HEK-hACE2 cells. In contrast, non-truncated soluble mouse mACE2(1-740), did not suppress pseudo virus infection efficiently and yielded results similar to that of PBS effect. All proteins were used at a concentration 200 ug/ml. FFU: focus forming units.

With intranasal delivery of AAV as described herein we expect to create a model of sustained human FL-ACE2 expression restricted mainly to the upper respiratory tract and alveolar cells. With the AAV approach by retrograde renal vein injection we can direct the FL-hACE2 (packaged in AAV9) to the kidney glomeruli (92) while retrograde ureteral approach directs the AAV9 mainly to kidney tubules [90]. Dose-dependent studies can be performed in either or both, for example to determine the minimum amount of FL-ACE2 that is necessary to confer SARS-CoV-2 infectivity. One advantage of the minicircle DNA approach is that we can create the permissive model rapidly since we can inject easily 10-20 mice a day. This inducible model, moreover, is functional as early as 3 days after the injection [57]. Minicircle DNA delivery of FL-ACE2 in ACE2 KO achieves ACE2 activity in several organs, notably in the liver, ileum and in the lungs. After minicircle DNA delivery of human FL-ACE2 (1 ug/g BW) staining for ACE2 was documented in bronchioles and pulmonary vessels with faint staining in alveoli (FIG. 13). Of note, endogenous TMPRSS2 is present and colocalizes with ACE2 (FIG. 13). The mouse lungs have TMPRSS2, which is required for SARS-CoV-2 infection, in bronchioles and type II pneumocytes [52].

Figure 18:
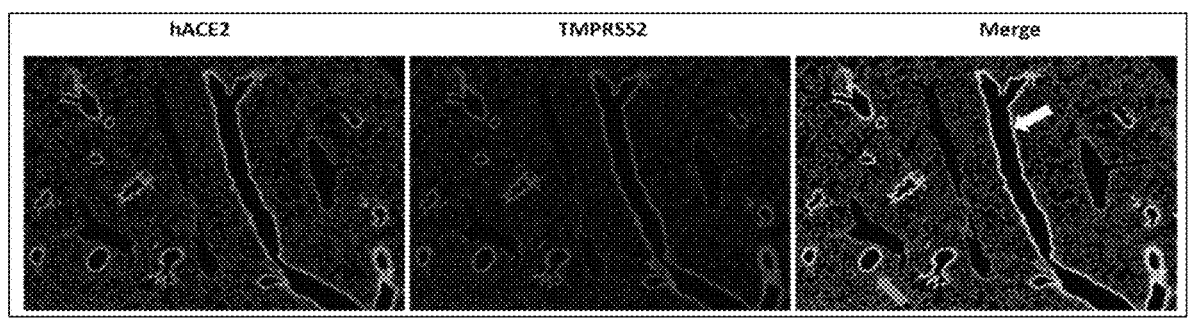
FIG. 18. Immunofluorescence and confocal imaging of lung tissue from ACE2 KO mouse infused with FL-ACE2 by minicircle DNA delivery. FL-ACE2 and TMPRSS2 co-localize in bronchioles (arrow), vessels (arrow) whereas in the background alveolar capillaries show faint staining (dose of 1 ug/g MC DNA BW)
Figure 19:
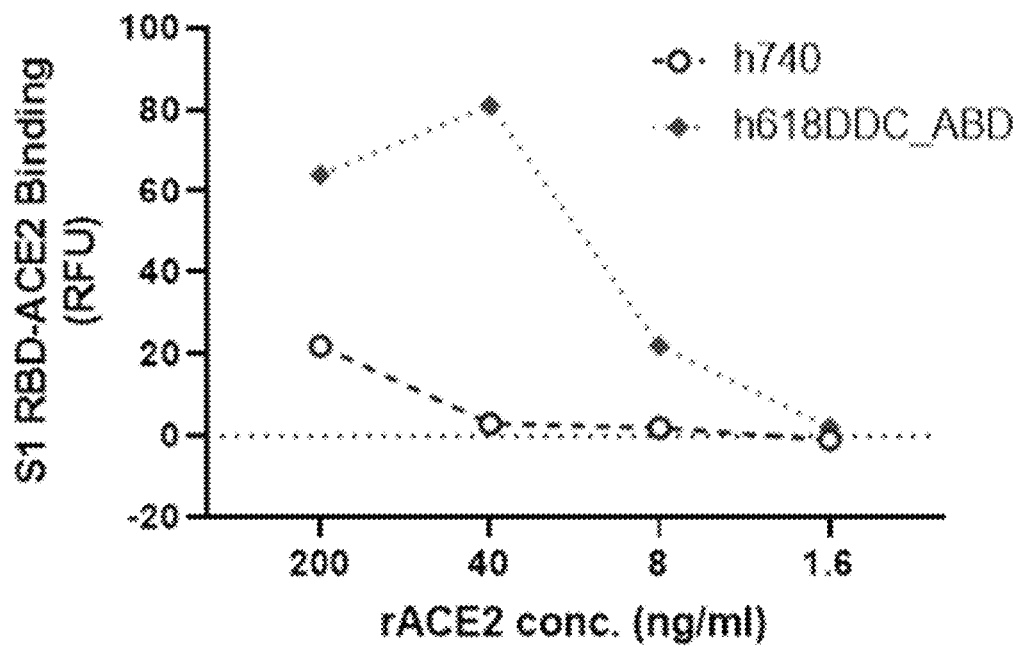
FIG. 19. Soluble human recombinant ACE2 1-740 (h740) and human recombinant variant ACE2 1-618 fused with modified hinge region (DDC) and ABDcon (h618DDC_ABD) were both tested at different concentrations in a binding assay using immobilized SARS-Cov-2 S1 receptor binding domain (RBD). The h618DDC_ABD variant showed much higher affinity than h740 to bind viral S1 RBD protein. DCC sequence is KCHWECRGCRLVC (SEQ ID NO:16).
Figure 20:
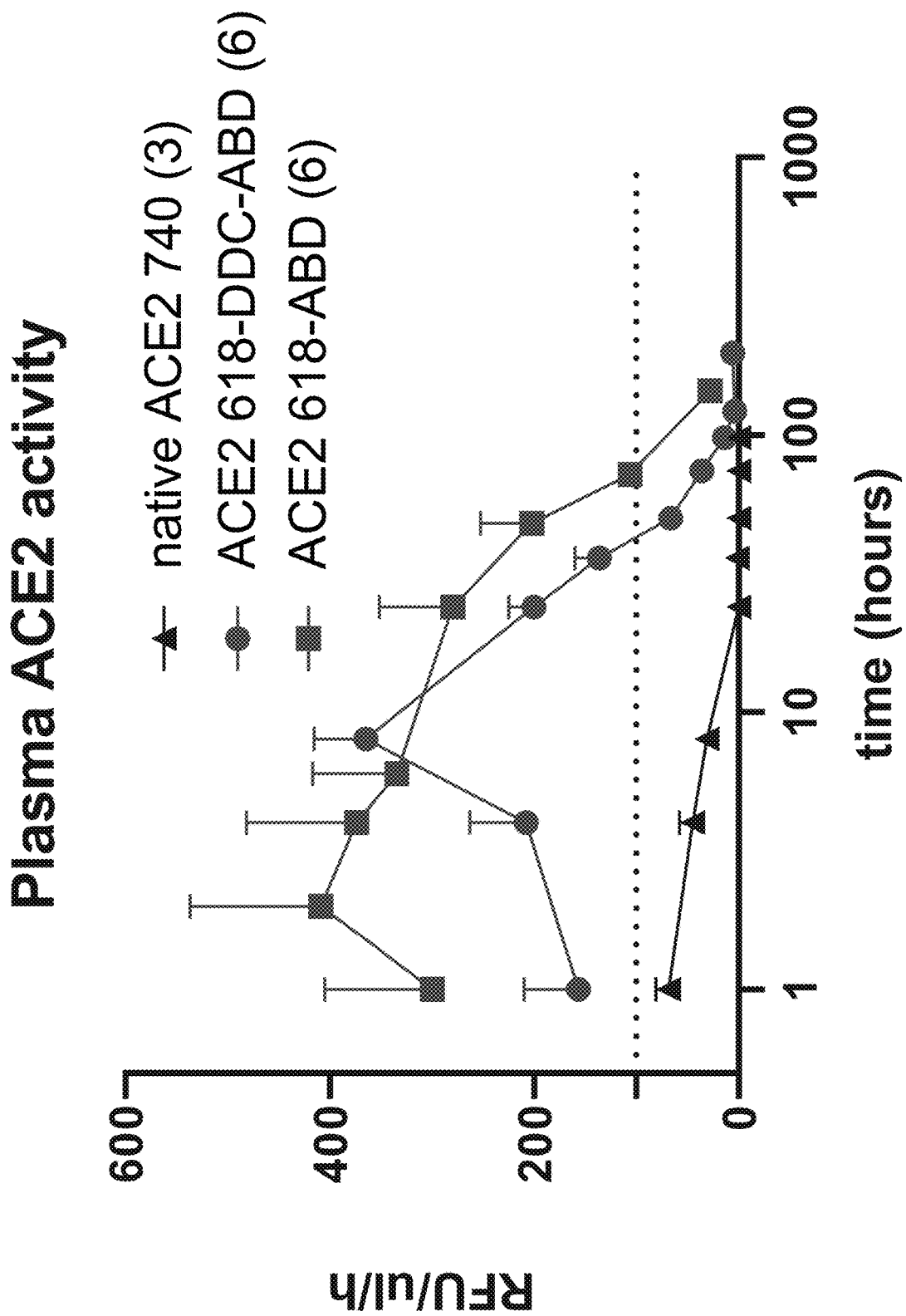
FIG. 20. Pharmacokinetics of novel ACE2 618-DDC-ABD protein as compared to other two soluble ACE2 variants in male C57BL6 mice. Mice received a single intraperitoneal (i.p.) injection of 1 μg/g body weight of ACE2 740, ACE2 618-ABD or ACE2 618-DDC-ABD. After the i.p. injection, blood samples were collected at the indicated time-points and plasma ACE2 activity measured using Mca-APK-Dnp substrate. Both 618-DDC-ABD and 618-ABD ACE2 variants resulted in higher plasma ACE2 activity than native soluble ACE2 740 post injection. Moreover after native ACE2 740 administration, plasma ACE2 activity decreased already after 8 hours post injection whereas the novel ACE2 618-DDC-0ABD and 618-ABD proteins resulted in markedly increased duration of action as shown by plasma ACE2 activity about 100 RFU/ul/hr (dotted line) at 72-96 hours.
Figure 21:
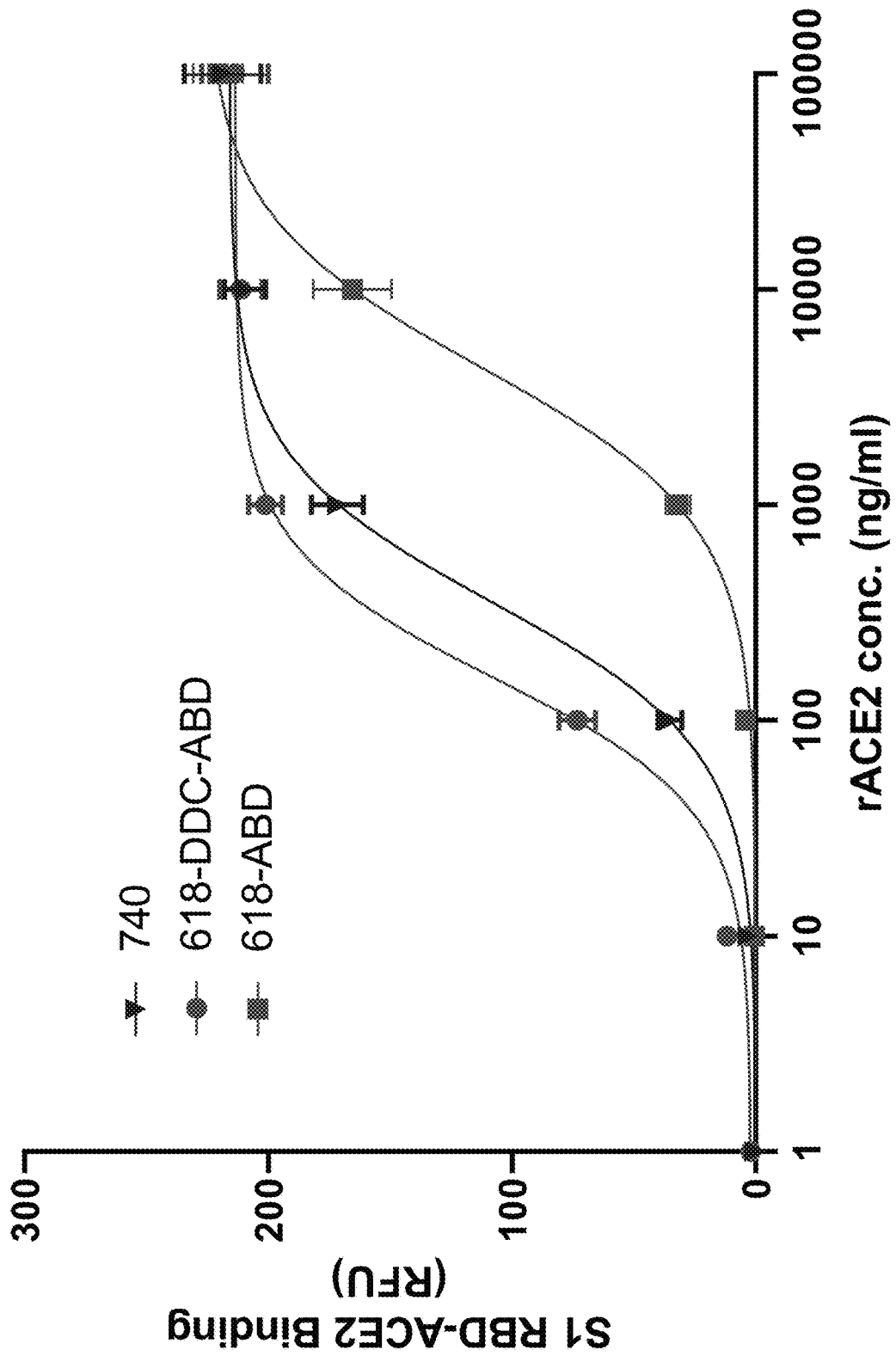
FIG. 21. Enhanced binding affinity to the Receptor Binding Domain (RBD) of the viral S1 Glycoprotein of novel ACE2 618-DDC-ABD as compared to other two soluble ACE2 proteins. The binding of ACE2 variants 618-DDC-ABD, 618-ABD, and the native ACE2 740 protein to SARS-CoV-2 S1-RBD was studied using a recently published assay (https://doi.org/10.1681/ASN.2020101537).

In exemplary studies, to achieve an optimal dose, mice will be given different doses of AAV9 ($10^9$ to $10^{11}$) encoding FL-ACE2 via intranasal injection. The directed approach should ensure a robust incorporation of human FL-ACE2 mainly restricted to lungs and upper respiratory tract. We have used minicircle DNA for soluble mouse ACE2 delivery to produce a high level of ACE2 activity in plasma that was sustained for more than 30 weeks [57]. Of note, the increase in plasma ACE2 activity was dose-dependent. With the minicircle DNA delivery of FL-ACE2 we expect tissue expression and minimal, if any, additional plasma ACE2 activity because this form of ACE2 is membrane bound. Human FL-ACE2 DNA will be injected into tail vein by hydrodynamic injection. Our preliminary data shows that lung anchoring of human FL-ACE2 delivered by a dose of 1 ug/g BW minicircle DNA can be achieved successfully (FIG. 18). Some mice will be sacrificed at 3-7 days after AAV or minicircle DNA injection and organs will be collected for ACE2 activity, immunostaining and mRNA expression of human FL-ACE2 in various organs. To confirm that the increase in ACE2 activity is attributable to expression of human FL-ACE2 and not ACE2 activity from endogenous mouse FL-ACE2 we will use our S1 RBD-ACE2 binding assay.

Both forms of FL-ACE2 delivery should work to induce permissiveness for infection. We plan to compare each modality to the other in terms of the "phenotype" achieved upon SARS-CoV2 infection in normal mice and then prioritize the modality of delivery for specific mouse disease models. By "phenotype" we mean level of organ expression, organ damage and mortality, which may vary in the 2 modes of FL-ACE2 delivery.

Studies will be done both in male and female of different age (8-12 weeks vs 40-60 weeks of age) to examine possible sex differences in the course and severity of the illness caused by SARS-CoV-2.

To study obesity the ob/ob mouse will be used [91, 92]. BTBR ob/ob will be used to mirror human diabetic kidney disease, the BTBR ob/ob is proteinuric but not hypertensive [91, 93]. As a model of hypertension, we will use the renin transgenic (RenTG) mouse (129S/SvEv-Tg(Alb1-Ren) 2Unc/CofJ) [50, 94]. RenTG mice has high liver production of renin which results in increased angiotensin II [50, 94].

Initial studies will be done with $2 \times 10^5$ PFU SARS-CoV-2 in PBS and PBS alone for the untreated control group (n=10 each) as in the k18-hACE2 studies described above. Because of the expected high mortality, we plan studies with lower viral doses to try to replicate clinical correlates that are not as fulminant. We expect that in the models with diabetes and hypertension, AKI upon SARS-CoV2 infection will develop. If AKI does not develop spontaneously or it is mild in these models after SARS-CoV-2 infection we will induce it with a single injection of lipopolysaccharide (LPS) (5-15 mg/kg) [95]. This causes activation of Toll-like receptor 4 (TLR-4) on host immune cells, with subsequent release of inflammatory cytokines such as IL-1, TNF-α, and IL-6, leading to hemodynamic alterations, widespread inflammation reminiscent of those of sepsis [96]. It is a simple model with some similarities of human sepsis pathophysiology [97].

The potential benefit of soluble ACE2 therapy as described herein will then be examined by intranasal application at a previously-determined (see above) optimal dose. We will prioritize studies with hACE2(1-618)-ABD that has a better potential for kidney delivery and treatment of associated AKI. One advantage of hACE2(1-618)-ABD is that it does not lower blood pressure in normal mice which makes it safer in the setting of AM. Administration of hACE2(1-618)-ABD via nasal route (1 mg/kg BW) to ACE2 KO mice results in a robust level of ACE2 activity in lung lysates (63±7 RFU/ug prot/hr n=3) as measured 24 hours after administration. The presence of ACE2 in the alveolar interstitium moreover was confirmed by IF. Permissive mice induced by either minicircle or AAV will be infected and then treated with hACE2(1-618)-ABD or placebo (n=10 per group).

hACE2(1-618)-ABD will be given according to 2 different protocols to assess pretreatment and posttreatment (after inoculation). In one protocol, the protein will be given 2 hours before viral inoculation intranasally and in another protocol the dose will be given 24 hours post viral inoculation. Animal health, weight and mortality will be monitored daily. ACE2 activity, Ang II and ang 1-7 will be measured using ELISA and/or LC/MS-MS [78]. At euthanasia at day ≥7 or when the mice die as a result of virus-induced illness, the organs will be collected. Assessments will include histological evaluation of the lungs and kidneys, macrophage and lymphocyte infiltration and mRNA levels of SARS-CoV-2, and proinflammatory cytokines: IFN-y, IFNα2, IFNB IL-6, IL-28a/b, CXCL9, CXCL10, CCL2, and CCL7. Blood pressure will be measured as previously described [21]. Kidney injury will be scored after 48-72 hr through a semi-quantitative analysis. Kidney tubular damage defined as tubular epithelial swelling, loss of brush border, vacuolar degeneration, necrotic tubules, cast formation, and desquamation, will be scored from 1 through 4 according to % area of involvement per high power field (400×)[98]. Weight loss and the survival curves will be used as endpoints.

We expect that human FL-ACE2 expression by either AAV or MC delivery will be achieved rapidly (days) and in a sustained manner (months) which will render the mice susceptible to SARS-CoV-2 infection. This will allow to assess the impact of preexisting conditions and assess the expected favorable impact of soluble ACE2 based therapy. In animals infected with lower viral doses it should be possible to discern differences in outcomes (if they exist) between males and females (e.g., worse in males) and older and younger animals (e.g., worse in older). With higher viral doses, it is unlikely that any differences will be found as the infection may be overwhelming. The same can be said about the groups with obesity, diabetes and hypertension and their respective controls. It is precisely in these groups with expected severe outcomes and with higher risk of AKI where demonstrating the rescue effect of technologies provided herein as a way to mimic the clinical setting where severe SARS-CoV-2 infection occurs. We expect improved survival and reduced lung injury, as well as less severe AKI as shown by histology, BUN and creatinine. Animals treated with provided soluble hACE2 variant polypeptide agents, as a result of increased ACE2 enzymatic activity, should have an improved profile of Angiotensin and bradykinin peptides (more Angiotensin 1-7, less Angiotensin II, less des-Arg9 Bradykinin) determined by fingerprinting [25].

REFERENCES

1. Batlle, D., M. J. Soler, M. A. Sparks, S. Hiremath, A. M. South, P. A. Welling, S. Swaminathan, Covid, L. Ace2 in Cardiovascular, and G. Kidney Working, *Acute Kidney Injury in COVID-19: Emerging Evidence of a Distinct Pathophysiology*. J Am Soc Nephrol, 2020.
2. Hirsch, J. S., J. H. Ng, D. W. Ross, P. Sharma, H. H. Shah, R. L. Barnett, A. D. Hazzan, S. Fishbane, and K. D. Jhaveri, *ACUTE KIDNEY INJURY IN PATIENTS HOSPITALIZED WITH COVID-19*. Kidney International, 2020.
3. Li, Z., M. Wu, J. Yao, J. Guo, X. Liao, S. Song, J. Li, G. Duan, Y. Zhou, X. Wu, Z. Zhou, T. Wang, M. Hu, X. Chen, Y. Fu, C. Lei, H. Dong, C. Xu, Y. Hu, M. Han, Y. Zhou, H. Jia, X. Chen, and J. Yan, *Caution on Kidney Dysfunctions of COVID-19 Patients*. medRxiv, 2020: p. 2020.02.08.20021212.
4. Richardson, S., J. S. Hirsch, M. Narasimhan, J. M. Crawford, T. McGinn, K. W. Davidson, D. P. Barnaby, L. B. Becker, J. D. Chelico, and S. L. Cohen, *Presenting characteristics, comorbidities, and outcomes among 5700 patients hospitalized with COVID-19 in the New York City area*. Jama, 2020.
5. Pan, X.-w., H. Z. Da Xu, W. Zhou, L.-h. Wang, and X.-g. Cui, *Identification of a potential mechanism of acute kidney injury during the COVID-19 outbreak: a study based on single-cell transcriptome analysis*. Intensive care medicine, 2020: p. 1.
6. Ronco, C. and T. Reis, *Kidney involvement in COVID-19 and rationale for extracorporeal therapies*. Nature Reviews Nephrology, 2020: p. 1-3.
7. Pei, G., Z. Zhang, J. Peng, L. Liu, C. Zhang, C. Yu, Z. Ma, Y. Huang, W. Liu, and Y. Yao, *Renal involvement and early prognosis in patients with COVID-19 pneumonia*. Journal of the American Society of Nephrology, 2020. 31(6): p. 1157-1165.
8. Ronco, C., T. Reis, and F. Husain-Syed, *Management of acute kidney injury in patients with COVID-19*. Lancet Respir Med, 2020.

9. Diao, B., Z. Feng, C. Wang, H. Wang, L. Liu, C. Wang, R. Wang, Y. Liu, Y. Liu, and G. Wang, *Human kidney is a target for novel severe acute respiratory syndrome coronavirus 2 (SARS-CoV-2) infection*. MedRxiv, 2020.
10. Zhou, M., X. Zhang, and J. Qu, *Coronavirus disease 2019 (COVID-19): a clinical update*. Frontiers of medicine, 2020: p. 1-10.
11. Mohamed, M. M., I. Lukitsch, A. E. Torres-Ortiz, J. B. Walker, V. Varghese, C. F. Hernandez-Arroyo, M. Alqudsi, J. R. LeDoux, and J. C. Q. Velez, *Acute kidney injury associated with coronavirus disease 2019 in Urban New Orleans*. Kidney 360, 2020: p. 10.34067/KID.0002652020.
12. Cheng, Y., R. Luo, K. Wang, M. Zhang, Z. Wang, L. Dong, J. Li, Y. Yao, S. Ge, and G. Xu, *Kidney disease is associated with in-hospital death of patients with COVID-19*. Kidney international, 2020.
13. Su, H., M. Yang, C. Wan, L.-X. Yi, F. Tang, H.-Y. Zhu, F. Yi, H.-C. Yang, A. B. Fogo, and X. Nie, *Renal histopathological analysis of 26 postmortem findings of patients with COVID-19 in China*. Kidney international, 2020.
14. Tipnis, S. R., N. M. Hooper, R. Hyde, E. Karran, G. Christie, and A. J. Turner, *A human homolog of angiotensin-converting enzyme. Cloning and functional expression as a captopril-insensitive carboxypeptidase*. J Biol Chem, 2000. 275(43): p. 33238-43.
15. Donoghue, M., F. Hsieh, E. Baronas, K. Godbout, M. Gosselin, N. Stagliano, M. Donovan, B. Woolf, K. Robison, and R. Jeyaseelan, *A novel angiotensin-converting enzyme-related carboxypeptidase (ACE2) converts angiotensin I to angiotensin 1-9*. Circulation research, 2000. 87(5): p. e1-e9.
16. Vickers, C., P. Hales, V. Kaushik, L. Dick, J. Gavin, J. Tang, K. Godbout, T. Parsons, E. Baronas, and F. Hsieh, *Hydrolysis of biological peptides by human angiotensin-converting enzyme-related carboxypeptidase*. Journal of Biological Chemistry, 2002. 277(17): p. 14838-14843.
17. Guy, J. L., R. M. Jackson, K. R. Acharya, E. D. Sturrock, N. M. Hooper, and A. J. Turner, *Angiotensin-converting enzyme-2 (ACE2): comparative modeling of the active site, specificity requirements, and chloride dependence*. Biochemistry, 2003. 42(45): p. 13185-92.
18. Brosnihan, K. B., P. Li, D. Ganten, and C. M. Ferrario, *Estrogen protects transgenic hypertensive rats by shifting the vasoconstrictor-vasodilator balance of RAS*. Am J Physiol, 1997. 273(6 Pt 2): p. R1908-15.
19. Ferrario, C. M., *ACE 2: More of Ang 1-7 or less Ang II?* Current opinion in nephrology and hypertension, 2011. 20(1): p. 1.
20. Chappell, M. C., A. C. Marshall, E. M. Alzayadneh, H. A. Shaltout, and D. I. Diz, *Update on the Angiotensin converting enzyme 2-Angiotensin (1-7)-MAS receptor axis: fetal programing, sex differences, and intracellular pathways*. Front Endocrinol (Lausanne), 2014. 4: p. 201.
21. Wysocki, J., M. Ye, E. Rodriguez, F. R. Gonzalez-Pacheco, C. Barrios, K. Evora, M. Schuster, H. Loibner, K. B. Brosnihan, C. M. Ferrario, J. M. Penninger, and D. Batlle, *Targeting the degradation of angiotensin II with recombinant angiotensin-converting enzyme 2: prevention of angiotensin II-dependent hypertension*. Hypertension, 2010. 55(1): p. 90-8.
22. Batlle, D., J. Wysocki, M. J. Soler, and K. Ranganath, *Angiotensin-converting enzyme 2: enhancing the degradation of angiotensin II as a potential therapy for diabetic nephropathy*. Kidney Int, 2012. 81(6): p. 520-8.
23. Marquez, A., J. Wysocki, J. Pandit, and D. Batlle, *An update on ACE2 amplification and its therapeutic potential*. Acta Physiol (Oxf), 2020: p. e13513.
24. Wysocki, J., A. Schulze, and D. Batlle, *Novel Variants of Angiotensin Converting Enzyme-2 of Shorter Molecular Size to Target the Kidney Renin Angiotensin System*. Biomolecules, 2019. 9(12).
25. Serfozo, P., J. Wysocki, G. Gulua, A. Schulze, M. Ye, P. Liu, J. Jin, M. Bader, T. Myohanen, J. A. Garcia-Horsman, and D. Batlle, *Ang II (Angiotensin II) Conversion to Angiotensin-(1-7) in the Circulation Is POP (Prolyloligopeptidase)-Dependent and ACE2 (Angiotensin-Converting Enzyme 2)-Independent*. Hypertension, 2020. 75(1): p. 173-182.
26. Haber, P. K., M. Ye, J. Wysocki, C. Maier, S. K. Hague, and D. Batlle, *Angiotensin-Converting Enzyme 2-Independent Action of Presumed Angiotensin-Converting Enzyme 2 Activators: Studies In Vivo, Ex Vivo, and In Vitro*. Hypertension, 2014. 63(4): p. 774-782.
27. Wysocki, J., L. Garcia-Halpin, M. Ye, C. Maier, K. Sowers, K. D. Burns, and D. Batlle, *Regulation of urinary ACE2 in diabetic mice*. Am J Physiol Renal Physiol, 2013. 305(4): p. F600-11.
28. Li, W., M. J. Moore, N. Vasilieva, J. Sui, S. K. Wong, M. A. Berne, M. Somasundaran, J. L. Sullivan, K. Luzuriaga, and T. C. Greenough, *Angiotensin-converting enzyme 2 is a functional receptor for the SARS coronavirus*. Nature, 2003. 426(6965): p. 450-454.
29. Li, F., *Receptor recognition mechanisms of coronaviruses: a decade of structural studies*. Journal of virology, 2015. 89(4): p. 1954-1964.
30. Hoffmann, M., H. Kleine-Weber, S. Schroeder, N. Kruger, T. Herrler, S. Erichsen, T. S. Schiergens, G. Herrler, N. H. Wu, A. Nitsche, M. A. Muller, C. Drosten, and S. Pohlmann, *SARS-CoV-2 Cell Entry Depends on ACE2 and TMPRSS2 and Is Blocked by a Clinically Proven Protease Inhibitor*. Cell, 2020.
31. Walls, A. C., Y.-J. Park, M. A. Tortorici, A. Wall, A. T. McGuire, and D. Veesler, *Structure, function, and antigenicity of the SARS-CoV-2 spike glycoprotein*. Cell, 2020.
32. Wrapp, D., N. Wang, K. S. Corbett, J. A. Goldsmith, C.-L. Hsieh, O. Abiona, B. S. Graham, and J. S. McLellan, *Cryo-EM structure of the 2019-nCoV spike in the prefusion conformation*. Science (New York, N.Y.), 2020. 367(6483): p. 1260-1263.
33. Lan, J., J. Ge, J. Yu, S. Shan, H. Zhou, S. Fan, Q. Zhang, X. Shi, Q. Wang, and L. Zhang, *Structure of the SARS-CoV-2 spike receptor-binding domain bound to the ACE2 receptor*. Nature, 2020. 581(7807): p. 215-220.
34. Yan, R., Y. Zhang, Y. Li, L. Xia, Y. Guo, and Q. Zhou, *Structural basis for the recognition of the SARS-CoV-2 by full-length human ACE2*. Science (New York, N.Y.), 2020: p. eabb2762.
35. Wang, Q., Y. Zhang, L. Wu, S. Niu, C. Song, Z. Zhang, G. Lu, C. Qiao, Y. Hu, K. Y. Yuen, Q. Wang, H. Zhou, J. Yan, and J. Qi, *Structural and Functional Basis of SARS-CoV-2 Entry by Using Human ACE2*. Cell, 2020.
36. Gheblawi, M., K. Wang, A. Viveiros, Q. Nguyen, J.-C. Zhong, A. J. Turner, M. K. Raizada, M. B. Grant, and G. Y. Oudit, *Angiotensin-converting enzyme 2: SARS-CoV-2 receptor and regulator of the renin-angiotensin system: celebrating the 20th anniversary of the discovery of ACE2*. Circulation research, 2020. 126(10): p. 1456-1474.
37. Verdecchia, P., C. Cavallini, A. Spanevello, and F. Angeli, *The pivotal link between ACE2 deficiency and SARS-CoV-2 infection*. Eur J Intern Med, 2020.

38. Zhang, H., J. M. Penninger, Y. Li, N. Zhong, and A. S. Slutsky, *Angiotensin-converting enzyme 2 (ACE2) as a SARS-CoV-2 receptor: molecular mechanisms and potential therapeutic target*. Intensive care medicine, 2020: p. 1-5.
39. Gurwitz, D., *Angiotensin receptor blockers as tentative SARS-CoV-2 therapeutics*. Drug development research, 2020.
40. Kuba, K., Y. Imai, S. Rao, H. Gao, F. Guo, B. Guan, Y. Huan, P. Yang, Y. Zhang, and W. Deng, *A crucial role of angiotensin converting enzyme 2 (ACE2) in SARS coronavirus-induced lung injury*. Nature medicine, 2005. 11(8): p. 875-879.
41. Sodhi, C. P., C. Wohlford-Lenane, Y. Yamaguchi, T. Prindle, W. B. Fulton, S. Wang, P. B. McCray Jr, M. Chappell, D. J. Hackam, and H. Jia, *Attenuation of pulmonary ACE2 activity impairs inactivation of des-Arg9 bradykinin/BKB1R axis and facilitates LPS-induced neutrophil infiltration*. American Journal of Physiology-Lung Cellular and Molecular Physiology, 2018. 314(1): p. L17-L31.
42. Burrell, L. M., C. I. Johnston, C. Tikellis, and M. E. Cooper, *ACE2, a new regulator of the renin-angiotensin system*. Trends in Endocrinology & Metabolism, 2004. 15(4): p. 166-169.
43. Imai, Y., K. Kuba, and J. M. Penninger, *Angiotensin-converting enzyme 2 in acute respiratory distress syndrome*. Cellular and molecular life sciences, 2007. 64(15): p. 2006-2012.
44. Garvin, M. R., C. Alvarez, J. I. Miller, E. T. Prates, A. M. Walker, B. K. Amos, A. E. Mast, A. Justice, B. Aronow, and D. Jacobson, *A mechanistic model and therapeutic interventions for COVID-19 involving a RAS-mediated bradykinin storm*. Elife, 2020. 9: p. e59177.
45. Tolouian, R., S. Z. Vahed, S. Ghiyasvand, A. Tolouian, and M. Ardalan, *COVID-19 interactions with angiotensin-converting enzyme 2 (ACE2) and the kinin system; looking at a potential treatment*. Journal of Renal Injury Prevention, 2020. 9(2): p. e19-e19.
46. Batlle, D., J. Wysocki, and K. Satchell, *Soluble angiotensin-converting enzyme 2: a potential approach for coronavirus infection therapy?*. Clin Sci, 2020. 134: p. 543-545.
47. Zoufaly, A., M. Poglitsch, J. H. Aberle, W. Hoepler, T. Seitz, M. Traugott, A. Grieb, E. Pawelka, H. Laferl, and C. Wenisch, *Human recombinant soluble ACE2 in severe COVID-19*. The Lancet Respiratory Medicine, 2020.
48. Haschke, M., M. Schuster, M. Poglitsch, H. Loibner, M. Salzberg, M. Bruggisser, J. Penninger, and S. Krahenbuhl, *Pharmacokinetics and pharmacodynamics of recombinant human angiotensin-converting enzyme 2 in healthy human subjects*. Clin Pharmacokinet, 2013. 52(9): p. 783-92.
49. Mina Shirazi, J. W., Minghao Ye, Chad Haney, Ming Zhao, Yasphal Kanwar, Jenny Zhang Zheng, and Daniel Batlle *Novel ACE2 truncate for acute kidney injury*. ASN abstarct, 2019.
50. Liu, P., J. Wysocki, T. Souma, M. Ye, V. Ramirez, B. Zhou, L. D. Wilsbacher, S. E. Quaggin, D. Batlle, and J. Jin, *Novel ACE2-Fc chimeric fusion provides long-lasting hypertension control and organ protection in mouse models of systemic renin angiotensin system activation*. Kidney international, 2018. 94(1): p. 114-125.
51. Kruse, R. L., *Therapeutic strategies in an outbreak scenario to treat the novel coronavirus originating in Wuhan, China*. F1000Res, 2020. 9: p. 72.
52. Ziegler, C. G., S. J. Allon, S. K. Nyquist, I. M. Mbano, V. N. Miao, C. N. Tzouanas, Y. Cao, A. S. Yousif, J. Bals, and B. M. Hauser, *SARS-CoV-2 receptor ACE2 is an interferon-stimulated gene in human airway epithelial cells and is detected in specific cell subsets across tissues*. Cell, 2020.
53. Strohl, W. R., *Fusion Proteins for Half-Life Extension of Biologics as a Strategy to Make Biobetters*. BioDrugs, 2015. 29(4): p. 215-39.
54. Kontermann, R. E., *Strategies for extended serum half-life of protein therapeutics*. Curr Opin Biotechnol, 2011. 22(6): p. 868-76.
55. Sand, K. M., B. Dalhus, G. J. Christianson, M. Bern, S. Foss, J. Cameron, D. Sleep, M. Bjoras, D. C. Roopenian, I. Sandlie, and J. T. Andersen, *Dissection of the neonatal Fc receptor (FcRn)-albumin interface using mutagenesis and anti-FcRn albumin-blocking antibodies*. J Biol Chem, 2014. 289(24): p. 17228-39.
56. Levy, O. E., C. M. Jodka, S. S. Ren, L. Mamedova, A. Sharma, M. Samant, L. J. D'Souza, C. J. Soares, D. R. Yuskin, L. J. Jin, D. G. Parkes, K. Tatarkiewicz, and S. S. Ghosh, *Novel exenatide analogs with peptidic albumin binding domains: potent anti-diabetic agents with extended duration of action*. PLoS One, 2014. 9(2): p. e87704.
57. Wysocki, J., M. Ye, A. M. Khattab, A. Fogo, A. Martin, N. V. David, Y. Kanwar, M. Osborn, and D. Batlle, *Angiotensin-converting enzyme 2 amplification limited to the circulation does not protect mice from development of diabetic nephropathy*. Kidney Int, 2017. 91(6): p. 1336-1346.
58. Fleming, A. B. and V. Raabe, *Current studies of convalescent plasma therapy for COVID-19 may underestimate risk of antibody-dependent enhancement*. J Clin Virol, 2020. 127: p. 104388.
59. Wan, Y., J. Shang, S. Sun, W. Tai, J. Chen, Q. Geng, L. He, Y. Chen, J. Wu, Z. Shi, Y. Zhou, L. Du, and F. Li, *Molecular Mechanism for Antibody-Dependent Enhancement of Coronavirus Entry*. J Virol, 2020. 94(5).
60. Davidson, A. M., J. Wysocki, and D. Batlle, *The interaction of SARS-CoV-2 and other coronavirus with Angiotensin Converting Enzyme 2 (ACE2) as their main receptor: therapeutic implications*. Hypertension, 2020.
61. Wysocki, J., E. Lores, M. Ye, M. J. Soler, and D. Batlle, *Kidney and Lung ACE2 expression after an ACE inhibitor or an Ang II receptor blocker: implications for COVID-19*. bioRxiv, 2020: p. 2020.05.20.106658.
62. Zhuang, M. W., Y. Cheng, J. Zhang, X. M. Jiang, L. Wang, J. Deng, and P. H. Wang, *Increasing Host Cellular Receptor—Angiotensin-Converting Enzyme 2 (ACE2) Expression by Coronavirus may Facilitate 2019-nCoV (or SARS-CoV-2) Infection*. Journal of Medical Virology, 2020.
63. Onabajo, O. O., A. R. Banday, W. Yan, A. Obajemu, M. L. Stanifer, D. M. Santer, O. Florez-Vargas, H. Piontkivska, J. Vargas, C. Kee, D. L. J. Tyrrell, J. L. Mendoza, S. Boulant, and L. Prokunina-Olsson, *Interferons and viruses induce a novel primate-specific isoform dACE2 and not the SARS-CoV-2 receptor ACE2*. bioRxiv, 2020.
64. Fatehullah, A., S. H. Tan, and N. Barker, *Organoids as an in vitro model of human development and disease*. Nature cell biology, 2016. 18(3): p. 246-254.
65. Wimmer, R. A., A. Leopoldi, M. Aichinger, N. Wick, B. Hantusch, M. Novatchkova, J. Taubenschmid, M. Hammerle, C. Esk, J. A. Bagley, D. Lindenhofer, G. Chen, M. Boehm, C. A. Agu, F. Yang, B. Fu, J. Zuber, J. A. Knoblich, D. Kerjaschki, and J. M. Penninger, *Human*

*blood vessel organoids as a model of diabetic vasculopathy.* Nature, 2019. 565(7740): p. 505-510.
66. Morizane, R., A. Q. Lam, B. S. Freedman, S. Kishi, M. T. Valerius, and J. V. Bonventre, *Nephron organoids derived f from human pluripotent stem cells model kidney development and injury.* Nature biotechnology, 2015. 33(11): p. 1193.
67. Morizane, R. and J. V. Bonventre, *Generation of nephron progenitor cells and kidney organoids from human pluripotent stem cells.* Nature protocols, 2017. 12(1): p. 195.
68. Monteil, V., H. Kwon, P. Prado, A. Hagelkruys, R. A. Wimmer, M. Stahl, A. Leopoldi, E. Garreta, C. Hurtado Del Pozo, F. Prosper, J. P. Romero, G. Wirnsberger, H. Zhang, A. S. Slutsky, R. Conder, N. Montserrat, A. Mirazimi, and J. M. Penninger, *Inhibition of SARS-CoV-2 Infections in Engineered Human Tissues Using Clinical-Grade Soluble Human ACE2.* Cell, 2020. 181(4): p. 905-913 e7.
69. Elbadawi, M. and T. Efferth, *Organoids of human airways to study infectivity and cytopathy of SARS-CoV-2.* Lancet Respir Med, 2020.
70. Schaller, T., K. Hirschbühl, K. Burkhardt, G. Braun, M. Trepel, B. Märkl, and R. Claus, *Postmortem examination of patients with COVID-19.* JAMA, 2020.
71. Li, W., T. C. Greenough, M. J. Moore, N. Vasilieva, M. Somasundaran, J. L. Sullivan, M. Farzan, and H. Choe, *Efficient replication of severe acute respiratory syndrome coronavirus in mouse cells is limited by murine angiotensin-converting enzyme 2.* J Virol, 2004. 78(20): p. 11429-33.
72. McCray, P. B., L. Pewe, C. Wohlford-Lenane, M. Hickey, L. Manzel, L. Shi, J. Netland, H. P. Jia, C. Halabi, and C. D. Sigmund, *Lethal infection of K18-hACE2 mice infected with severe acute respiratory syndrome coronavirus.* Journal of virology, 2007. 81(2): p. 813-821.
73. Glass, W. G., K. Subbarao, B. Murphy, and P. M. Murphy, *Mechanisms of host defense following severe acute respiratory syndrome-coronavirus (SARS-CoV) pulmonary infection of mice.* The Journal of Immunology, 2004. 173(6): p. 4030-4039.
74. Winkler, E. S., A. L. Bailey, N. M. Kafai, S. Nair, B. T. McCune, J. Yu, J. M. Fox, R. E. Chen, J. T. Earnest, and S. P. Keeler, *SARS-CoV-2 infection of human ACE2-transgenic mice causes severe lung inflammation and impaired function.* Nature immunology, 2020: p. 1-9.
75. Oladunni, F. S., J.-G. Park, P. P. Tamayo, O. Gonzalez, A. Akhter, A. Allué-Guardia, A. Olmo-Fontánez, S. Gautam, A. Garcia-Vilanova, and C. Ye, *Lethality of SARS-CoV-2 infection in K18 human angiotensin converting enzyme 2 transgenic mice.* bioRxiv, 2020.
76. Yang, X. H., W. Deng, Z. Tong, Y. X. Liu, L. F. Zhang, H. Zhu, H. Gao, L. Huang, Y. L. Liu, C. M. Ma, Y. F. Xu, M. X. Ding, H. K. Deng, and C. Qin, *Mice transgenic for human angiotensin-converting enzyme 2 provide a model for SARS coronavirus infection.* Comp Med, 2007. 57(5): p. 450-9.
77. Wysocki, J., M. Ye, A. M. Khattab, A. Fogo, A. Martin, N. V. David, Y. Kanwar, M. Osborn, and D. Batlle, *Angiotensin-converting enzyme 2 amplification limited to the circulation does not protect mice from development of diabetic nephropathy.* Kidney international, 2017. 91(6): p. 1336-1346.
78. Ye, M., J. Wysocki, F. R. Gonzales-Pacheco, M. Salem, K. Evora, L. Garcia-Halpin, M. Poglitsch, M. Schuster, and D. Batlle, *Murine Recombinant ACE2: Effect on Angiotensin II Dependent Hypertension and Distinctive ACE2 Inhibitor Characteristics on rodent and human ACE2.* Hypertension, 2012. 60(3): p. 730.
79. Imai, Y., K. Kuba, S. Rao, Y. Huan, F. Guo, B. Guan, P. Yang, R. Sarao, T. Wada, H. Leong-Poi, M. A. Crackower, A. Fukamizu, C. C. Hui, L. Hein, S. Uhlig, A. S. Slutsky, C. Jiang, and J. M. Penninger, *Angiotensin-converting enzyme 2 protects from severe acute lung failure.* Nature, 2005. 436(7047): p. 112-6.
80. Yang, X., Y. Yu, J. Xu, H. Shu, H. Liu, Y. Wu, L. Zhang, Z. Yu, M. Fang, and T. Yu, *Clinical course and outcomes of critically ill patients with SARS-CoV-2 pneumonia in Wuhan, China: a single-centered, retrospective, observational study.* The Lancet Respiratory Medicine, 2020.
81. Guan, W.-j., Z.-y. Ni, Y. Hu, W.-h. Liang, C.-q. Ou, J.-x. He, L. Liu, H. Shan, C.-l. Lei, and D. S. Hui, *Clinical characteristics of coronavirus disease 2019 in China.* New England journal of medicine, 2020. 382(18): p. 1708-1720.
82. Zheng, Y.-Y., Y.-T. Ma, J.-Y. Zhang, and X. Xie, *COVID-19 and the cardiovascular system.* Nature Reviews Cardiology, 2020. 17(5): p. 259-260.
83. Guo, W., M. Li, Y. Dong, H. Zhou, Z. Zhang, C. Tian, R. Qin, H. Wang, Y. Shen, and K. Du, *Diabetes is a risk factor for the progression and prognosis of COVID-19.* Diabetes/metabolism research and reviews, 2020: p. e3319.
84. Simonnet, A., M. Chetboun, J. Poissy, V. Raverdy, J. Noulette, A. Duhamel, J. Labreuche, D. Mathieu, F. Pattou, and M. Jourdain, *High prevalence of obesity in severe acute respiratory syndrome coronavirus-2 (SARS-CoV-2) requiring invasive mechanical ventilation.* Obesity, 2020.
85. Limberis, M. P., L. H. Vandenberghe, L. Zhang, R. J. Pickles, and J. M. Wilson, *Transduction efficiencies of novel AAV vectors in mouse airway epithelium in vivo and human ciliated airway epithelium in vitro.* Molecular Therapy, 2009. 17(2): p. 294-301.
86. Gruntman, A. M., C. Mueller, T. R. Flotte, and G. Gao, *Gene Transfer in the Lung Using Recombinant Adeno-Associated Virus.* Current protocols in microbiology, 2012. 26(1): p. 14D. 2.1-14D. 2.17.
87. Flotte, T., B. Carter, C. Conrad, W. Guggino, T. Reynolds, B. Rosenstein, G. Taylor, S. Walden, and R. Wetzel, *A phase i study of an adeno-associated virus-cftr gene vector in adult cf patients with mild lung disease. Johns hopkins children's center, baltimore, Md.* Human gene therapy, 1996. 7(9): p. 1145-1159.
88. Pfeifer, C., M. Aneja, G. Hasenpusch, and C. Rudolph, *Adeno-associated virus serotype 9-mediated pulmonary transgene expression: effect of mouse strain, animal gender and lung inflammation.* Gene therapy, 2011. 18(11): p. 1034-1042.
89. Hassan, A. O., J. B. Case, E. S. Winkler, L. Thackray, N. M. Kafai, A. L. Bailey, B. T. McCune, J. M. Fox, R. E. Chen, and W. B. Al Soussi, *A SARS-CoV-2 infection model in mice demonstrates protection by neutralizing antibodies.* Cell, 2020.
90. Chung, D. C., B. Fogelgren, K. M. Park, J. Heidenberg, X. Zuo, L. Huang, J. Bennett, and J. H. Lipschutz, *Adeno-Associated Virus-Mediated Gene Transfer to Renal Tubule Cells via a Retrograde Ureteral Approach.* Nephron Extra, 2011. 1(1): p. 217-23.
91. Soler, M. J., M. Riera, and D. Batlle, *New experimental models of diabetic nephropathy in mice models of type 2 diabetes: efforts to replicate human nephropathy.* Experimental diabetes research, 2012. 2012.

92. Morais, R. L., A. M. Hilzendeger, B. Visniauskas, M. Todiras, N. Alenina, M. A. Mori, R. C. Araújo, C. R. Nakaie, J. R. Chagas, and A. K. Carmona, *High aminopeptidase A activity contributes to blood pressure control in ob/ob mice by AT2 receptor-dependent mechanism*. American Journal of Physiology-Heart and Circulatory Physiology, 2017. 312(3): p. H437-H445.

93. Hudkins, K. L., W. Pichaiwong, T. Wietecha, J. Kowalewska, M. C. Banas, M. W. Spencer, A. Muhlfeld, M. Koelling, J. W. Pippin, S. J. Shankland, B. Askari, M. E. Rabaglia, M. P. Keller, A. D. Attie, and C. E. Alpers, *BTBR Ob/Ob mutant mice model progressive diabetic nephropathy*. J Am Soc Nephrol, 2010. 21(9): p. 1533-42.

94. Huby, A.-C., P. Kavvadas, C. Alfieri, A. Abed, J. Toubas, M.-P. Rastaldi, J.-C. Dussaule, C. Chatziantoniou, and C. E. Chadjichristos, *The RenTg mice: a powerful tool to study renin-dependent chronic kidney disease*. PLoS One, 2012. 7(12): p. e52362.

95. Nakano, D., K. Kitada, N. Wan, Y. Zhang, H. Wiig, K. Wararat, M. Yanagita, S. Lee, L. Jia, J. M. Titze, and A. Nishiyama, *Lipopolysaccharide induces filtrate leakage from renal tubular lumina into the interstitial space via a proximal tubular Toll-like receptor 4-dependent pathway and limits sensitivity to fluid therapy in mice*. Kidney Int, 2020. 97(5): p. 904-912.

96. Bao, Y. W., Y. Yuan, J. H. Chen, and W. Q. Lin, *Kidney disease models: tools to identify mechanisms and potential therapeutic targets*. Zool Res, 2018. 39(2): p. 72-86.

97. Doi, K., A. Leelahavanichkul, P. S. Yuen, and R. A. Star, *Animal models of sepsis and sepsis-induced kidney injury*. J Clin Invest, 2009. 119(10): p. 2868-78.

98. Baranova, I. N., A. C. Souza, A. V. Bocharov, T. G. Vishnyakova, X. Hu, B. L. Vaisman, M. J. Amar, Z. Chen, Y. Kost, A. T. Remaley, A. P. Patterson, P. S. Yuen, R. A. Star, and T. L. Eggerman, *Human SR-BI and SR-BII Potentiate Lipopolysaccharide-Induced Inflammation and Acute Liver and Kidney Injury in Mice*. J Immunol, 2016. 196(7): p. 3135-47.

Example 6: Exemplary Covalent Multimer Agents

As noted herein, in some embodiments, soluble ACE2 variant polypeptide variants useful in accordance with the present disclosure may comprise covalently-linked multimers of individual ACE2 moieties. In some particular embodiments, 2-4 ACE 2 fragments (which may, in some embodiments, be identical or substantially identical to one another) are joined together, for example through a single unique Cysteine SH group on each fragment, and crosslinked (e.g., via divalent or tetravalent PEG reagents uniquely reactive with Cys-SH). Because free Cys261 alone (non-disulfide) is present in all CoV-2 active C-terminal truncates ending before aa498, and Cys498 is present in all larger active C-terminal truncates that include aa 619, these two sites (C261 and C498) are available to form dimers and tetramers through specific sulfhydryl reactions with commercially available bis and tetra maleimido PEGs, such as, for example PEGs spanning lengths from about 50 Å to about 90 Å to about 150 Å extending between attached Cys SH groups.

In some embodiments of multimeric agents linked via SH moieties, participating ACE2 moieties are modified to contain only a single Cys residue, so that chemically defined homogeneous crosslinking can be achieved. Thus, in such embodiments, when Cys261 is used for crosslinking, Cys498 is absent (e.g., is substituted or removed); when Cys498 is used for crosslinking, Cys261 is absent. Other unique Cys residues may be introduced for crosslinking if both Cys261 and Cys498 are absent. Such crosslinking would be limited to ACE2 fragments with C-terminus preceding aa 529, or may include Cys530 as a C-terminus if both C261 and C498 are absent.

In some embodiments, multimeric agents provided herein utilize an ACE2 C-terminal truncate as the ACE2 moiety. In some such embodiments, the C-terminus is between about aa 370 and about aa 498 (which ACE2 truncate may have a molecular weight, for example, ranging from about 39 kD to about 55 kD), and a unique free SH may be present at Cys261. Alternatively, in some such C-terminus is between about aa 375 and aa 498, and Cys261 is mutated, for example to Ser or Ala. Still further alternatively, in some such embodiments, such Ce-terminus is between aa 500 to ACE aa 530 and both C261 and C498 are mutated, for example to Ser or Ala. ACE2 variants having such modifications and/or molecular weights are contemplated herein and may be utilized in the methods disclosed herein to bind and intercept SARS-CoV-2 and/or other viruses that use ACE2 as the receptor for cell entry.

Example 7: Pharmacokinetics, Binding Activity, and Efficacy of ACE2 Variants for Treating and Preventing SARS-CoV-2 Infection in an Animal Model Generation of a Soluble ACE2 Variant with Not Only Extended Duration of Action But Also Enhanced Binding to the Receptor Binding Domain of SARS-CoV-2

Recombinant human ACE2 protein chimeras were generated using an approach similar to that recently described (1, 2). Briefly, a cDNA coding for C-terminal portion of the 618 amino acids fragment of human ACE2 protein (termed ace2 1-618) was fused with the abd cDNA encoding for a small albumin binding domain (ABD) protein (5-kD) (3) in order to prolong in vivo duration of action of ACE2 as described previously (1). A flexible linker (g4s3) was placed between the N terminal end of the abd cDNA (IDT) and the C-terminal end of ace2 1-618. The dimerization of the ACE2-ABD chimeric protein was achieved by inserting a cDNA coding for a hinge-like region containing dodecapeptide motif termed DDC between g4s3 and the c-terminus of the cDNA for ace2 1-618. The cDNA of the fusion chimera termed ace2 1-618-ddc-abd was then inserted into pcDNA3-4 plasmid (Invitrogen) using custom synthesized complementary primers (IDT) and the Gibson assembly kit (NEB). After verifying the DNA sequence of the pcDNA3-4 fused with the cDNA for ace2 1-618-ddc-abd, the protein was produced in expi293 cells and purified using Fast Protein Liquid Chromatography on Q-Sepharose followed by size exclusion chromatography on Superdex to ~95% purity in the Recombinant Protein Core at Northwestern University in Evanston.

The Efficacy of the ACE2 618-DDC-ABD Protein in an In Vivo Infectivity Protocol

The efficacy of the ACE2 618-DDC-ABD was tested in a transgenic mouse model, K18-hACE2 which expresses full-length human ACE2 and is susceptible to SARS -CoV-2 infection. All work with SARS-CoV-2 was performed in the BSL-3 Facility of the Ricketts Institute, University of Chicago. A total of 20 transgenic K18-hACE2 mice were used (n=20, 10 males and 10 females). All animals were infected with SARS-CoV-2 suspended in PBS given by intranasal inoculation ($10^5$ $TCID_{50}$). ACE2 618-DDC-ABD was delivered (n=5 male, n=5 female) intranasally 1 hour prior to viral challenge (30 μl, 10-12 μg/g BW). In addition, animals were given intranasally the same dose 24 and 48 hours after inoculation for a total of 3 doses (1 pre- and 2 post-inoculation). Additionally, at the same time-points (1 hour pre- and 24 and 48 hours post-inoculation) an i.p. injection of ACE2 1-618-DDC-ABD (200 µl, 1 µg/g BW, in PBS) was administered. Control animals (n=5 male, n=5 female) received i.n. and i.p. the same volumes of PBS and at the same time-points as the treatment group.

All animals were weighed once daily and monitored for health using a clinical scoring system evaluated twice daily. Animals that lost more than 20% of their baseline body weight or had a clinical score of ≥3 were sacrificed as per study design. Accordingly, the need for sacrifice of those mice was considered a fatal event (see FIG. 22 for results). Therefore, mortality rate was 100% in infected animals both males and females. By contrast, in animals treated with ACE2 1-618-DDC-ABD mortality was not observed in any female or male mice at the 5-6 days end point. Only one treated male mouse had to be sacrificed at day 14 for unexplained weight loss. The data on viral titers by plaque assay (see FIG. 23) is consistent with the clinical results. As shown viral titers in the lungs were markedly decreased in treated animals by day 6 and completely normal in the remaining treated animals.

REFERENCES

1. Wysocki J, Ye M, Hassler L, Gupta A K, Wang Y, Nicoleascu V, et al. A Novel Soluble ACE2 Variant with Prolonged Duration of Action Neutralizes SARS-CoV-2 Infection in Human Kidney Organoids. J Am Soc Nephrol. 2021.
2. Wysocki J, Schulze A, Batlle D. Novel Variants of Angiotensin Converting Enzyme-2 of Shorter Molecular Size to Target the Kidney Renin Angiotensin System. Biomolecules. 2019; 9(12)
3. Jacobs S A, Gibbs A C, Conk M, Yi F, Maguire D, Kane C, et al. Fusion to a highly stable consensus albumin binding domain allows for tunable pharmacokinetics. Protein engineering, design & selection: PEDS. 2015; 28(10):385-93.

Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A fusion polypeptide comprising, from N-terminus to C-terminus:
   a fragment of human angiotensin converting enzyme 2 ("ACE2") that represents an N-terminal deletion or a C-terminal deletion, or both, relative to full-length human ACE2 and that includes cysteine residues at positions corresponding to C344 and C361 of full-length human ACE2; fused at its C-terminus to a heterologous or exogenous amino acid sequence that comprises:
   (i) a DDC multimerization motif of SEQ ID NO:16; and,
   (ii) an amino acid sequence of serum albumin binding domain of streptococcal protein G or a fragment thereof,
wherein the fusion polypeptide is characterized by one or more of:
   (a) the fusion polypeptide is soluble and binds a SARS-COV-2 spike protein;
   (b) the fusion polypeptide has an extended duration of action relative to the fragment of ACE2 alone.

2. The fusion polypeptide of claim 1, further comprising an amino acid tag sequence.

3. A pharmaceutical composition that comprises or delivers
   (i) the fusion polypeptide of claim 1; and
   (ii) a suitable pharmaceutical carrier.

4. A method for treating and/or preventing any coronavirus infection that uses ACE2 as the receptor in a subject in need thereof, the method comprising administering to the subject the pharmaceutical composition of claim 3.

5. The fusion polypeptide of claim 1, wherein the full-length ACE2 has an amino acid sequence as set forth in SEQ ID NO:1.

6. The fusion polypeptide of claim 1, wherein the fragment of ACE2 includes fewer than 650 amino acids of ACE2.

7. The fusion polypeptide of claim 1, wherein the fusion polypeptide has a binding affinity for SARS-COV-2 spike protein of less than 1000 nM, 500 nM, 100 nM, 50 nM, 40 nM, 30 nM, 20 nM, 10 nM, 5 nM, 1 nM, or lower.

8. The fusion polypeptide of claim 1, wherein the fragment of ACE2 lacks the ACE2 leader polypeptide.

9. The fusion polypeptide of claim 1, wherein the fusion polypeptide has a duration of action in plasma of at least 6 hours, 12 hours, 1 day, 2 days, 3 days, 4 days, 5 days, 6 days, one week, two weeks, or longer.

10. The fusion polypeptide of claim 5, wherein the fragment of ACE2 has the amino acid sequence of SEQ ID NO:10 (a.a. 1-618 of SEQ ID NO:1).

11. The fusion polypeptide of claim 1, wherein the fusion polypeptide has ACE2 enzymatic activity.

12. The fusion polypeptide of claim 1, wherein the heterologous or exogenous amino acid sequence comprises domain III of human serum albumin, or a fragment thereof.

13. The fusion polypeptide of claim 12, wherein the amino acid sequence of the domain III of human serum albumin is SEQ ID NO:9.

14. A polypeptide comprising from N-terminus to C-terminus:
   a fragment of ACE2 that is shorter than full-length ACE2 with a C-terminal truncation that removes the transmembrane region and C-terminal region of ACE2;
   a DDC multimerization motif of SEQ ID NO:16;
   a flexible linker; and
   a serum albumin binding domain (ABD) of streptococcal protein G or a fragment thereof.

15. A pharmaceutical composition that comprises or delivers
   (i) the fusion polypeptide of claim 1 or the polypeptide of claim 14; and
   (ii) a suitable pharmaceutical carrier.

16. The fusion polypeptide of claim 1, in dimer form.

17. The fusion polypeptide of claim 14, in dimer form.

18. A fusion polypeptide that comprises from N-terminus to C-terminus:
   (a) a soluble fragment of ACE2 that includes fewer than 650 consecutive amino acids of ACE2 and binds to a SARS-COV-2 spike protein;
   (b) a DDC multimerization motif of SEQ ID NO:16;
   (c) a flexible linker; and
   (d) a heterologous amino acid sequence of serum albumin binding domain of streptococcal protein G or a fragment thereof.

19. The fusion polypeptide of claim 18, wherein the soluble fragment of ACE2 is 1-618 of SEQ ID NO:10.

20. The fusion polypeptide of claim 18, wherein the heterologous amino acid sequence is a serum albumin binding domain of about 5 kDa.

21. The fusion polypeptide of claim 18, wherein the flexible linker is or comprises G4S3.

22. The fusion polypeptide of claim 21, wherein the fragment of ACE2 is 1-618 of SEQ ID NO:10.

23. A method for treating and/or preventing any coronavirus infection that uses ACE2 as the receptor in a subject in need thereof, the method comprising administering to the subject the pharmaceutical composition of claim 15.

24. The polypeptide of claim 14, wherein the C-terminal truncation deletes amino acids corresponding to those after residue 618 of human ACE2.

25. The polypeptide of claim 14, wherein the flexible linker is a G4S3 linker.

26. The polypeptide of claim 25, wherein the fragment of ACE2 consists of amino acids corresponding to residues 1-618 of SEQ ID NO: 1.

27. The fusion polypeptide of claim 1, wherein the fragment of ACE2 includes amino acid residues corresponding to those between residues 523 and 605 of SEQ ID NO:1.

28. The fusion polypeptide of claim 27, wherein the fragment of ACE2 includes amino acid residues corresponding to those between residues 523 and 618 of SEQ ID NO:1.

29. The fusion polypeptide of claim 18, wherein the flexible linker comprises SEQ ID NO: 14.

30. The polypeptide of claim 14, wherein the flexible linker comprises SEQ ID NO:14.

* * * * *